(12) United States Patent
Vogt et al.

(10) Patent No.: US 11,154,343 B2
(45) Date of Patent: *Oct. 26, 2021

(54) DEVICE AND METHOD FOR STORING AND MIXING BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

( * ) Notice: Subject to any disclaimer, the term of this patent is extended or adjusted under 35 U.S.C. 154(b) by 627 days.

This patent is subject to a terminal disclaimer.

(21) Appl. No.: 15/807,796

(22) Filed: Nov. 9, 2017

(65) Prior Publication Data

US 2018/0132919 A1 May 17, 2018

(30) Foreign Application Priority Data

Nov. 11, 2016 (DE) ...................... 10 2016 121 607.0

(51) Int. Cl.
*A61B 17/88* (2006.01)
*A61L 24/04* (2006.01)
(Continued)

(52) U.S. Cl.
CPC ...... *A61B 17/8833* (2013.01); *A61B 17/8822* (2013.01); *A61B 17/8825* (2013.01);
(Continued)

(58) Field of Classification Search
CPC ............ A61B 17/8816; A61B 17/8822; A61B 17/8825; A61B 17/8827; A61B 17/8833;
(Continued)

(56) References Cited

U.S. PATENT DOCUMENTS 3,739,947 A 6/1973 Baumann et al.
3,756,390 A * 9/1973 Abbey .................. A61M 5/284
206/219

(Continued)

FOREIGN PATENT DOCUMENTS

CN 101505860 8/2009
DE 3640279 6/1987
(Continued)

OTHER PUBLICATIONS

Charnley, J., "Anchorage of the Femoral Head Prosthesis of the Shaft of the Femur," The Journal of Bone and Joint Surgery, 42 B, No. 1, pp. 28-30 (Feb. 1960).
(Continued)

*Primary Examiner* — Anu Ramana
(74) *Attorney, Agent, or Firm* — Dicke, Billig & Czaja, PLLC

(57) ABSTRACT

One aspect relates to a device for mixing a polymethyl methacrylate bone cement formed of two starting components and for storing the starting components of the bone cement. The device has a tubular cartridge with a cylindrical interior. A powder is contained in a front of the cartridge and a container containing a monomer liquid is arranged in a rear of the cartridge. A discharge piston is arranged between the container and the powder, and a conveying piston is on the side of the container opposite the discharge piston. The discharge piston and the conveying piston are arranged in the interior of the cartridge movably in the longitudinal direction. A conduit is provided that connects the front part and the rear part of the interior of the cartridge to one another in a manner permeable for the monomer liquid and for gases and which is impermeable for the powder.

32 Claims, 21 Drawing Sheets

(51) Int. Cl.
    *A61M 5/28*       (2006.01)
    *B01F 3/12*        (2006.01)
    *B01F 13/00*      (2006.01)
    *B01F 15/00*      (2006.01)
    *B01F 15/02*      (2006.01)
    *B05C 17/005*     (2006.01)

(52) U.S. Cl.
    CPC .......... *A61L 24/043* (2013.01); *A61M 5/284* (2013.01); *A61M 5/285* (2013.01); *B01F 3/12* (2013.01); *B01F 13/0023* (2013.01); *B01F 15/00954* (2013.01); *B01F 15/0206* (2013.01); *B01F 15/0223* (2013.01); *B01F 15/0237* (2013.01); *B01F 15/0279* (2013.01); *B05C 17/00553* (2013.01); *B05C 17/00576* (2013.01); *A61B 2017/8838* (2013.01); *B01F 2215/0029* (2013.01)

(58) Field of Classification Search
    CPC ......... A61B 2017/8838; B01F 13/0023; B01F 2215/0029; A61M 5/284; A61M 5/285
    See application file for complete search history.

(56) References Cited

U.S. PATENT DOCUMENTS

| | | | |
|---|---|---|---|
| 4,226,236 A * | 10/1980 | Genese | A61M 5/284 604/125 |
| 4,515,930 A * | 5/1985 | Omura | C08F 230/02 526/276 |
| 4,613,326 A * | 9/1986 | Szwarc | A61M 5/284 604/89 |
| 4,650,847 A * | 3/1987 | Omura | A61K 6/76 526/276 |
| 4,671,263 A | 6/1987 | Draenert | |
| 4,758,096 A | 7/1988 | Gunnarsson | |
| 4,963,151 A * | 10/1990 | Ducheyne | A61B 17/8802 428/297.4 |
| 4,973,168 A | 11/1990 | Chan | |
| 5,100,241 A | 3/1992 | Chan | |
| 5,114,421 A * | 5/1992 | Polak | A61J 1/06 604/403 |
| 5,344,232 A | 9/1994 | Nelson et al. | |
| 5,429,603 A | 7/1995 | Morris | |
| 5,549,380 A | 8/1996 | Lidgren et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,033,105 A | 3/2000 | Barker et al. | |
| 6,395,006 B1 * | 5/2002 | Burchett | A61B 17/8816 606/92 |
| 6,709,149 B1 | 3/2004 | Tepic | |
| 6,958,212 B1 * | 10/2005 | Hubbell | C12N 5/0068 424/78.17 |
| 8,361,078 B2 * | 1/2013 | Beyar | A61B 17/7095 606/94 |
| 8,376,987 B2 * | 2/2013 | Kuhn | A61M 5/284 604/82 |
| 2002/0043542 A1 | 4/2002 | Chan | |
| 2002/0049405 A1 | 4/2002 | Deslauriers et al. | |
| 2003/0220245 A1 * | 11/2003 | Hubbell | A61K 31/7088 525/50 |
| 2008/0312588 A1 | 12/2008 | Faccioli et al. | |
| 2009/0314803 A1 | 12/2009 | Keller | |
| 2011/0060274 A1 * | 3/2011 | Kuhn | A61M 5/385 604/82 |
| 2012/0155214 A1 | 6/2012 | Faccioli et al. | |
| 2013/0145727 A1 * | 6/2013 | Vogt | B65B 69/00 53/381.1 |
| 2016/0100875 A1 | 4/2016 | Faccioli et al. | |
| 2016/0310632 A1 * | 10/2016 | Rodrigues | A61L 24/001 |

FOREIGN PATENT DOCUMENTS

| | | |
|---|---|---|
| DE | 4409610 | 9/1995 |
| DE | 69812726 | 2/2004 |
| DE | 102009031178 | 9/2010 |
| EP | 0692229 | 1/1996 |
| EP | 0796653 | 9/1997 |
| EP | 1005901 | 6/2000 |
| EP | 1016452 | 7/2000 |
| EP | 1020167 | 7/2000 |
| EP | 1886647 | 2/2008 |
| EP | 2730296 | 5/2014 |
| JP | 8-57284 | 3/1996 |
| JP | 2008-540014 | 11/2008 |
| WO | 9426403 | 11/1994 |
| WO | 9967015 | 12/1999 |
| WO | 0035506 | 6/2000 |

OTHER PUBLICATIONS

Notice of Allowance in U.S. Appl. No. 15/807,776 dated Mar. 11, 2020.

\* cited by examiner

DEVICE AND METHOD FOR STORING AND MIXING BONE CEMENT

CROSS-REFERENCE TO RELATED APPLICATIONS

This Utility patent application claims priority to German Patent Application No. DE 10 2016 121 607.0, filed on Nov. 11, 2016, which is incorporated herein by reference.

BACKGROUND

One aspect relates to a device for mixing a polymethyl methacrylate bone cement from two starting components and for storing the starting components of the bone cement, the device having a tubular cartridge with a cylindrical interior.

One aspect also relates to a method for mixing and applying a bone cement using a device of this kind, and to a method for producing a prepacked PMMA cement cartridge system, which is suitable for mixing and applying a PMMA bone cement dough and in which a powder is stored as a starting component of the bone cement.

Polymethyl methacrylate (PMMA) bone cements can be traced back to the ground-breaking work of Sir Charnley (Charnley, J.: Anchorage of the femoral head prosthesis of the shaft of the femur. J. Bone Joint Surg. 42 (1960) 28-30.). PMMA bone cements consist of a liquid monomer component and a powder component. The monomer component generally contains the monomer methyl methacrylate and an activator (N,N-dimethyl-p-toluidine) dissolved therein. The powder component, also referred to as bone cement powder, includes one or more polymers, which are produced on the basis of methyl methacrylate and comonomers, such as styrene, methyl acrylate or similar monomers by polymerisation, preferably suspension polymerisation, and includes a radiopacer and the initiator dibenzoyl peroxide. As the powder component is mixed with the monomer component, a plastically deformable dough (the actual bone cement) is created by swelling of the polymers of the powder component in the methyl methacrylate and is usually referred to as bone cement dough. As the powder component is mixed with the monomer component, the activator N,N-dimethyl-p-toluidine reacts with dibenzoyl peroxide and forms radicals. The radicals formed initiate the radical polymerisation of the methyl methacrylate. The viscosity of the bone cement dough increases with continued polymerisation of the methyl methacrylate until the dough solidifies.

The monomer used most frequently in polymethyl methacrylate bone cements is methyl methacrylate. Redox initiator systems usually consist of peroxides, accelerators and optionally suitable reducing agents. Radical formation occurs only when all constituents of the redox initiator systems interact. The constituents of the redox initiator system are therefore arranged in the separate starting components such that they cannot trigger radical polymerisation. The starting components are then storage-stable with suitable composition. Only when the two starting components are mixed to form a bone cement dough do the constituents of the redox initiator system, previously stored separately as monomer liquid and powder, react, wherein radicals are formed, which trigger the radical polymerisation of the at least one monomer. The radical polymerisation then leads, with consumption of the monomer, to the formation of polymers, wherein the cement dough cures.

PMMA bone cements can be mixed in suitable mixing beakers with the aid of spatulas by mixing the cement powder with the monomer liquid. In so doing, air bubbles can become trapped in the bone cement dough, which can have a negative effect on the mechanical properties of the cured bone cement.

In order to avoid inclusions of air in the bone cement dough, a large number of vacuum cement mixing systems have been described, wherein the following are mentioned by way of example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

EP 2 730 296 A2 discloses a thixotropic bone cement for vertebroplasty, in which the thixotropic properties are produced with a number of additives. U.S. Pat. No. 3,739,947 A discloses a cartridge system for mixing a cement, in which a liquid container is opened between two pistons and the liquid flows into a cement powder. One aspect with this cartridge system is that it is not suitable for bone cement, since the opening to the cement powder could be closed by premature reaction of the powder with the monomer liquid, and since the content of the cartridge cannot be sterilised after the filling operation. In addition, in the case of that cartridge system, there is always an excess of air in the container for the powder, which could lead to an undesirable formation of bubbles in the bone cement dough.

A development in cement mixing technology is provided by cement mixing systems in which both the cement powder and the monomer liquid are already packaged in separate compartments of the mixing systems and are only mixed with one another in the cement mixing system immediately before the cement application. Closed full-prepacked mixing systems of this kind have been proposed by DE 44 09 610 A1, EP 0 692 229 A1, DE 10 2009 031 178 B3, U.S. Pat. Nos. 5,997,544 A, 6,709,149 B1, DE 698 12 726 T2, EP 0 796 653 A2 and U.S. Pat. No. 5,588,745 A.

Patent DE 10 2009 031 178 B3 discloses a storing and mixing device as full-prepacked mixing system, in which the starting components necessary to produce the bone cement dough are already stored in the storing and mixing device and can be combined and mixed in the storing and mixing device. The storing and mixing device has a two-part discharge piston for closing a cement cartridge. Here, a combination of a gas-permeable sterilisation piston and a gas-impermeable sealing piston is used. This principle of a closed vacuum mixing system is realised in the PALACOS® PRO closed cement mixing system, which is produced and sold by the company Heraeus Medical GmbH.

With use of all previously known full-prepacked mixing systems, the medical user must perform a number of process steps at the devices in a predetermined order in succession until the mixed bone cement dough is produced and can be applied. If the process steps are muddled, this can lead to the failure of the mixing systems and can therefore cause disruptions in the surgical procedure. Costly training of the medical users is therefore necessary in order to avoid user errors.

WO 00/35506 A1 proposes a device in which polymethyl methacrylate bone cement powder is stored in a cartridge, wherein the cement powder fills the entire volume of the cartridge and the gaps between the particles of the cement powder are of a volume corresponding to the volume of the monomer liquid necessary to produce bone cement dough with the cement powder stored in the cartridge. This device is constructed such that the monomer liquid is introduced from above into the cartridge under the action of a vacuum, wherein to this end a vacuum is applied at a vacuum connection on the lower side of the cartridge. The monomer liquid is thus drawn through the cement powder, wherein the air disposed in the gaps between the cement particles is displaced by the monomer liquid. Here, a mechanical mixing of the formed cement dough by means of an agitator is omitted.

One aspect of this system is that cement powders, which swell quickly with the monomer liquid, cannot be mixed with this device, because the quickly swelling cement powder particles form a gel-like barrier once the monomer liquid has penetrated into the cement powder by approximately 1 to 2 cm, and hinder the migration of the monomer liquid through the cement powder as a whole. Conventional cement powders additionally demonstrate the phenomenon that the cement particles are only poorly wetted by methyl methacrylate on account of the different surface energies. The methyl methacrylate thus penetrates the cement powder only relatively slowly. Under the action of a vacuum, it also cannot be ruled out that the monomer liquid might be suctioned off via the vacuum connection once the cement powder has been fully penetrated by the monomer liquid. There would then be insufficient monomer liquid available for the curing by radical polymerisation, or the mixing ratio might be modified undesirably, as could also the consistency of the bone cement. It is also problematic that the air enclosed between the cement powder particles is to be displaced from top to bottom by the monomer liquid, because the air, which is specifically lighter than the monomer liquid, on account of the force of gravity, attempts to migrate upwardly in the cement powder rather than to migrate downwardly in the direction of the vacuum connection.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further exemplary embodiments will be explained hereinafter on the basis of twenty-one schematically illustrated Figures, without hereby limiting the invention.

Figure 1:
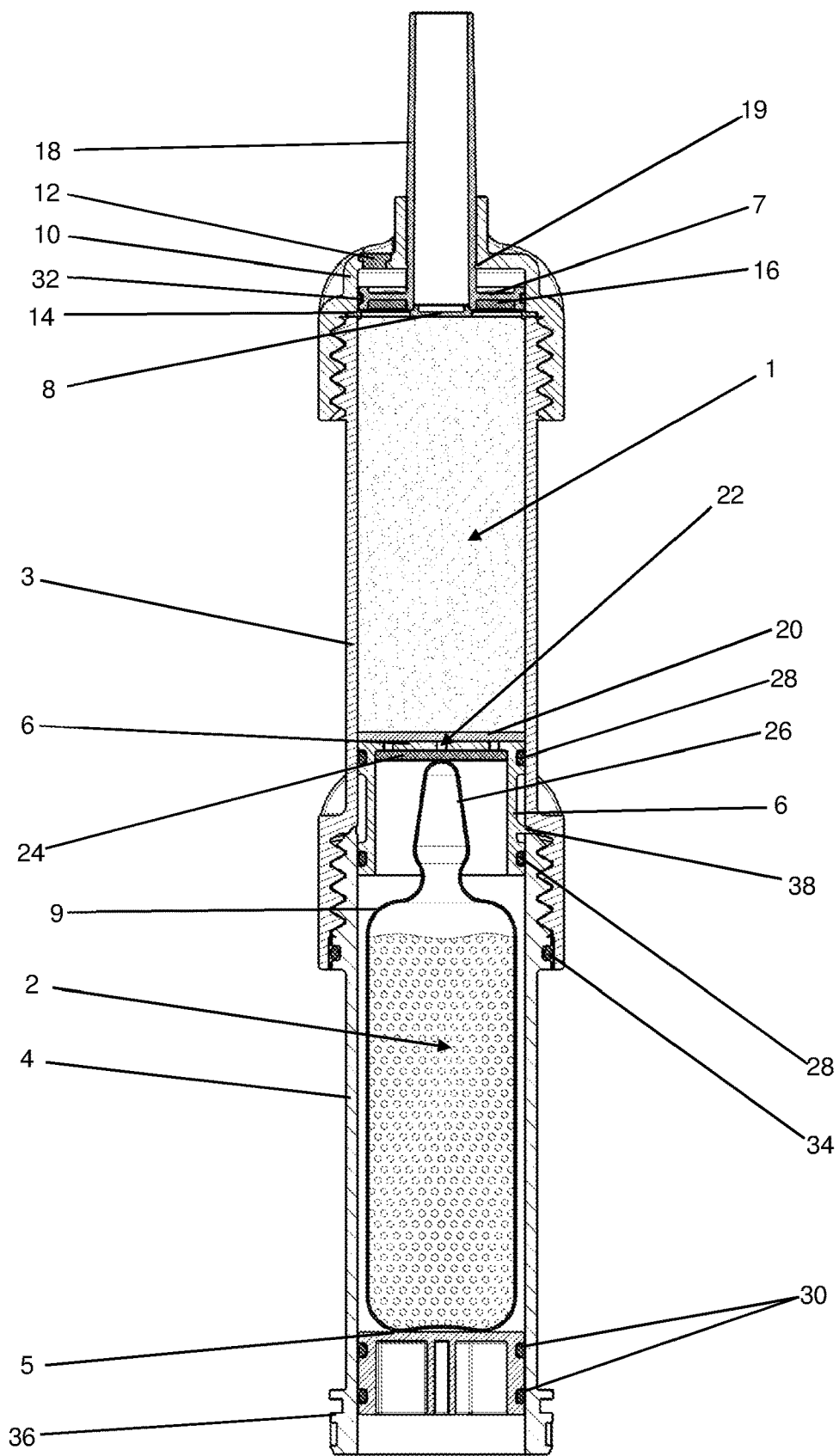
FIG. 1 is a schematic cross-sectional view of a first exemplary device according to one embodiment with two-part cartridge in the starting state.

In the Figures, like reference signs are also used in different exemplary embodiments for like or similar component parts for reasons of clarity and so as to be able to compare the exemplary embodiments.

DETAILED DESCRIPTION

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

One embodiment thus lies in overcoming the disadvantages of the prior art. One embodiment lies in developing a device and a method which are both suitable for mixing and then discharging, and in one embodiment, also storing starting components of a polymethyl methacrylate bone cement. In addition, a method for producing a prepacked PMMA cement cartridge system, which is suitable for mixing and applying a PMMA bone cement dough, will also be provided, with which the problems are overcome. The device shall be driven by a conventional press-out apparatus and shall be as simple as possible with regard to its operation. The structure is to be economical, so that the device can be used just once, for hygiene reasons. As many processes as possible occurring in the device, or all such processes, for example the mixing of the starting components, the discharging of the bone cement dough, and the opening of containers and as applicable of the cartridge, shall be performed with as few process steps as possible and in an automated manner to the greatest possible extent, and one embodiment, shall be driven by means of a single drive.

The device shall contain bone cement powder or a powder containing a bone cement powder and at least one monomer liquid in cavities separated from one another, wherein the monomer liquid shall be arranged, in one embodiment, in a container, so that the monomer liquid can be stored in the device even in the long term. The device or a closure system of the device shall close a cavity, in which the cement powder is stored, in a manner impermeable for powder particles, but permeable for gases, such as the ethylene oxide usual for sterilisation. The cavity used to store the cement powder shall also be used to mix the powder with the monomer liquid. This means that the bone cement dough will be disposed in the cavity following the mixing of the cement components. Where possible, it will not be possible to open the closure system from outside. Contact between the medical user and the polymethyl methacrylate bone cement powder and the monomer liquid shall be ruled out where possible.

One aspect thus lies in developing a device for storing, mixing and discharging polymethyl methacrylate bone cement. The handling of the device shall be simplified to the maximum extent possible so as to avoid, fundamentally, user errors as a result of incorrectly performed assembly steps. The medical user shall connect the device, following removal from a packaging, to a press-out apparatus and shall then actuate this. Additional assembly and process steps shall be avoided as far as possible as a result of the structure of the device. The device shall enable a safe storage of cement powder and monomer liquid in compartments separated from one another, so that, during the storage of the device, an unintentional mixing of the cement components is ruled out. The device shall enable sterilisation with the gas ethylene oxide. The cement powder stored in the device shall be accessible for ethylene oxide. The device shall be activatable with the aid of a manually driven press-out apparatus previously used as standard in an operating theatre, so that, following the positively engaged or frictionally engaged connection of the device to the press-out apparatus, a ram of the press-out apparatus acts on the device by actuation of the press-out apparatus, and activates and drives the device. The monomer liquid shall be mixed without use of a mixer that has to be moved manually from outside.

It shall be possible for the polymethyl methacrylate bone cement powder to be combined and mixed by the medical user with the monomer liquid within the device, without the two starting components coming into contact with the medical user. The device to be developed is in one embodiment a full-prepacked mixing system.

A method shall also be provided, which enables the least complicated use possible of a device of this kind.

A device, which can be economically manufactured and which functions reliably, for mixing a medical bone cement and for storing the starting components of the bone cement as well as a method for mixing the bone cement shall also be provided, with which the simplest manual operation possible can be implemented for the mixing of the starting components.

The first starting component of the polymethyl methacrylate bone cement as mixing material shall be a powder, and the second starting component shall be present in the form of the monomer liquid. The two starting components of the bone cement shall in one embodiment be stored separately in the full-prepacked mixing system and shall be able to be combined reliably by use of the device.

The objects of the embodiments are achieved by a device according to claim 1 and a method for producing a bone cement dough according to claim 21 and a method for producing a prepacked PMMA cement cartridge system, which is suitable for mixing and applying a PMMA bone cement dough, according to claim 29.

Accordingly, the objects of the embodiments are achieved by a device for mixing a polymethyl methacrylate bone cement formed of two starting components and for storing the starting components of the bone cement, the device having a tubular cartridge with a cylindrical interior, wherein a powder is contained as first starting component in a front part of the interior of the cartridge and a container containing a monomer liquid as second starting component is arranged in a rear part of the interior of the cartridge, wherein a discharge piston is arranged between the container and the powder, and wherein a conveying piston is arranged on the side of the container opposite the discharge piston, wherein the discharge piston and the conveying piston are arranged in the interior of the cartridge movably in the longitudinal direction, wherein a conduit means is provided, which connects the front part and the rear part of the interior of the cartridge to one another in a manner permeable for the monomer liquid and for gases, and which is impermeable for the powder.

The interior of the tubular cartridge has a cylindrical geometry or is cylindrical. The cylindrical shape is the simplest shape with which the interior of the cartridge can be produced and is particularly well suited for guiding the movement of the discharge piston and the conveying piston. In addition, the front and the rear part of the interior can be easily sealed outwardly and with respect to one another particularly in any position by the movable pistons if the interior has a cylindrical geometry.

A cylindrical shape is to be understood, geometrically, to mean the shape of a general cylinder having any end-face shape, that is, not only a cylinder having a circular end face. The delimiting inner wall of the interior can thus be a cylinder having any end-face shape, and the lateral surface of the cartridge can also be a cylinder having any end-face shape, as appropriate, in other words also an end face that is not circular or that is not round. In accordance with one embodiment, however, a cylindrical geometry with rotationally symmetrical and for example, circular end face is in one embodiment preferred for the interior of the first cartridge, since these geometries are the simplest to manufacture and it is more difficult for the discharge piston and the conveying piston to become wedged in the interior when they are moved axially in the interior, that is to say moved in the longitudinal direction in the interior. Potential leaks between the inner wall of the interior and the discharge piston and also the inner wall of the interior and the conveying piston during the movement of the pistons are additionally less likely.

The fact that the discharge piston and the conveying piston are axially movable in the cylindrical interior of the cartridge means that they are axially movable along the cylinder axis of the cylindrical interior.

The device according to one embodiment is also suitable and intended for discharging the mixed bone cement dough.

The device according to one embodiment is characterized in that no mixing unit is provided in the front part of the interior. Mixing units, such as mixing blades that can be operated from outside, are usually necessary in order to mix the powder with the monomer liquid. This is not necessary with a device according to one embodiment. The mixing unit can be avoided for example, if a hydrophilic additive is distributed in the powder, with which additive the monomer liquid is also to be distributed in the powder.

The front side of the cartridge is in one embodiment covered in accordance with one embodiment by a cartridge head. The cartridge head is arranged on the side of the front part of the interior opposite the discharge piston. A passageway or an application opening, through which the bone cement dough can be applied, is in one embodiment disposed in the cartridge head.

In accordance with one embodiment, the powder contains a cement powder with which the PMMA bone cement is producible. The powder also contains a hydrophilic additive with which the monomer liquid is to be distributed in the powder. The powder can furthermore also contain radiopacers and/or pharmaceutically active substances, such as antibiotics.

The additive is in one embodiment in particulate or fibrous form. The additive in one embodiment includes a chemical substance with at least one OH group. The additive in one embodiment has an absorption capacity of at least 0.6 g of methyl methacrylate per gram of additive.

It can be provided in accordance with one embodiment that the powder includes at least one particulate polymethyl methacrylate or polymethyl methacrylate copolymer with a sieve fraction of less than 100 μm, an initiator, and at least one particulate or fibrous additive that is insoluble in methyl methacrylate, wherein the additive has an absorption capacity of greater than or equal to 0.6 g of methyl methacrylate per gram of additive at room temperature.

A powder of this kind is particularly well suited for distributing the monomer liquid in the powder, and therefore the device can be provided with a structure with which the monomer liquid is pressable in from one side, even on a narrow side of the front part of the interior of the cartridge. Here, it has surprisingly been found that, by simply bringing a powder of this kind and for example, a powder as defined hereinafter into contact with a monomer liquid, for example, with a monomer liquid as defined hereinafter, it is possible to produce a tack-free, plastically deformable bone cement dough which cures independently by radical polymerisation, without the need to mix the cement dough manually or with the help of technical aids. It has been observed that, by adding a particulate or fibrous additive which is insoluble in methyl methacrylate and which has an absorption capacity of more than 0.6 g of methyl methacrylate per gram of additive at room temperature to form a cement powder of a low-viscous bone cement, a modified powder is obtained as cement powder, into which monomer liquid is pressable over a distance of at least 5 cm. The additive surprisingly also improves the wetting of the cement powder with monomer liquid. Here, the additive has a "wick effect" and conducts the monomer liquid into the powder already in very small amounts from 0.1% by weight. The additive also delays the clumping of the polymer particles in the powder, whereby the formation of a blocking gel layer is delayed and the infiltration of the monomer liquid into the powder is promoted. Here, the monomer liquid is pressable into the powder or also sucked into the powder.

Here, it can in one embodiment be provided that the additive has covalently bonded hydroxyl groups at its surface. The additive, in accordance with one embodiment, can be selected in one embodiment from the group consisting of microcrystalline cellulose, oxycellulose, starch, titanium dioxide and silicon dioxide, wherein pyrogenic silicon dioxide is preferred in one embodiment. The additive can have a particle size of the sieve fraction less than 100 μm, in one embodiment of the sieve fraction less than 50 μm, and in one embodiment of the sieve fraction less than 10 μm. It can also in one embodiment be provided that the additive is contained in the powder in an amount of from 0.1 to 2.5% by weight relative to the total weight of the powder. It can furthermore be provided that the polymer powder contains dibenzoyl peroxide as initiator.

It can be provided that the monomer liquid contains at least one methyl methacrylate and an activator. Furthermore, it can be provided that the monomer liquid contains at least one activator from the group of aromatic amines. It can also be provided that the monomer liquid contains at least one radical stabiliser from the group of quinones or sterically hindered phenols.

It is advantageous one embodiment if the additive has covalently bonded hydroxyl groups at its surface. Here, Si—OH groups and alcohol OH groups for example, are particularly advantageous in one embodiment. Due to the OH groups arranged at the surface, the additive has a high surface energy, whereby a good wettability of the additive with methyl methacrylate is achieved. The pyrogenic silicas Aerosil® 380 and Aerosil® 300 are particularly suitable. In addition, it is also possible to use silicon dioxide produced by sol-gel processes as additive.

It is also possible to arrange two or more containers in the front part of the interior of the cartridge, depending on the necessary volume of monomer liquid.

The discharge piston is a piston movable axially in the interior of the cartridge, with which piston a bone cement dough is drivable out from the cartridge from the front part of the interior. The bone cement dough is produced by mixing the monomer liquid with the powder.

It can be provided that at least one feedthrough is provided in the discharge piston and/or between the discharge piston and the inner wall of the interior as conduit means, by which the front part of the interior and the rear part of the interior are connected to one another. Here, a filter impermeable for the powder and permeable for the monomer liquid and gases can be arranged in or on the at least one feedthrough.

It is hereby achieved that the monomer liquid within the closed interior of the cartridge is transferrable from the rear part of the interior into the front part of the interior, in which the powder is disposed, by pushing the conveying piston in the direction of the discharge piston.

Alternatively, the conduit means can also be a line or a plurality of lines, which is or are arranged externally on the cartridge or in the cartridge wall and which connects or connect the front part of the interior to the rear part of the interior of the cartridge by feedthroughs in the cartridge wall or by openings. In this case, the discharge piston is bypassed. The monomer liquid in this case is pushable through these lines from the rear into the front part of the interior, and gas, such as ethylene oxide, can flow through these lines from the front into the rear part of the interior (or vice versa).

It can in one embodiment be provided that the at least one feedthrough is covered by a filter which is impermeable for powder, but permeable for the monomer liquid. Such filters are also referred to as pore filters. The powder can thus be prevented from passing into the rear part of the interior, and therefore a premature reaction of the powder with the monomer liquid can be prevented. The filter impermeable for the powder and permeable for the monomer liquid is in one embodiment arranged between the discharge piston and the powder, so that the powder does not enter the at least one feedthrough and this feedthrough does not become clogged following a premature reaction with the monomer liquid.

It can furthermore be provided that, by advancing the conveying piston in the direction of the discharge piston, the container is openable, the monomer liquid is pressable into the powder, and the discharge piston is then pushable by means of the conveying piston in the direction of the front side of the cartridge.

It is hereby achieved that all process steps necessary for the mixing and discharging of the bone cement can be driven already by a unidirectional movement of the conveying piston alone. It is thus sufficient to allow a linear drive to act on the conveying piston in order to drive or perform all processes, such as the opening of the container, the pressing of the monomer liquid into the powder, and the discharging of the bone cement dough, mixed from the powder and the monomer liquid, from the cartridge. A very simple device is hereby provided, with which a bone cement can be produced and applied and at the same time the starting components of the bone cement, specifically the powder containing a cement powder and the monomer liquid, can be stored. The front side of the cartridge is opposite the cartridge base.

Here, it can be provided that by pushing the conveying piston in the direction of the front side of the cartridge, the discharge piston is pressable in the direction of the cartridge head and by this the bone cement dough produced in the front part of the interior from the powder and the monomer liquid is thus pressable out through an opening.

It is hereby achieved in a simple manner that the bone cement dough is drivable out from the cartridge using the same drive also used to open the container and to press in the monomer liquid, specifically using the unidirectionally driven conveying piston.

In accordance with one embodiment, it can be provided that the container for the monomer liquid is a glass ampoule or plastic ampoule, which is breakable open by a movement of the conveying piston, or the container for the monomer liquid is a film bag, which is rippable, pierceable or slittable by the movement of the conveying piston.

One advantage of this is that the monomer liquid can be stored in the device in containers of this kind over a particularly long period of time. For the same purpose, it can be provided that the film bag is coated with a metal coating, for example, with aluminium. The container is in one embodiment a glass ampoule, since the monomer liquid can be stored for a particularly long time in glass ampoules.

It can also be provided that a detent means is arranged on the discharge piston, so that the discharge piston can latch with the cartridge between the front and the rear part of the interior, wherein this latching cannot be released by the forces occurring as the container is opened and a pressure exerted onto the monomer liquid by the conveying piston, but is releasable by a pressure acting on the discharge piston directly from the conveying piston.

Here, it is assumed that the conveying piston is driven by a conventional press-out apparatus having a ram that can be advanced forward, and that no abnormal pressure shocks are exerted onto the conveying piston which could be transferred to the discharge piston in the form of shocks via the monomer liquid. In the event of a shock of this kind, the discharge piston could become detached from the interior. As a result of the measure according to one embodiment, it is achieved that, first, the container is openable by advancing the conveying piston, and the monomer liquid running out is then pressable by means of the conveying piston into the front part of the interior of the cartridge, that is, into the powder, wherein the discharge piston retains its position relative to the cartridge and relative to the interior. Only once the monomer liquid has been largely pressed into the powder, and therefore the bone cement dough is present in the front part of the interior of the cartridge, can the bone cement dough then be pushed by means of the discharge piston from the front part of the cartridge as a result of the conveying piston pushing directly on the discharge piston (that is to say apart from any solids remaining therebetween, such as container parts or filling material), and driving the discharge piston. The force to release the latching is thus greater than the force necessary to open and, if necessary, also destroy the container of the monomer liquid. The destruction of the container can be expedient for example if the container is a glass ampoule that has to be largely compressed and thus shattered in order to sufficiently significantly reduce its volume for the press-out operation. This means that the entire container for the monomer liquid is compressed by the axial movement of the conveying piston, wherein at the same time the monomer liquid is pressed into the front part of the interior of the cartridge or into the powder, and the detent element of the discharge piston is only then released by the pressure of the conveying piston on the discharge piston, and the discharge piston presses the formed bone cement dough in the direction of the front side of the cartridge or the discharge opening. The detent means can be omitted if a plastic bag is used as a container for the monomer liquid.

It can also be provided that the cartridge is composed of a front cartridge part and a rear cartridge part, which are fixedly connected to one another, for example, screwed to one another, wherein a cartridge head is in one embodiment fastened to the front cartridge part.

Here, in one embodiment, the front part of the interior of the cartridge is delimited by the front cartridge part and the cartridge head or possibly by the head part and the front cartridge part, and that the rear part of the interior, in which the container for the monomer liquid is arranged, is delimited by the rear cartridge part and the cartridge base or the conveying piston.

Since the cartridge is composed of two or three parts, the assembly of the device and also the filling of the cartridge with the powder and with the container containing the monomer liquid is simplified. Production costs can thus also be saved.

The two cartridge parts and as applicable the head part are in one embodiment sealed with respect to one another by peripheral seals in order to prevent an escape of the powder, of the monomer liquid exiting from the open container, and of the bone cement dough at the connections.

In accordance with one embodiment, it can be provided that at least one filling material is arranged in the rear part of the interior next to the container, for example, that at least one filling material is arranged in a region between the container and the discharge piston, wherein the filling material is in one embodiment a foam material and/or is formed by plastic beads.

The filling material is used to displace the monomer liquid flowing out from the container. The free volume in the rear part of the interior or between the container and the discharge piston is thus reduced by the filling material. This free volume must be filled with the monomer liquid and remains in the rear part of the interior of the cartridge once the monomer liquid has been pressed out. Due to the reduction of the free volume in this region, a smaller amount of the monomer liquid can thus be used. This is desirable for cost reasons and on account of the chemical properties of the monomer liquid. The use of a foam material is preferred in one embodiment with use of a glass ampoule as container for the monomer liquid, since the glass splinters produced as the glass ampoule is opened by the conveying piston is pushable into the foam material and the movement of the conveying piston is then not blocked.

In one embodiment, a foam material ring is used as filling material, which is arranged around a head of a glass ampoule as container for the monomer liquid in the free volume between the glass ampoule and the discharge piston. A foam material ring, but also another foam material as filling material can additionally also be used as a transport protection for the glass ampoule. Alternatively, mechanically deformable spacers formed from resilient plastic can also be used as transport protection.

In one embodiment a mesh, a sieve or a splinter shield is arranged between the powder and the container for the monomer liquid, in one embodiment between the discharge piston and the container, or is arranged in feedthroughs in or on the discharge piston.

The mesh, the sieve or the splinter shield for this purpose is arrangable between the discharge piston and the container or between the discharge piston and the powder or in the at least one opening of the discharge piston or in the at least one opening between the discharge piston and the inner wall of the interior.

Broken pieces of the container or fragments of the container are retainable by the mesh, the sieve or the splinter shield. A contamination of the bone cement dough with the material of the container for the monomer liquid is hereby prevented.

It can furthermore be provided that the conveying piston closes the interior of the cartridge at the cartridge base, for example, in a pressure-tight and liquid-tight manner.

It is thus achieved that the monomer liquid, when pressed into the powder, cannot escape at the rear side of the cartridge. For this purpose, two peripheral seals are used for example, which seal off the discharge piston with respect to the inner wall of the cartridge. For example, the seals can be made of rubber.

It can also be provided that the discharge piston is sealed off with respect to the inner wall of the interior of the cartridge. Peripheral seals made of rubber can be used for this purpose as well.

In one embodiment, the discharge piston is formed as a perforated plate or as a mesh screen and at least one open-pored plastic layer which is gas-permeable, but impermeable for powder particles closes the holes or the mesh openings in a manner that is gas-permeable and impermeable for powder particles.

It is thus achieved that particles of the powder cannot pass into the rear part of the interior and react there prematurely with the monomer liquid.

In accordance with a development, it can also be provided that at least one opening aid for opening the container for the monomer liquid is arranged on the side of the discharge piston facing towards the container, wherein the at least one opening aid is in one embodiment at least one sharp-edged blade or at least one pin.

The container can hereby be opened in a simple way and with a defined application of force by the conveying piston.

In one embodiment, the volume of the monomer liquid in the container is at least as large as the volume of the gaps filled with air between the powder particles in the front part of the interior, in one embodiment is at least as large or exactly the same size as the volume of the gaps filled with air between the powder particles in the front part of the interior and the rear part of the interior when the conveying piston bears against the discharge piston, minus the volume of the material of the container and, as applicable, the volume of filling material in the rear part of the interior.

It is thus ensured that the correct amount of monomer liquid in order to produce a bone cement of the desired consistency is held ready in the device. It is thus ensured that all of the powder is wetted with the necessary volume of monomer liquid and that a homogeneous cement dough can be produced.

The expression "exactly the same size as", in this context, in one embodiment means within a deviation of at most 10%.

It can also be provided that the volume of the front part of the interior is at least equal to the total volume of the powder particles and the monomer liquid to be ejected from the rear part of the interior.

It can also be provided that a receiver for excess monomer liquid is provided at the front end of the cartridge or in a cartridge head at the front side of the cartridge, wherein the powder cannot infiltrate the receiver, wherein the receiver is in one embodiment a hydrophilic spongy structure.

It is thus achieved that the bone cement dough reaches the desired consistency and does not contain too much monomer liquid. Monomer liquid can thus be used in slight excess in order to compensate for uncertainties with regard to the amount of monomer liquid introduced into the powder.

It can also be provided that the powder is pressed into the front part of the interior, in one embodiment is under pressure in the front part of the interior.

It can be provided that the gaps between the cement particles of the powder account for between 25 volume % and 40 volume % of the pressed-in powder.

Due to the pressing-in of the powder, the powder particles are arranged so densely that a hydrophilic additive distributed in the powder conducts and distributes the monomer liquid in the powder, even in low concentration, so that it is sufficient if the monomer liquid is pressed into the powder only from one side.

In one embodiment, it can also be provided that a ventilation opening is arranged in the wall of the cartridge directly above the conveying piston and connects the rear part of the interior to the surrounding atmosphere.

This ventilation opening is closed by the conveying piston as soon as the conveying piston has been moved sufficiently far in the direction of the discharge piston. The ventilation opening is in one embodiment closed before the container for the monomer liquid is opened by the movement of the conveying piston, so as to prevent the monomer liquid from escaping from the rear part of the interior. The interior and the content of the cartridge can be sterilised with ethylene oxide with the aid of the ventilation opening. The ethylene oxide is introducible into the cartridge on the one hand via the cartridge head and on the other hand through the ventilation opening.

It can also be provided that a connection element is provided on the rear side of the cartridge, with which connection element the device is connectable to a press-out apparatus. The press-out apparatus has a ram that is advanceable forward or a rod that is advanceable forward, with which the conveying piston is drivable in the interior of the cartridge in the direction of the front side of the cartridge.

It can furthermore be provided that a discharge tube is arranged on the front side of the cartridge, as applicable on the cartridge head, by means of which discharge tube the bone cement dough is applicable.

In one embodiment, a multi-part closure system including a discharge opening is arranged on a cartridge head arranged at the front side of the cartridge, wherein at least two parts of the closure system are movable relative to one another, driven by a movement of the mixed bone cement dough, and the discharge opening opens as a result of this movement of the at least two parts of the closure system relative to one another, and wherein the movement of the mixed bone cement dough is drivable by a pressure of the discharge piston on the bone cement dough, wherein in one embodiment part of the closure system, for example, a stopper, includes a connection between the front part of the interior of the cartridge and the surrounding environment of the device, which connection is permeable for gases, but is impermeable for the powder and the monomer liquid.

The cartridge or the interior of the cartridge can be closed hereby, so that no powder can pass outwardly. The device is thus better suited for the storage of the starting components. At the same time, the closure system is openable by driving the discharge piston, so that no additional drive is necessary to open the closure. By means of one embodiment, it can be ensured that the content of the device and therefore of the monomer liquid container and particularly the powder can be sterilised from outside with the aid of a sterilising gas, such as ethylene oxide.

Here, it can be provided that the bone cement dough is then dischargeable through the opened discharge opening with the same pressure on the bone cement dough as that exerted in order to open the closure system.

It is thus sufficient to equip the device with just one drive, with which the closure system is openable and the finished bone cement dough is drivable out from the cartridge, and the mixing of the starting components and the opening of the container can also be driven.

In devices of this type it can also be provided that the closure system has a wall with the discharge opening and a stopper, wherein the discharge opening is connected to the surrounding environment of the cartridge and the stopper closes the discharge opening when the cartridge is closed, wherein either the wall with the discharge opening is movable by the pressure of the bone cement dough and the stopper is fixed relative to the cartridge, or the stopper is movable by the pressure of the bone cement dough and the wall is fixed or fixable relative to the cartridge.

The stopper and the wall then form the two or the at least two parts of the closure system. A closure system is hereby provided which can be realised easily and economically, and which is relatively unsusceptible to malfunctions. In addition, the force that is used to drive out the bone cement dough can also be effectively used with a closure system of this type in order to open the cartridge.

It can furthermore be provided that a discharge tube with the discharge opening is mounted movably relative to the cartridge, wherein a stopper which closes the discharge tube is fixedly connected to the cartridge and the discharge tube is movable relative to the stopper by the pressure on the bone cement dough and thus is openable.

Here, it can again be provided that the discharge tube is pushable in a direction away from the cartridge base by a pressure on the side of the bone cement dough facing towards the cartridge base, and in so doing the stopper is released from the discharge tube and thus opens the cartridge.

By both measures, a device that can be used particularly well is provided, which device has the advantage that the user can clearly see from outside, on the basis of the movement of the discharge tube, that the device is ready for use and that a discharge of the bone cement dough from the discharge tube is imminent. The latter can also be identified on the basis of the fact that the movement of the discharge tube has ended again. The discharge tube and the stopper are parts of the closure system in these cases. A simple closure system that is unsusceptible to disruptions can thus be constructed, in which closure system the stopper does not fall out from the device. Thus, no part of the closure system detaches from the device.

It can also be provided that the closure system includes a wall which is gas-permeable, but impermeable for powder and liquids, wherein the wall is arranged in the cartridge in such a way that the pressure of the bone cement dough acts on the wall, and thus moves a stopper or a cover with the wall relative to the cartridge and thus opens the cartridge, or thus moves a discharge opening with the wall relative to the cartridge and thus removes a stopper, which is fixedly connected to the cartridge, from the discharge opening, wherein the wall in one embodiment includes a plate with pores.

As a result of this structure, the interior of the cartridge can be sterilised with a sterilising gas, such as ethylene oxide, prior to the use of the device by evacuating air from the interior of the cartridge and then feeding in the sterilising gas, even if the closure system is closed.

It can furthermore be provided that a hydrophilic additive is distributed in the powder, with which additive the monomer liquid is distributable throughout the powder, in one embodiment without a polymerisation of the bone cement beforehand preventing the further distribution of the monomer liquid in the powder.

The monomer liquid can hereby be quickly distributed in the powder before any polymerisation of the cement powder contained in the powder with the monomer liquid takes place and further distribution of the monomer liquid is suppressed. Only hereby is the structure according to one embodiment actually possible, specifically the fact that the monomer liquid is pressed into the powder from one side and can nevertheless be distributed throughout the powder before the polymerisation suppresses any further distribution of the monomer liquid in the powder.

In one embodiment, it can be provided that the front part of the interior of the cartridge is connected to the surrounding environment of the device by means of a connection which is permeable for gases, but impermeable for the powder and for the monomer liquid, wherein the connection is in one embodiment arranged in a closure system or a stopper for closing a discharge opening.

The content of the device can thus be sterilised with the aid of a sterilising gas, such as ethylene oxide, without the powder or the monomer liquid being able to escape during the application of the gas. If the connection permeable for gas and impermeable for powder and monomer liquid is provided as part of the closure system, the discharge opening can at the same time also be used to gas the content of the cartridge. In addition, no additional opening needs to be provided in the cartridge.

The objects addressed by the present embodiments are also achieved by a method for mixing and applying a bone cement with a device of this kind, including the steps of pushing the conveying piston in the direction of a cartridge head, which is arranged at the front side of the cartridge, opening the container by the movement of the conveying piston in the interior of the cartridge, then pressing the monomer liquid into the powder, and thus forming a bone cement dough, and then pushing the discharge piston in the direction of the cartridge head, thereby driving the bone cement dough out from the cartridge through the cartridge head by the movement of the discharge piston.

Besides the monomer liquid, air contained in the rear part of the interior of the cartridge is also pushed from the rear part of the interior into the front part of the cartridge. The air contained between the powder particles in the front part of the interior of the cartridge is also displaced from the front part of the cartridge by the infiltrating monomer liquid. The air can escape outwardly through a filter that is impermeable for the powder, but permeable for gases, so that no overpressure is built up in the front part of the interior by the air.

The bone cement dough is formed by the wetting of cement powder particles contained in the powder with the monomer liquid. The cement powder particles then swell up as a result of the monomer liquid, and radical polymerisation of the monomer liquid is triggered by a reaction of the accelerator with the initiator. The accelerator and the initiator are part of the powder-monomer liquid system. The bone cement dough is formed by these chemical reactions.

It can be provided in accordance with one embodiment that the bone cement dough is mixed without the application of shear forces. This can be achieved with the aid of the powder with the additive.

It can be provided in accordance with one embodiment that the mass of the monomer liquid transferred into the powder is between 1.5 and 2.5 times greater than the mass of the powder.

In order to obtain the desired mixing ratio between powder and monomer liquid in the bone cement dough, it can be provided in accordance with one embodiment that excess monomer liquid is received at the front side of the cartridge between a porous filter of the wall and a cartridge head. The monomer liquid is for this purpose pushed through the porous filter, which is impermeable for the powder and the bone cement dough. By receiving the excess monomer liquid once the monomer liquid has passed through the powder as far as the wall, it is possible to prevent the bone cement dough from becoming too runny and thus reaching an undesirable consistency. In addition, in order to avoid a consistency of the bone cement dough that is too thick, it can be provided that the monomer liquid is present in excess in order to compensate for the losses by the residues of the monomer liquid remaining between the discharge piston and the conveying piston and also in the passageways of the discharge piston.

It can be provided that the discharge piston is latched with the inner wall of the cartridge as the container is opened and as the monomer liquid is pressed into the powder, wherein the latching of the discharge piston with the inner wall of the cartridge is released by the pressure of the conveying piston on the discharge piston, and the conveying piston then pushes the discharge piston in the direction of the cartridge head.

It can thus be ensured that the container for the monomer liquid is first opened and the monomer liquid is then pressed fully or at least in the desired amount into the powder, before the discharge piston is pushed by the conveying piston in the direction of the cartridge head in order to press the bone cement dough out from the cartridge.

It can also be provided that the device is inserted into a press-out apparatus and that a ram of the press-out apparatus is advanced forwards, by means of which ram the conveying piston is driven in the direction of the cartridge head.

In accordance with a development it can be provided that the monomer liquid is distributed in the powder with the aid of a hydrophilic additive, wherein the powder is in one embodiment compressed or contained under a mechanical pressure in the front part of the interior.

It can be provided in accordance with one embodiment that the powder is pressed into the front part of the interior of the cartridge, wherein the front part of the interior of the cartridge is in one embodiment closed in such a way that the powder in the front part of the interior is under a mechanical pressure and is thus held compressed. The mechanical pressure is maintained by the cartridge, the discharge piston and the cartridge head, which are thus stressed. The force to apply the pressure is thus applied by the resilience or a resilient deformation of the cartridge, the discharge piston, and the cartridge head.

It can furthermore be provided that the container is compressed by the movement of the conveying piston and is in one embodiment destroyed as a result.

If the container is a glass ampoule or a plastic ampoule it is in one embodiment shattered.

In accordance with a development of the method according to one embodiment it can be provided that a discharge opening on the cartridge head is firstly closed with the aid of a closure system, wherein the closure system is opened by the pressure exerted onto the bone cement dough by the conveying piston and via the discharge piston, wherein the bone cement dough is then pressed out through the discharge opening with the same pressure.

The discharge opening is in one embodiment realized by a discharge tube.

Here, it can be provided that part of the closure system is a stopper, which closes the discharge opening, wherein the stopper is pushed out from the discharge opening with the cement dough, or a wall with respect to the cartridge with the discharge opening is pushed by the bone cement dough in the direction of the front side of the cartridge, thus releasing a stopper or a cover, which is fixed to the cartridge, from the discharge opening.

The wall is in one embodiment axially movable in the interior of the cartridge.

The objects to be achieved by the embodiments are also achieved by a method for producing a prepacked PMMA cement cartridge system which is suitable for mixing and applying a PMMA bone cement dough and in which a powder is stored as a starting component of the bone cement, the method having the following steps:

A) providing a cartridge having a cylindrical interior and a discharge piston having an external periphery matching the cylindrical interior, B) filling the powder into the interior of the cartridge, wherein the powder includes a cement powder as main component for producing the PMMA bone cement dough, and the powder additionally includes a hydrophilic additive, which is distributed in the cement powder, C) compressing the powder in the interior of the cartridge between the discharge piston and a wall, which delimits the cylindrical interior on a front side, by reducing the distance between the discharge piston and the wall in the interior, D) locking, supporting or fastening the wall and/or the discharge piston, so that, during the storage of the powder, a mechanical pressure is exerted onto the powder by the wall and the discharge piston, and the powder remains compacted.

When compressing the powder, the powder is pressed together and in so doing the mean distance of the powder particles from one another is reduced. The particles can also be resiliently deformed during this process.

Here, it can be provided that the discharge piston is held against the cartridge by means of a press fit, a detent means and/or by being supported, and the wall is embodied in one part with the cartridge or the wall bears against the inner face of the cartridge, or the wall is held in the cartridge by being locked or by a press fit.

It can furthermore be provided that at least one container containing a monomer liquid as further starting component of the bone cement is arranged in the interior of the cartridge, and a conveying piston is arranged at the cartridge base of the cartridge, wherein the at least one container is arranged between the conveying piston and the discharge piston, and a filling material, for example, at least one foam material body and/or plastic grains, is additionally arranged in one embodiment in the rear part of the interior of the cartridge, in which the at least one container is arranged.

It can also be provided that the discharge piston is supported by the at least one container and by the conveying piston arranged at the cartridge base in the interior of the cartridge.

One embodiment is based on the surprising finding that it is possible to use a linear drive, as provided by a conventional press-out apparatus with linearly advanced ram, to mix together the starting components stored separately from one another, specifically the monomer liquid and the powder containing the cement powder, and to then discharge the bone cement dough thus mixed from the device. The use of the device is hereby simplified to the maximum. In addition, a closure system used to close the interior of the cartridge, in which the powder is contained, is also openable using the same drive. All process steps are in one embodiment performed with just one continued application of force. By means of a hydrophilic additive distributed in the powder and/or by means of the use of a compressed powder, the monomer liquid is well distributable in the powder, even if pressed into the powder over a small area, without the swelling bone cement dough preventing any further distribution of the monomer liquid in the powder.

One embodiment is based on the idea of utilising the known linear forward movement of rams of manually operated press-out apparatuses so that a container for the monomer liquid is first opened by a continuous application of the compressive force of the linear forward movement of the ram, and the container is then compressed, whereby the monomer liquid exits the container and is pressed into a compacted cement powder, wherein the air provided between the cement powder particles is displaced by the pressed-in monomer liquid and a cement dough is produced once the cement powder particles have been wetted by the monomer liquid. A precondition for this is the use of a cement powder that is designed such that it is wetted very effectively by the monomer liquid and can absorb the liquid by means of a capillary effect.

The idea of the device lies in arranging at least the container for the monomer liquid behind a reservoir of the powder containing the cement powder, such that the axially movable conveying piston is arranged behind the container and the discharge piston permeable only for liquids and gases is arranged between the container and the reservoir for the cement powder. An axially movable sterilisation piston (a movable wall with a filter that is impermeable for the powder, but permeable for the gases) which is permeable only for gases and liquids can be arranged in front of the reservoir of the cement powder. The sterilisation piston is connected to a discharge tube.

A discharge opening is in one embodiment closed in a first embodiment by means of a stopper which is not axially movable and which is connected to the cartridge by means of ribs. The radial ribs are connected to a ring, and this either can be clamped between the cartridge head and the cartridge, or alternatively the ring can be wedged with the cartridge. Here, the ring has a slightly greater outer diameter than the inner diameter of the cartridge. Once the cement powder has been mixed with the monomer liquid, the cement dough shifts the sterilisation piston or the wall in the direction of the cartridge head as a result of the linear forward movement of the discharge piston. The discharge tube is thus removed from the stopper, and the discharge opening is released, and the formed cement dough is pressable outwardly through the opened discharge tube.

In one embodiment, the discharge tube is closed by an axially displaceable stopper, which is arranged in the discharge tube. The axially displaceable piston in the discharge tube forms, together with the wall, a closure system of the cartridge to be opened by axial pressure. This means that the cement dough produced following the mixing of the monomer liquid with the cement powder pushes the stopper out from the discharge tube. The discharge tube is thus free, and the cement dough can be expelled by the axial movement of the conveying piston and the discharge piston, and can be applied.

In accordance with one embodiment, an open-pored plastic layer, which is gas-permeable, but impermeable for powder particles is arranged in the sterilisation piston or in the wall and connects the upper side of the sterilisation piston to the lower side of the sterilisation piston in a gas-permeable manner, wherein the plastic layer is in one embodiment formed as a plate. The gas ethylene oxide can pass through the feedthrough of the cartridge head to the sterilisation piston for sterilisation and can then enter the front part of the interior of the cartridge through the open-pored plastic layer and can sterilise the cement powder. By means of the open-pored plastic layer of the sterilisation piston which is impermeable for particles, or by means of the wall or the seal, particles of the powder are prevented from passing through the outlet from the front part of the interior during the sterilisation and the storage and also transport of the device. Once the sterilisation has been performed, the ethylene oxide, during the degassing, can escape into the surrounding environment from the interior through the open-pored plastic layer of the sterilisation piston or the wall or the seal and, as applicable, a feedthrough in the cartridge head.

One advantage of the device according to one embodiment lies in the simplified handling. The user only has to connect the device filled with powder and monomer liquid to a manual press-out apparatus in a first step and actuate the press-out apparatus pointing upwardly with the cartridge head in a second step until the cement dough exits from the discharge tube. The cement dough can then be pressed out by further actuation of the press-out apparatus, as is the case in previously conventional mixing systems. The mixing system or the device is a full-prepacked mixing system, which can be used, with use of a suitable cement powder, as a ready-to-use system.

Complex assembly steps and manual mixing with mixing rods with mixing elements secured thereto are no longer necessary, in contrast to the previously full-prepacked mixing systems. User errors caused by incorrect assembly steps and by incorrect manual mixing are thus eliminated as a result of the design.

It is advantageous in one embodiment if at least one opening aid for opening the container for the monomer liquid is arranged on the side of the discharge piston facing towards the cartridge base, wherein the opening aid is in one embodiment constituted by sharp-edged blades or pins. The opening of the monomer liquid container is thus facilitated.

An exemplary device for storing, mixing and discharging polymethyl methacrylate bone cement is composed of a) a hollow-cylindrical cartridge with a connection element arranged at the cartridge end for connecting the cartridge to a press-out apparatus, b) a cartridge head, which closes off the hollow-cylindrical cartridge, wherein a feedthrough for receiving the discharge tube is arranged in the cartridge head, and wherein at least one feedthrough connects the outside of the cartridge head to the inside of the cartridge head in a gas-permeable manner, c) a discharge tube, d) a sterilisation piston (in the form of a wall), which is axially movable in the cartridge head and which is gas-permeable, but impermeable for powder particles, wherein the sterilisation piston or the wall has a feedthrough which is connected on the upper side to the discharge tube in a liquid-permeable manner, e) a closure of the discharge tube which is to be opened by application of an axial pressure and which closes the discharge tube for cement powder particles, f) a conveying piston, which is arranged axially movably in the cartridge and which closes the cartridge base in a liquid-impermeable manner, g) a discharge piston, which is arranged in the cartridge in a manner axially movable between the sterilisation piston and the conveying piston, wherein the discharge piston has at least one feedthrough, which is liquid-permeable and impermeable for powder particles, between the two end faces, h) at least one monomer liquid container, i) a rear cavity for storing the monomer liquid container, which is delimited by the inner wall of the cartridge, the conveying piston, and the discharge piston, j) a powder containing a cement powder, and k) a front cavity, in which the powder is arranged, wherein the front cavity is delimited by the inner wall of the cartridge, the sterilisation piston and the discharge piston.

Here, the feedthrough in the sterilisation piston forms the discharge opening in the wall in the sense of the present embodiment.

By way of example, a method according to one embodiment for mixing the powder with the monomer liquid so as to form bone cement dough can be carried out with a device of this kind, with the following successive steps:

a) connecting a press-out apparatus to the connection element of the cartridge, b) advancing a ram of the press-out apparatus, c) displacing the conveying piston in the direction of the cartridge head, d) compressing the at least one container for the monomer liquid between the conveying piston and the discharge piston, e) breaking open the container, f) compressing the container and pressing out the air from the rear cavity and pressing out the monomer liquid by means of the conveying piston through the at least one feedthrough of the discharge piston into the powder in the front cavity, g) spreading the monomer liquid through the powder while simultaneously displacing the air from the gaps between the powder particles, h) wetting the cement powder particles with the monomer liquid, i) allowing the air from the powder to escape through the sterilisation piston or the wall, j) swelling the cement powder particles by the monomer liquid and triggering radical polymerisation of the monomer liquid by reaction of the accelerator with the initiator, k) forming the cement dough from the cement powder and the monomer liquid, l) opening the closure at the discharge opening by application of axial pressure by means of the cement dough pressed axially in the direction of the cartridge head, and m) pressing out the cement dough through the discharge tube as a result of the forward movement of the conveying piston and the discharge piston.

In order to determine the absorption capacity of the additives, an Enslin apparatus known from the field of pharmacy (C.-D. Herzfeldt, J. Kreuter (Hrsg.): Grundlagen der Arzneiformenlehre. Galenik 2, Springer Verlag Berlin Heidelberg New York, 1999, p. 79-80.) was simplified. A 1D3 glass filter crucible from the company Schott was used. The tare weight of the glass filter crucible was first determined. Then, 3,000 g and 1,000 g of the additive were weighed into separate glass filter crucibles. The glass filter crucibles were each fitted to a suction flask. 20 ml of methyl methacrylate were added to the additive, so that the additive was fully covered. The methyl methacrylate not absorbed by the additive ran down through the glass filter crucible. After 15 minutes, the glass filter crucibles with the additive and the absorbed methyl methacrylate were weighed and the mass of the absorbed methyl methacrylate was determined. The determination was repeated three times in each case, and the mean value was determined. The glass filter crucible was treated in the same manner with methyl methacrylate without added additive as reference.

Example 1: Determination of the Absorption Capacity of the Additive

The following starting materials were used to determine the absorption capacity of the additive:
methyl methacrylate (Sigma-Aldrich)
starch (Sigma-Aldrich, sieve fraction <100 μm)
cellulose (Sigma-Aldrich, sieve fraction <100 μm)
Aerosil® 380 (Evonik, particle size ~7 nm)

In order to determine the absorption capacity of the additives constituted by starch, cellulose and Aerosil®380, a 1D3 glass filter crucible from the company Schott Mainz was used. The tare weight of the glass filter crucible was first determined. Then, 3,000 g and, in the case of Aerosil®, 1,000 g of the additive were weighed into the glass filter crucible. The glass filter crucible with the weighed-in additive was fitted to a suction flask. 10 ml of methyl methacrylate were added to the additive, so that the additive was fully covered. The methyl methacrylate not absorbed by the additive ran down through the glass filter crucible. After 15 minutes, the glass filter crucible with the additive and the absorbed methyl methacrylate was weighed and the mass of the absorbed methyl methacrylate was determined. The determination was repeated three times in each case, and the mean value was determined. The glass filter crucible was treated in the same manner with methyl methacrylate without added additive as reference.

| Additive | Absorption capacity [g methyl methacrylate/g additive] |
|---|---|
| starch | 0.7 |
| cellulose | 1.8 |
| Aerosil ® 380 | 9.4 |

Figure 2:
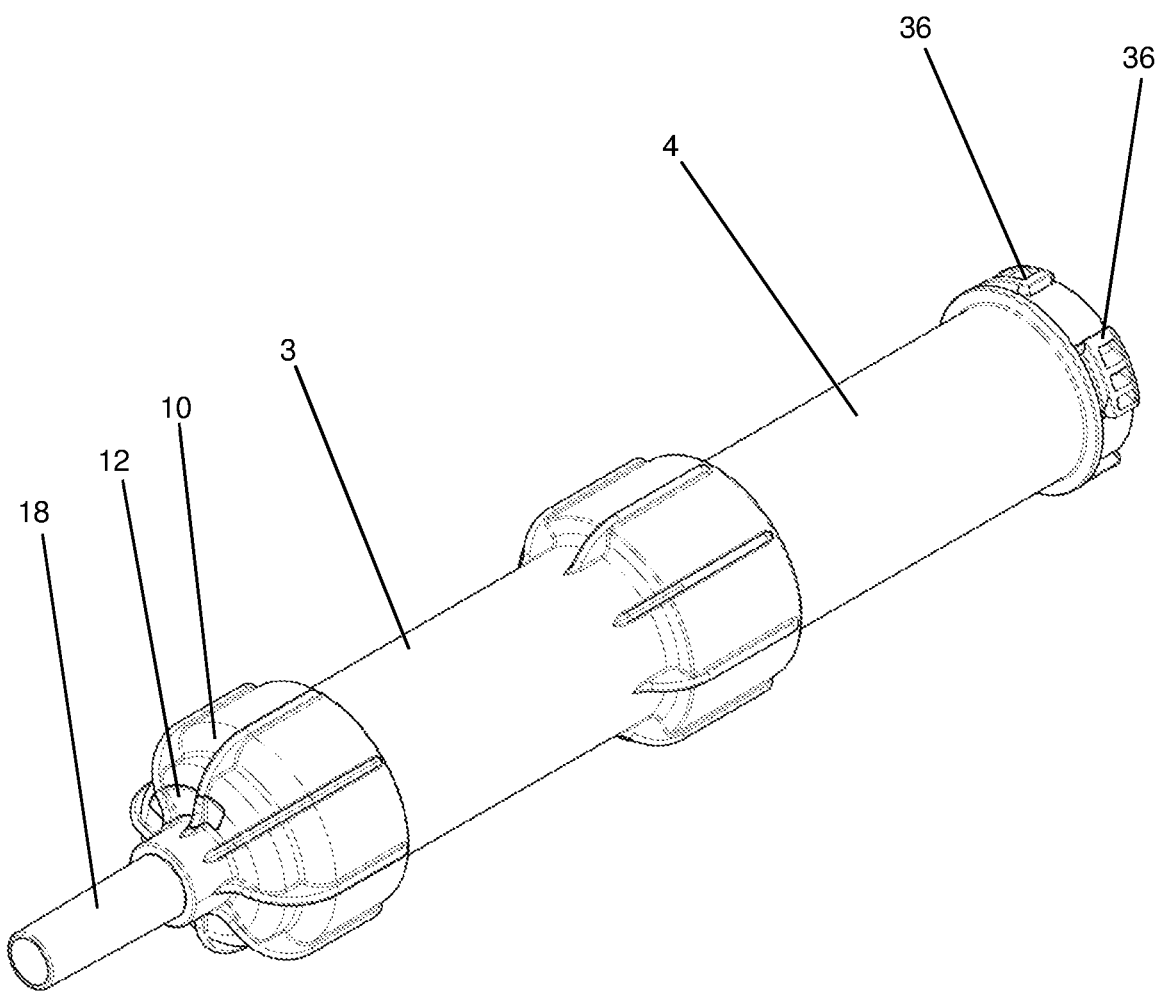
FIG. 2 is a schematic perspective view of the device according to FIG. 1.
Figure 3:
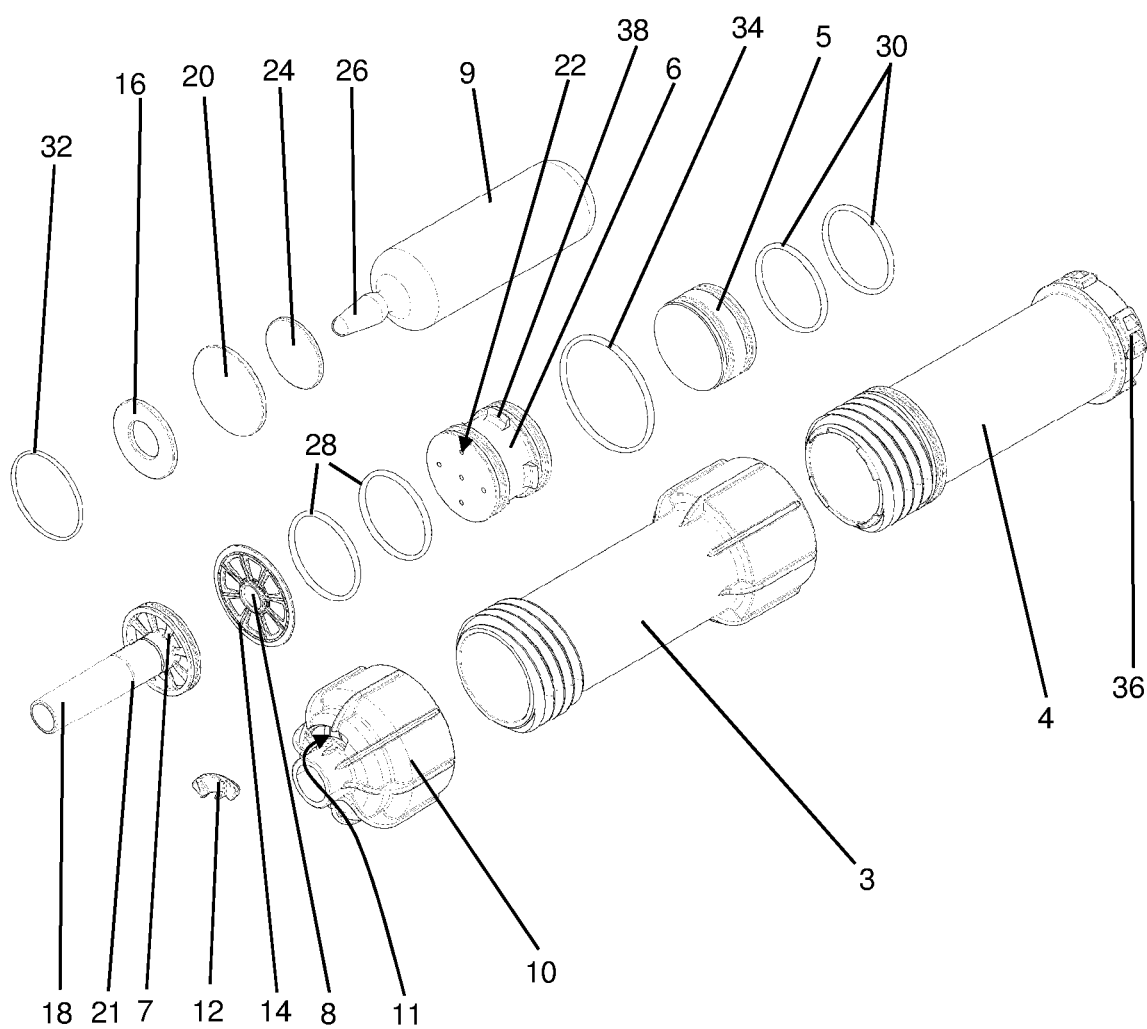
FIG. 3 is a perspective exploded illustration of the parts of the device according to FIGS. 1 and 2.
Figure 4:
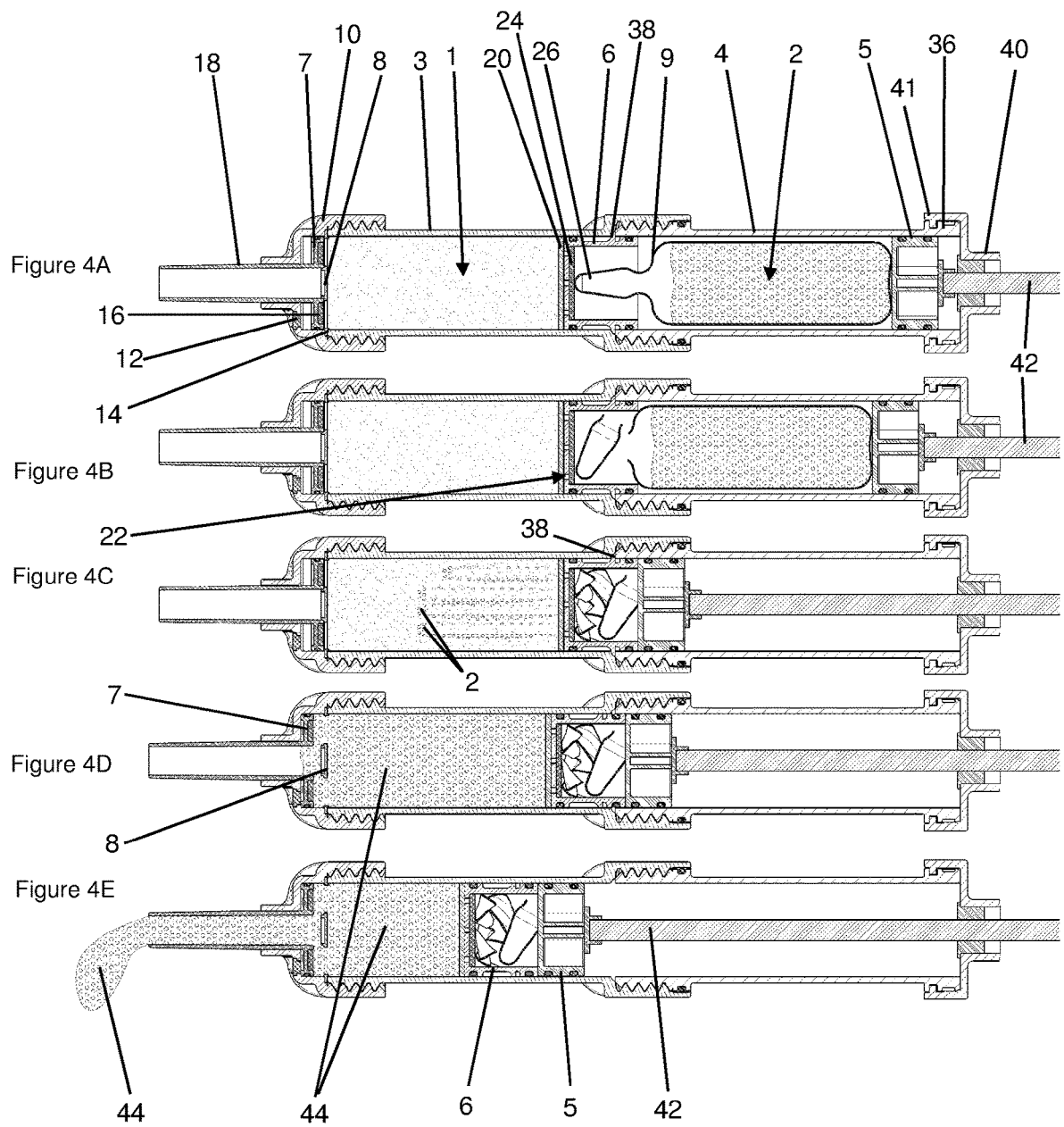
FIGS. 4A-E are five schematic cross-sectional views of the first exemplary device, which illustrate the sequence of the use of the device during the production and application of the bone cement dough.
Figure 5:
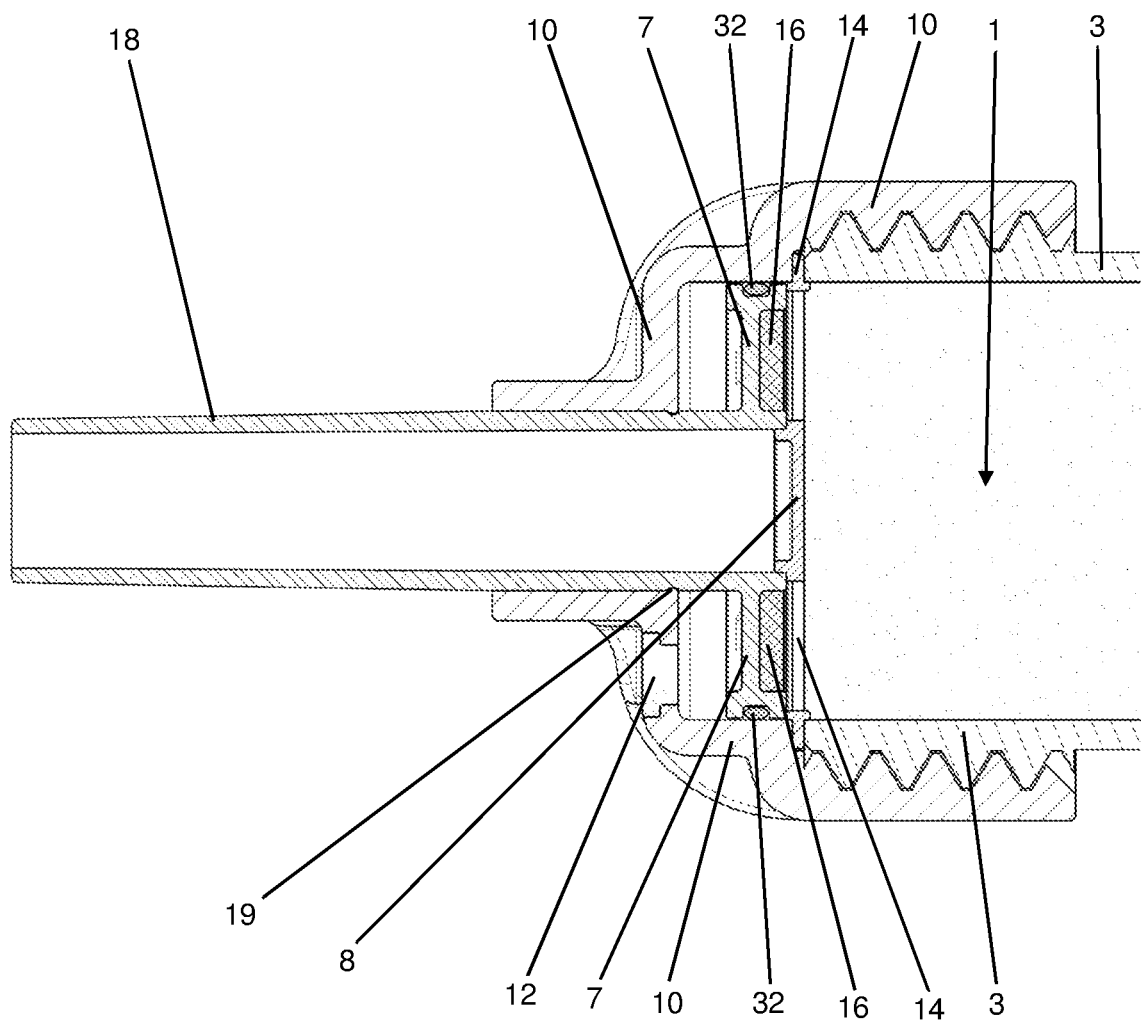
FIG. 5 is an enlarged detail of the closure system as schematic partial cross-sectional view of the first exemplary device.

FIGS. 1 to 5 illustrate an exemplary embodiment of a first device. Here, FIG. 1 illustrates a schematic cross-sectional view of the first exemplary device according to one embodiment in the starting state, FIG. 2 illustrates a schematic perspective view of the device, FIG. 3 illustrates a perspective exploded illustration of the parts of the device, FIGS. 4 A to E illustrate five schematic cross-sectional views of the device illustrating the sequence of the use of the device during the production and application of the bone cement dough, and FIG. 5 illustrates an enlarged detail as schematic partial cross-sectional view of the device. In the starting state of the device, a powder 1 as one starting component of a PMMA bone cement and a monomer liquid 2 as further starting component of the PMMA bone cement are contained in the device. The powder 1 contains a bone cement powder as main constituent and also a hydrophilic additive, with which the monomer liquid 2 can be distributed in the powder 1. The powder 1 and the monomer liquid 2 are contained in a two-part cartridge 3, 4, wherein the powder 1 is arranged in a front cartridge part 3 having a front interior and the monomer liquid 2 is arranged in a rear cartridge part 4 having a rear interior of the cartridge 3, 4. The rear interior and the front interior together delimit a cylindrical interior of the cartridge 3, 4.

A conveying piston 5 is arranged at the rear side of the device (at the bottom in FIG. 1, towards the top right-hand corner at the rear in FIG. 2, and on the right in FIG. 4) and can be advanced linearly in the axial direction in the interior of the cartridge 3, 4 in the direction of the front side of the device (at the top in FIG. 1, towards the bottom left-hand corner at the front in FIG. 2, and on the left in FIG. 4), or is mounted movably in said direction. The conveying piston 5 closes off the rear side of the interior of the cartridge 3, 4. A discharge piston 6 is arranged in the rear end of the front interior, or in the connection from the front interior to the rear interior of the cartridge 3, 4, and can be advanced linearly in the axial direction in the interior of the cartridge 3, 4 in the direction of the front side of the device, or is mounted movably in said direction. The discharge piston 6 is thus arranged between the powder 1 and the monomer liquid 2 in the interior of the cartridge 3, 4.

A closure system is arranged at the front side of the device, with which closure system the interior of the cartridge 3, 4 is closed off towards the front, however the closure system can be opened in order to discharge a bone cement dough 44 mixed from the starting components 1, 2 (see FIGS. 4 D and 4 E). A wall 7 of the closure system has a central circular discharge opening and is arranged movably in the axial direction of the front interior of the front cartridge part 3. The discharge opening is delimited by an inner ring. The wall 7 is constructed in the manner of a wheel with an outer ring, which is connected to the inner ring, delimiting the discharge opening, by means of a plurality of struts. The inner ring, the outer ring, and the struts are made in one part from plastic. The closure system also includes a stopper 8, with which the discharge opening is closed in the starting state, as is illustrated in FIG. 1.

The monomer liquid 2 is contained in a closed glass ampoule 9 as container 9 for the monomer liquid 2. The monomer liquid 2 can be stored for a long time within the glass ampoule 9 in the device.

The closure system of the device is arranged in a cartridge head 10, which delimits the front region of the front interior or the front cartridge part 3 of the cartridge 3, 4. More precisely, the cartridge head 10 is part of the cartridge 3, 4. A ventilation opening 11 is provided in the cartridge head 10 at the front side and is closed by a cap 12 in the storage state or in the starting state of the device. The interior of the cartridge 3, 4 can be gassed with a sterilising gas, such as ethylene oxide, through the ventilation opening 11, and the content of the cartridge 3, 4 can thus be sterilised. Further ventilation openings (not illustrated) are in one embodiment also provided in the wall of the rear cartridge part 4 directly next to the position of the conveying piston 5, similarly to the exemplary embodiments according to FIGS. 9 to 18, which further ventilation openings connect the interior of the cartridge 3, 4 to the surrounding environment and through which openings the interior of the cartridge 3, 4 can be gassed with the sterilising gas from outside. In the event of a movement of the conveying piston 5 in the direction of the cartridge head 10, these rear-side ventilation openings are closed by the conveying piston 5, so that none of the monomer liquid 2 escaping from the ampoule 9 can pass outwardly from the rear part of the interior. The sterilising gas can thus be conducted through the cartridge 3, 4.

The stopper 8 of the closure system is held by a retaining ring 14, wherein the stopper 8 is connected to an outer ring of the retaining ring 14 by means of struts of the retaining ring 14. The retaining ring 14 is fixed externally in the connection between the cartridge head 10 and the front cartridge part 3. The stopper 8 is thus also fixed relative to the cartridge 3, 4.

The gaps open between the struts of the wall 7 of the closure system are covered by a filter 16 in the form of a punched disc, which is gas-permeable, but impermeable for the powder 1 and the bone cement dough 44. The wall 7 is thus permeable for gases such as ethylene oxide, but impermeable for the powder 1 and the bone cement dough 44. Similarly to the retaining ring 14, the wall 7 is formed specifically by a framework in the form of the outer ring with the spokes extending radially inwardly towards the discharge opening and is thus permeable if the gaps thereof are not covered by the filter 16. The structure of the wall 7 and of the retaining ring 14 can be seen most clearly in FIG. 3. The wall 7 with the filter 16, and also with the stopper 8 held immovably relative to the cartridge 3, 4 and with the retaining ring 14 form a closure system for the device according to one embodiment.

A discharge tube 18, through which the bone cement dough 44 is applied with use of the device (see FIG. 4 E), is formed in one part with the wall 7 and is arranged at the discharge opening or at the inner ring of the wall 7 delimiting the discharge opening. The discharge tube 18 thus opens out into the discharge opening in the interior of the cartridge 3, 4. The discharge tube 18 is thus also moved with the wall 7. To this end, the discharge tube 18 is mounted movably in the longitudinal direction (that is, in the axial direction of the cylindrical interior of the cartridge 3, 4) by means of a feedthrough in the cartridge head 10. Lugs 19 are provided in the feedthrough, so that the discharge tube 18 and thus the wall 7 with the filter 16 can be moved relative to the cartridge head 10 only against a resistance. A peripheral groove 21 is provided in the discharge tube 18, which groove, together with the lugs 19, forms a releasable locking of the discharge tube 18 and therefore the wall 7 relative to the cartridge head 10 and thus relative to the cartridge 3, 4. The wall 7 with the filter 16 can also be referred to as a sterilisation piston. The powder 1 is pressed under pressure into the front part of the interior of the cartridge 3, 4 between the wall 7 with the filter 16 and the discharge piston 6 and is under a resilient mechanical pressure. By locking the lugs 19 with the peripheral groove 21 in the feedthrough, it should be possible to prevent the resilient pressure exerted by the compressed powder 1 onto the wall 7 with the filter 16 from being strong enough to push the wall 7 with the filter 16 in the direction of the front side of the cartridge 3, 4 or against the front side of the interior delimited by the cartridge head 10 and thus relieve the powder 1 of pressure again.

A pore filter 20 impermeable for the powder 1, but permeable for the monomer liquid 2 is arranged on the side of the discharge piston 6 pointing towards the powder 1. The powder 1 should thus be prevented from being able to be advanced through passageways 22, which are provided in the discharge piston 6, into the rear part of the interior of the cartridge 3, 4. Here, the pore filter 20 covers the passageways 22, so that the powder 1 also cannot be advanced into the passageways 22. The monomer liquid 2 is hereby prevented from reacting prematurely with cement powder particles of the powder 1 already when the ampoule 9 has been opened, that is, before the monomer liquid 2 has been pressed into the front part of the interior. It is thus possible to prevent the passageways 22 from being blocked by swelling bone cement and thus preventing any further introduction of monomer liquid 2 into the powder 1.

On the side of the discharge piston 6 opposite the pore filter 20, there is arranged a mesh 24 or sieve 24, by means of which splinters of the broken glass ampoule 9 are prevented from passing into the passageways 22. It should also be ensured hereby that the monomer liquid 2 from the rear part of the interior of the cartridge 3, 4 can be pushed without difficulty into the powder 1. When the ampoule 9 is broken open, an ampoule head 26 is firstly broken off and the ampoule 9 thus opened (see FIG. 4 B). The monomer liquid 2 from the ampoule 9 can then flow out into the front part of the interior of the cartridge 3, 4 and can then be pressed through the passageways 22 into the powder 1 (see FIG. 4 C). Here, the ampoule 9 is shattered into fragments that are so small that they fit into a cavity formed on the side of the discharge piston 6 facing towards the cartridge base (downwardly in FIG. 1, towards the top right-hand corner at the rear in FIG. 2, and on the right in FIG. 4).

So that the monomer liquid 2 is not pushed past the discharge piston 6 into the front part of the interior of the cartridge 3, 4, two peripheral ring seals 28 made of rubber are provided on the discharge piston 6, by means of which the discharge piston 6 is sealed with respect to the wall of the interior of the cartridge 3, 4. Two peripheral ring seals 30 made of rubber are also provided on the conveying piston 5, by means of which a discharge of monomer liquid 2 outwardly at the cartridge base is avoided. The sealing effect of the seals 30 must at least be sufficient for no monomer liquid 2 to be discharged, even if, by means of the conveying piston 5, a pressure is exerted onto the monomer liquid 2 which is of such a magnitude that the monomer liquid is pressed through the mesh 24, the passageways 22 and the pore filter 20 into the powder 1.

Furthermore, the wall 7 is sealed by means of a peripheral seal 32 made of rubber with respect to the wall of the front interior in the region of the cartridge head 10. The seal 32 runs externally around the outer ring of the wall 7. The two cartridge parts 3, 4 are furthermore also sealed with respect to one another by means of a peripheral seal 34 made of rubber. The two cartridge parts 3, 4 are screwed to one another by means of a thread. To this end, an internal thread is provided on the front cartridge part 3 and an external thread is provided on the rear cartridge part 4. Similarly, the cartridge head 10 and the rest of the front cartridge part 3 are connected to one another, wherein here the seal is provided by the thread itself or by the retaining ring 14 clamped therebetween.

A retainer 36 for fastening a press-out apparatus 40 (see FIG. 4) is provided externally on the rear cartridge part 4 at the cartridge base.

A plurality of hooks 38 are provided as detent means laterally on the discharge piston 6 and engage in matching recesses at the connection of the front cartridge part 3 to the rear cartridge part 4 at the wall of the interior. The resultant latching of the discharge piston 6 to the cartridge 3, 4 is strong enough to resist the pressure of the forces occurring as the glass ampoule 9 is shattered and the pressure of the monomer liquid 2 as the conveying piston 5 is advanced forwards. Only when the conveying piston 5 bears directly against the discharge piston 6 (see FIG. 4 C) is the latched connection released, or are the hooks 38 deformed and slide from the recesses in the wall of the interior of the cartridge 3, 4, and the discharge piston 6 is then pushed by the conveying piston 5 in the direction of the cartridge head 10 at the front side of the device.

A filling material (not illustrated), such as a foam material insert and/or plastic grains, can in one embodiment be provided in the cavity in the discharge piston 6 formed in the rear side of the discharge piston 6. The volume of the monomer liquid 2 which remains in this cavity and cannot be pressed by the conveying piston 5 into the powder 1 shall thus be kept as small as possible. Furthermore, this filling material can be used as transport protection and shock protection for the glass ampoule 9, so that the glass ampoule 9, as the device is transported in the starting state (see FIGS.

1 and 2), does not accidentally fracture. To this end, a compressible foam material can be arranged additionally around the glass ampoule 9 in the rear part of the interior of the cartridge 3, 4. Alternatively, mechanically deformable spacers formed from resilient plastic can also be used as transport protection.

The sequence of an exemplary method according to one embodiment for producing a bone cement dough is illustrated in FIG. 4 by five cross-sectional views (FIG. 4 A to FIG. 4 E) illustrated one above the other. The device is firstly inserted into a press-out apparatus 40, for which purpose the cartridge 3, 4 is fastened by means of the retainer 36 to a matching counterpiece 41 of the press-out apparatus 40 (see FIG. 4 A).

A ram 42 of the press-out apparatus 40 is then advanced relative to the counterpiece 41. The ram 42 bears against the conveying piston 5. The conveying piston 5 is thus pushed by the ram 42 in the direction of the discharge piston 6. By means of the movement of the conveying piston 5, the ampoule 9 is pushed relative to the discharge piston 6 locked by the detent means 38. The ampoule head 26 breaks off, and the ampoule 9 is opened (see FIG. 4 B).

The device in the press-out apparatus 40 is in one embodiment held here with the cartridge head 10 upwardly, so that, as the conveying piston 5 continues to be advanced further forwards, the air arranged at the top is pushed outwardly from the rear part of the interior upwardly through the powder 1 and through the gas-permeable filter 16. The monomer liquid 2 from the ampoule 9 is eventually pushed by the conveying piston 5 through the mesh 24 and/or the sieve 24, through the passageways 22 and through the pore filter 20 into the front part of the interior into the powder 1. In so doing, the ampoule 9 is further compressed and thus shatters into smaller fragments, which ultimately collect in the rear-side cavity of the discharge piston 6. The powder 1 contains a hydrophilic additive, which has a large surface energy with respect to the aqueous monomer liquid 2, which surface energy is greater than that of the bone cement powder. At the same time, the capillary forces on account of the compressed powder 1 are great, since the gaps between the powder particles are small. In addition, the monomer liquid 2 is pressed with pressure into the powder 1. As a result of all of these measures, the monomer liquid 2 is conducted quickly into and through the powder 1 and can spread and distribute fully within the powder 1 before the swelling cement powder particles prevent a further spreading of the monomer liquid 2 in the powder 1. Lastly, the conveying piston 5 contacts the discharge piston 6 (see FIG. 4 C).

The cement powder in the powder 1 reacts with the monomer liquid 2 and forms there the bone cement dough 44. In order to obtain the desired mixing ratio between powder 1 and monomer liquid 2 in the bone cement dough 44, excess monomer liquid 2 can be received at the front side of the cartridge 3, 4 between the porous filter 16 of the wall 7 and the cartridge head 10. The monomer liquid 2 is for this purpose pushed through the porous filter 16, which is impermeable for the powder 1 and the bone cement dough 44. Due to absorption of the excess monomer liquid 2 once the monomer liquid 2 has passed through the powder 1 as far as the wall 7, the bone cement dough 44 is prevented from becoming too runny and thus attaining an undesirable consistency. In addition, in order to avoid a consistency of the bone cement dough 44 that is too thick, the monomer liquid 2 is used in excess, so that the losses by the residues of the monomer liquid 2 remaining between the discharge piston 6 and the conveying piston 5 and also in the passageways 22 of the discharge piston 6 are offset.

Due to a further advancing of the conveying piston 5, the discharge piston 6 is driven in the direction of the cartridge head 10 and the latching or detent means 38 released. Due to the movement of the discharge piston 6 in the direction of the cartridge head 10, a pressure is exerted by the bone cement dough 44 onto the wall 7 and the filter 16 of the closure system. The bone cement dough 44 cannot flow through the filter 16, and therefore the pressure of the bone cement dough 44 acts on the filter 16 and the wall 7. The locking by the lugs 19 and the peripheral groove 21 is released, and therefore the wall 7, the filter 16 and the discharge tube 18 can move relative to the cartridge 3, 4 or the cartridge head 10, so that these parts of the closure system are pushed forwards, whereas the stopper 8, which is fixedly connected to the cartridge 3, 4 by means of the retaining ring 14, is not moved at the same time. The bone cement dough 44 here flows through the openings between the spokes of the retaining ring 14. In the meantime, the discharge opening in the wall 7 is opened. The wall 7, the filter 16, and the discharge tube 18 are driven forwards until the front side of the wall 7 bears against the frontal inner side of the cartridge head 10. This situation is illustrated in FIG. 4 D. The cartridge 3, 4 is now opened outwardly. The distance between the wall 7 and the stopper 8, if the wall 7 bears against the front side of the interior, is so great that the free area through which the bone cement dough 44 flows out is at least as large as the cross-sectional area of the discharge tube 18, so that the flow of bone cement dough 44 is hindered to the smallest extent possible.

By further advancing the conveying piston 5 and therefore the discharge piston 6, the finished bone cement dough 44 is pressed outwardly through the discharge opening and the discharge tube 18 and can be applied (see FIG. 4 E).

On account of the additive provided in the powder 1, it is possible to press in the monomer liquid 2 at one end face of the front part of the cylindrical interior of the cartridge 3, 4 and nevertheless achieve a complete distribution of the monomer liquid 2 in the powder 1. Due to the structure according to one embodiment of the device, it is possible to be able to use a conventional press-out apparatus 40 and, by means of a unidirectional linear movement of the ram 42, to open the container 9 for the monomer liquid 2, to press the monomer liquid 2 into the powder 1 and thus mix the bone cement dough 44, as well as to open the closure system and expel and apply the mixed bone cement dough 44. With the structure according to one embodiment of the closure system, it is possible to be able to use the force exerted by the ram 42 onto the conveying piston 5 in order to open the discharge opening.

Figure 6:
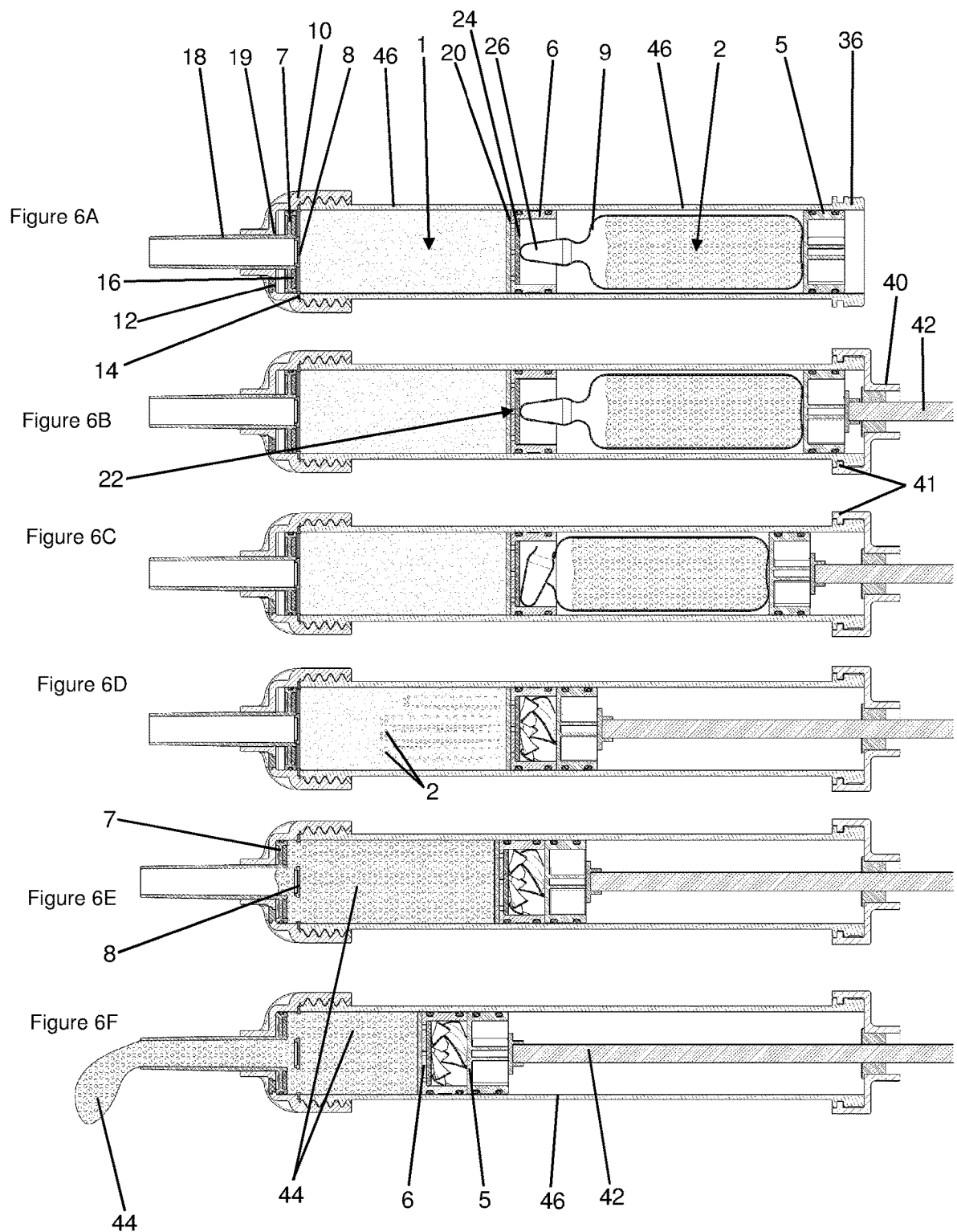
FIGS. 6A-F are six schematic cross-sectional views of a second exemplary device with one-part cartridge, which illustrate the sequence of the use of the device during the production and application of the bone cement dough.
Figure 7:
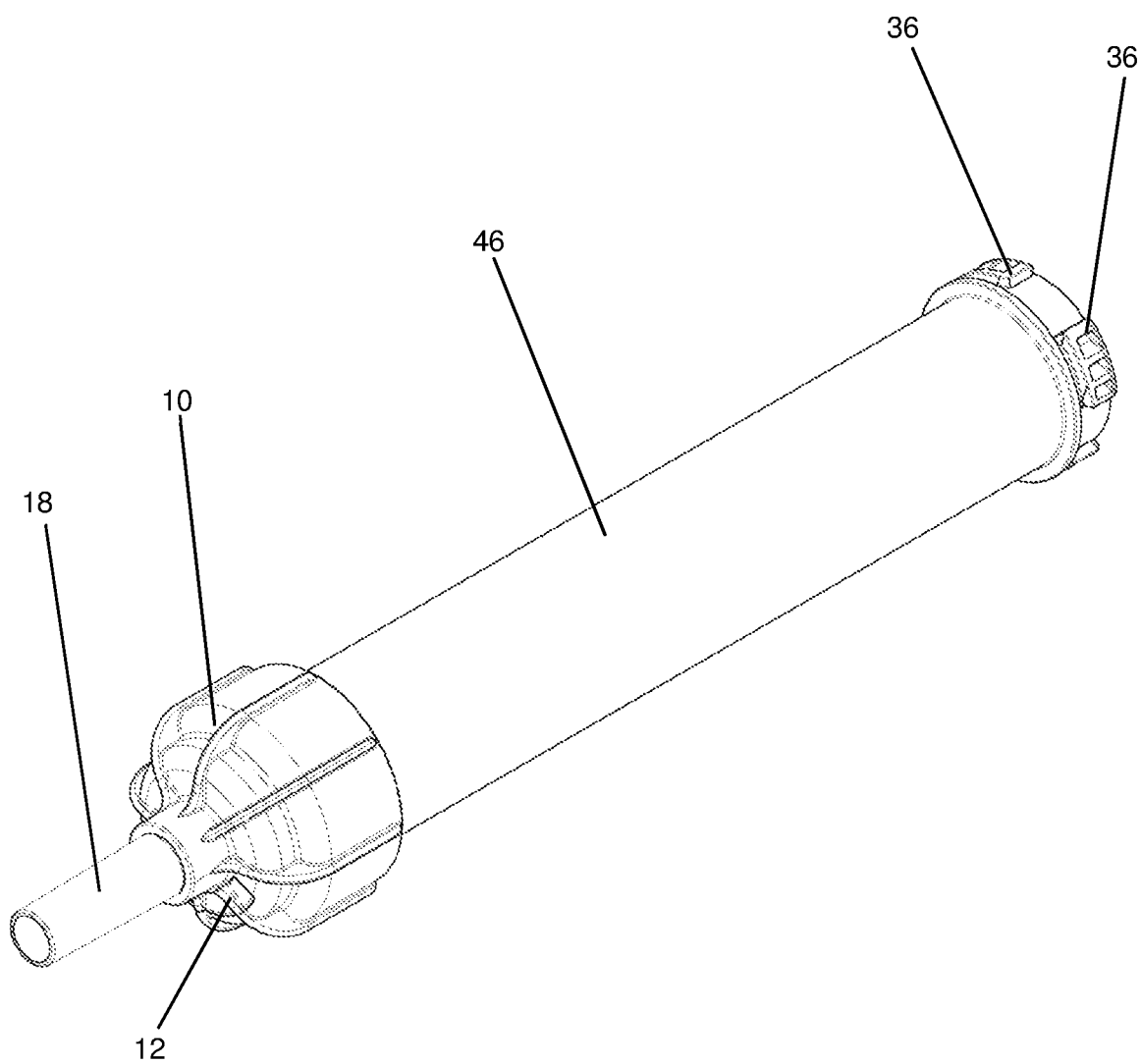
FIG. 7 is a perspective external view of the second exemplary device according to one embodiment according to FIG. 6.
Figure 8:
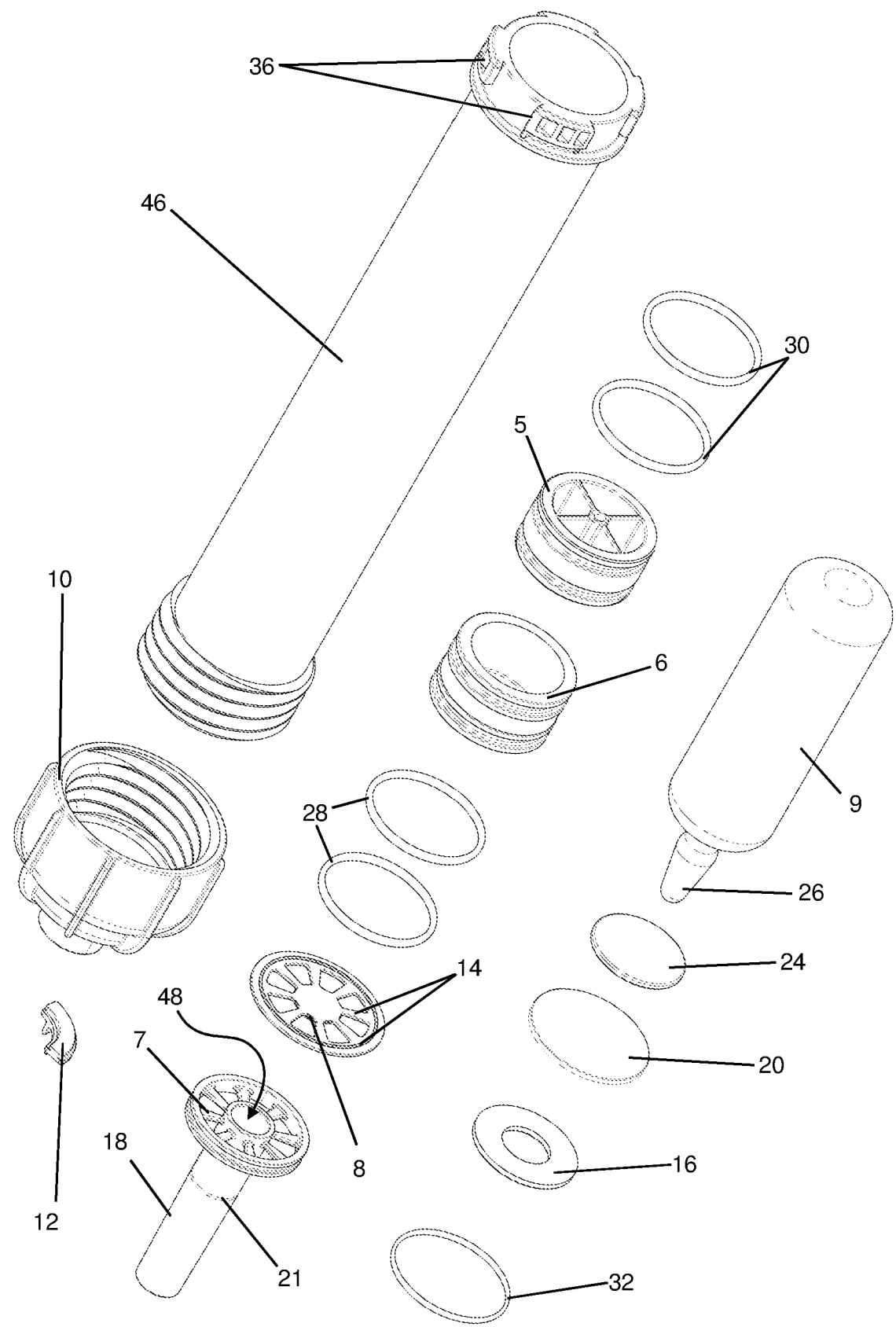
FIG. 8 is a perspective exploded illustration of the parts of the second device according to FIGS. 6 and 7.

A second exemplary device according to one embodiment is illustrated in FIGS. 6 to 8 and differs from the first exemplary device according to FIGS. 1 to 5 in that the second exemplary device has a cartridge 46 which does not consist of two cartridge parts, wherein the cartridge head 10 is still screwed on and the one discharge piston 6 in the interior of the cartridge 46 is not connected to the cartridge 46 by means of a detent means.

Here, FIG. 6 illustrates six schematic cross-sectional views A to F of the second exemplary device with one-part cartridge 46, which illustrate the sequence of the use of the device during the production and application of a bone cement dough 44, FIG. 7 illustrates a perspective external view of the second exemplary device according to one embodiment, and FIG. 8 illustrates a perspective exploded illustration of the second exemplary device.

The structure and operating principle of the second exemplary device correspond largely to those of the first exemplary device, and therefore reference can also be made largely to the description of the Figures illustrating the first exemplary embodiment. For example, the used powder 1 and the operating principle of the pistons 5, 6 is identical apart from the latching to the inner side of the cartridge in both exemplary embodiments.

In the starting state of the device, a powder 1 is contained in the device as one starting component of a PMMA bone cement and a monomer liquid 2 is contained in the device as further starting component of the PMMA bone cement. The powder 1 contains a bone cement powder as main constituent and also a hydrophilic additive, by means of which the monomer liquid 2 can be distributed within the powder 1. The powder 1 and the monomer liquid 2 are contained in the cartridge 46, wherein the powder 1 is arranged in a front cartridge part having a front interior and the monomer liquid 2 is arranged in a rear cartridge part having a rear interior of the cartridge 46. Together, the rear interior and the front interior delimit a cylindrical interior of the cartridge 46.

A conveying piston 5 is arranged at the rear side of the device (to the right in FIG. 6 and towards the top right-hand corner at the rear in FIG. 7) and can be advanced linearly in the axial direction in the interior of the cartridge 46 in the direction of the front side of the device (to the left in FIG. 6, towards the bottom left-hand corner at the front in FIG. 7), or is mounted movably in said direction. The conveying piston 5 closes off the rear side of the interior of the cartridge 46. A discharge piston 6 is arranged in the rear end of the front interior, or in the connection from the front interior to the rear interior of the cartridge 46, and can be advanced linearly in the axial direction in the interior of the cartridge 46 in the direction of the front side of the device, or is mounted movably in said direction. The discharge piston 6 is thus arranged in this embodiment between the powder 1 and the monomer liquid 2 in the interior of the cartridge 3, 4.

A closure system is arranged at the front side of the device, with which closure system the interior of the cartridge 46 is closed off towards the front, however the closure system can be opened in order to discharge a bone cement dough 44 mixed from the starting components 1, 2 (see FIGS. 6 E and 6 F). A wall 7 of the closure system has a central circular discharge opening 48 (see FIG. 8) and is arranged movably in the axial direction of the interior of the cartridge 46. The discharge opening 48 is delimited by an inner ring (see FIG. 8). The wall 7 is constructed in the manner of a wheel with an outer ring, which is connected to the inner ring, delimiting the discharge opening 48, by means of a plurality of struts. The inner ring, the outer ring, and the struts are made in one part from plastic. The closure system also includes a stopper 8, with which the discharge opening 48 is closed in the starting state, as is illustrated in FIG. 6 A.

The monomer liquid 2 is contained in a closed ampoule 9 made of plastic or glass as container 9 for the monomer liquid 2. The ampoule 9 is made of glass or of a plastic which is chemically resistant to the monomer liquid 2. The monomer liquid 2 can be stored for a long time within the ampoule 9 in the device.

The closure system of the device is arranged in a cartridge head 10, which delimits the front region of the interior of the cartridge 46. More precisely, the cartridge head 10 is part of the cartridge 46. A ventilation opening is provided in the cartridge head 10 at the front side and is closed by a cap 12 in the storage state or in the starting state of the device. The interior of the cartridge 46 can be gassed with a sterilising gas, such as ethylene oxide, through the ventilation opening, and the content of the cartridge 46 can thus be sterilised. Further ventilation openings (not illustrated) are in one embodiment also provided in the wall of the cartridge 46 directly next to the position of the conveying piston 5, similarly to the exemplary embodiments according to FIGS. 9 to 18, which further ventilation openings connect the interior of the cartridge 46 to the surrounding environment and through which openings the interior of the cartridge 46 can be gassed with the sterilising gas from outside. In the event of a movement of the conveying piston 5 in the direction of the cartridge head 10, these rear-side ventilation openings are closed by the conveying piston 5, so that none of the monomer liquid 2 escaping from the ampoule 9 can pass outwardly from the rear part of the interior. The sterilising gas can thus be conducted through the cartridge 46.

The stopper 8 of the closure system is held by a retaining ring 14, wherein the stopper 8 is connected to an outer ring of the retaining ring 14 by means of struts of the retaining ring 14. The retaining ring 14 is fixed externally in the connection between the cartridge head 10 and the rest of the cartridge 46. The stopper 8 is thus also fixed relative to the cartridge 46.

The gaps open between the struts of the wall 7 of the closure system are covered by a filter 16 in the form of a punched disc, which is gas-permeable, but impermeable for the powder 1 and the bone cement dough 44. The wall 7 is thus permeable for gases such as ethylene oxide, but impermeable for the powder 1 and the bone cement dough 44. Similarly to the retaining ring 14, the wall 7 is formed specifically by a framework in the form of the outer ring with the spokes extending radially inwardly towards the discharge opening 48 and is thus permeable if the gaps thereof are not covered by the filter 16. The structure of the wall 7 and of the retaining ring 14 can be seen most clearly in FIG. 8. The wall 7 with the filter 16, and also with the stopper 8 held immovably relative to the cartridge 46 and with the retaining ring 14 form a closure system for the device according to one embodiment.

A discharge tube 18, through which the bone cement dough 44 is applied with use of the device (see FIG. 6 F), is formed in one part with the wall 7 and is arranged at the discharge opening 48 or at the inner ring of the wall 7 delimiting the discharge opening 48. The discharge tube 18 is thus also moved with the wall 7. To this end, the discharge tube 18 is mounted movably in the longitudinal direction (that is, in the axial direction of the cylindrical interior of the cartridge 46) by means of a feedthrough in the cartridge head 10. Lugs 19 are provided in the feedthrough as constriction, so that the discharge tube 18 and thus the wall 7 with the filter 16 can be moved relative to the cartridge head 10 only against a resistance. A peripheral groove 21 is provided in the discharge tube 18, which groove, together with the lugs 19, forms a releasable locking of the discharge tube 18 and therefore the wall 7 relative to the cartridge head 10 and thus relative to the cartridge 3, 4. The powder 1 is pressed under pressure into the front part of the interior of the cartridge 46 between the wall 7 with the filter 16 and the discharge piston 6 and is under a resilient mechanical pressure. By locking the lugs 19 with the peripheral groove 21 in the feedthrough, it should be possible to prevent the resilient pressure exerted by the compressed powder 1 onto the wall 7 with the filter 16 from being strong enough to push the wall 7 with the filter 16 in the direction of the front side of the cartridge 46 or against the front side of the interior delimited by the cartridge head 10 and thus relieve the powder 1 of pressure again.

A pore filter 20 impermeable for the powder 1, but permeable for the monomer liquid 2 is arranged on the side of the discharge piston 6 pointing towards the powder 1. The powder 1 should thus be prevented from being able to be advanced through passageways 22, which are provided in the discharge piston 6, into the rear part of the interior of the cartridge 3, 4. Here, the pore filter 20 covers the passageways 22, so that the powder 1 also cannot be advanced into the passageways 22. The monomer liquid 2 is hereby prevented from reacting prematurely with cement powder particles of the powder 1 already when the ampoule 9 has been opened, that is, before the monomer liquid 2 has been pressed into the front part of the interior. It is thus possible to prevent the passageways 22 from being blocked by swelling bone cement and thus preventing any further introduction of monomer liquid 2 into the powder 1.

On the side of the discharge piston 6 opposite the pore filter 20, there is arranged a mesh 24 or sieve 24, by means of which fragments of the broken ampoule 9 are prevented from passing into the passageways 22. It should also be ensured hereby that the monomer liquid 2 from the rear part of the interior of the cartridge 46 can be pushed without difficulty into the powder 1. When the ampoule 9 is broken open, an ampoule head 26 is firstly broken off and the ampoule 9 thus opened (see FIG. 6 C). The monomer liquid 2 from the ampoule 9 can then flow out into the front part of the interior of the cartridge 46 and can then be pressed through the passageways 22 into the powder 1 (see FIG. 6 D). Here, the ampoule 9 is shattered into fragments that are so small that they fit into a cavity formed on the side of the discharge piston 6 facing towards the cartridge base (to the right in FIG. 6 and in the top right-hand corner at the rear in FIG. 7).

A retainer 36 for fastening a press-out apparatus 40 (see FIG. 6) is provided externally on the rear cartridge part 4 at the cartridge base.

The discharge piston 6 sits in the interior of the cartridge 46 with a press fit. The two peripheral ring seals 28 are heavily compressed here in such a way that the discharge piston 6 initially is firmly fitted in the interior of the cartridge 46. The resulting retention of the discharge piston 6 with the cartridge 46 is strong enough to resist the pressure of the forces occurring as the ampoule 9 shatters and the pressure of the monomer liquid 2 as the conveying piston 5 is advanced forwards. Only when the conveying piston 5 bears directly against the discharge piston 6 (see FIG. 6 D) is the force transferred to the discharge piston 6 great enough for the static friction between the discharge piston 6 and the inner wall of the cartridge 46 to be overcome, so that the discharge piston 6 is then pushed by the conveying piston 5 in the direction of the cartridge head 10 at the front side of the device.

A filling material (not illustrated), such as a foam material insert and/or plastic grains, can in one embodiment be provided in the cavity in the discharge piston 6 formed in the rear side of the discharge piston 6. The volume of the monomer liquid 2 which remains in this cavity and cannot be pressed by the conveying piston 5 into the powder 1 shall thus be kept as small as possible. Furthermore, this filling material can be used as transport protection and shock protection for the ampoule 9, so that the ampoule 9, as the device is transported in the starting state (see FIG. 6 A), does not accidentally fracture. For the same purpose, the ampoule body of the ampoule 9 in the rear part of the interior of the cartridge 46 can also be encased in a compressible foam material.

The sequence of an exemplary method according to one embodiment is illustrated in FIG. 6 by six cross-sectional views (FIG. 6 A to FIG. 6 F) illustrated one above the other. FIG. 6 A illustrates the device in the starting state, in which the starting components 1, 2 are stored and preserved. The device can be delivered in this state. The device is firstly inserted into a press-out apparatus 40, for which purpose the cartridge 46 is fastened by means of the retainer 36 to a matching counterpiece 41 of the press-out apparatus 40 (see FIG. 6 B).

A ram 42 of the press-out apparatus 40 is then advanced relative to the counterpiece 41. The ram 42 bears against the conveying piston 5. The conveying piston 5 is thus pushed by the ram 42 in the direction of the discharge piston 6. By means of the movement of the conveying piston 5, the ampoule 9 is pushed relative to the discharge piston 6 firmly fitted with a press fit. The ampoule head 26 breaks off, and the ampoule 9 is opened (see FIG. 6 C).

The device in the press-out apparatus 40 is in one embodiment held here with the cartridge head 10 upwardly, so that, as the conveying piston 5 continues to be advanced further forwards, the air arranged at the top is pushed outwardly from the rear part of the interior upwardly through the powder 1 and through the gas-permeable filter 16. The monomer liquid 2 from the ampoule 9 is eventually pushed by the conveying piston 5 through the mesh 24 and/or the sieve 24, through the passageways 22 and through the pore filter 20 into the front part of the interior into the powder 1. In so doing, the ampoule 9 is further compressed and thus shatters into smaller fragments, which ultimately collect in the rear-side cavity of the discharge piston 6. The powder 1 contains a hydrophilic additive, which has a large surface energy with respect to the aqueous monomer liquid 2, which surface energy is greater than that of the bone cement powder. At the same time, the capillary forces on account of the compressed powder 1 are great, since the gaps between the powder particles are small. In addition, the monomer liquid 2 is pressed with pressure into the powder 1. As a result of all of these measures, the monomer liquid 2 is conducted quickly into and through the powder 1 and can spread and distribute fully within the powder 1 before the swelling cement powder particles prevent a further spreading of the monomer liquid 2 in the powder 1. Lastly, the conveying piston 5 contacts the discharge piston 6 (see FIG. 6 D).

The cement powder in the powder 1 reacts with the monomer liquid 2 and forms there the bone cement dough 44. In order to obtain the desired mixing ratio between powder 1 and monomer liquid 2 in the bone cement dough 44, excess monomer liquid 2 can be received at the front side of the cartridge 46 between the porous filter 16 of the wall 7 and the cartridge head 10. The monomer liquid 2 is for this purpose pushed through the porous filter 16, which is impermeable for the powder 1 and the bone cement dough 44. Due to absorption of the excess monomer liquid 2 once the monomer liquid 2 has passed through the powder 1 as far as the wall 7, the bone cement dough 44 is prevented from becoming too runny and thus attaining an undesirable consistency. In addition, in order to avoid a consistency of the bone cement dough 44 that is too thick, the monomer liquid 2 is used in excess, so that the losses by the residues of the monomer liquid 2 remaining between the discharge piston 6 and the conveying piston 5 and also in the passageways 22 of the discharge piston 6 are offset.

Due to a further advancing of the conveying piston 5, the discharge piston 6 is driven in the direction of the cartridge head 10, wherein the pressure exerted by the conveying piston 5 onto the discharge piston 6 is sufficient to overcome the static friction of the discharge piston 6 relative to the wall of the interior and therefore to advance the discharge piston 6 in the direction of the cartridge head 10. Due to the movement of the discharge piston 6 in the direction of the cartridge head 10, a pressure is exerted by the bone cement dough 44 onto the wall 7 and the filter 16 of the closure system. The bone cement dough 44 cannot flow through the filter 16, and therefore the pressure of the bone cement dough 44 acts on the filter 16 and the wall 7. The locking between the lugs 19 and the peripheral groove 21 in the discharge tube 18 is released by this pressure. Since the wall 7, the filter 16 and the discharge tube 18 are now mounted movably relative to the cartridge 46 or the cartridge head 10, these parts of the closure system are pushed forwards, while the stopper 8, which is fixedly connected to the cartridge 46 by means of the retaining ring 14, is not moved at the same time. The bone cement dough 44 here flows through the openings between the spokes of the retaining ring 14. In the meantime, the discharge opening 48 in the wall 7 is opened. The wall 7, the filter 16, and the discharge tube 18 are driven forwards until the front side of the wall 7 bears against the frontal inner side of the cartridge head 10. This situation is illustrated in FIG. 6 E. The cartridge 46 is now opened outwardly. The distance between the wall 7 and the stopper 8, if the wall 7 bears against the front side of the interior, is so great that the free area through which the bone cement dough 44 flows out is at least as large as the cross-sectional area of the discharge tube 18 or the discharge opening 48, so that the flow of bone cement dough 44 is hindered to the smallest extent possible.

By further advancing the conveying piston 5 and therefore the discharge piston 6, the finished bone cement dough 44 is pressed outwardly through the discharge opening and the discharge tube 18 and can be applied (see FIG. 6 F).

On account of the additive provided in the powder 1, it is possible to press in the monomer liquid 2 at one end face of the front part of the cylindrical interior of the cartridge 46 and nevertheless achieve a complete distribution of the monomer liquid 2 in the powder 1. Due to the structure according to one embodiment of the device, it is possible to be able to use a conventional press-out apparatus 40 and, by means of a unidirectional linear movement of the ram 42, to open the container 9 for the monomer liquid 2, to press the monomer liquid 2 into the powder 1 and thus mix the bone cement dough 44, as well as to open the closure system and expel and apply the mixed bone cement dough 44. With the structure according to one embodiment of the closure system, it is possible to be able to use the force exerted by the ram 42 onto the conveying piston 5 in order to open the discharge opening 48.

FIGS. 9 to 13 illustrate a third exemplary device according to one embodiment, which differs from the first exemplary device according to FIGS. 1 to 5 for example, in that the third exemplary device has a cartridge 50 which does not consist of two cartridge parts, wherein the cartridge head 10 is still screwed on, in that a filling material 52 is provided in a rear-side cavity of the discharge piston 6, and in that the closure system is structured differently.

Figure 9:
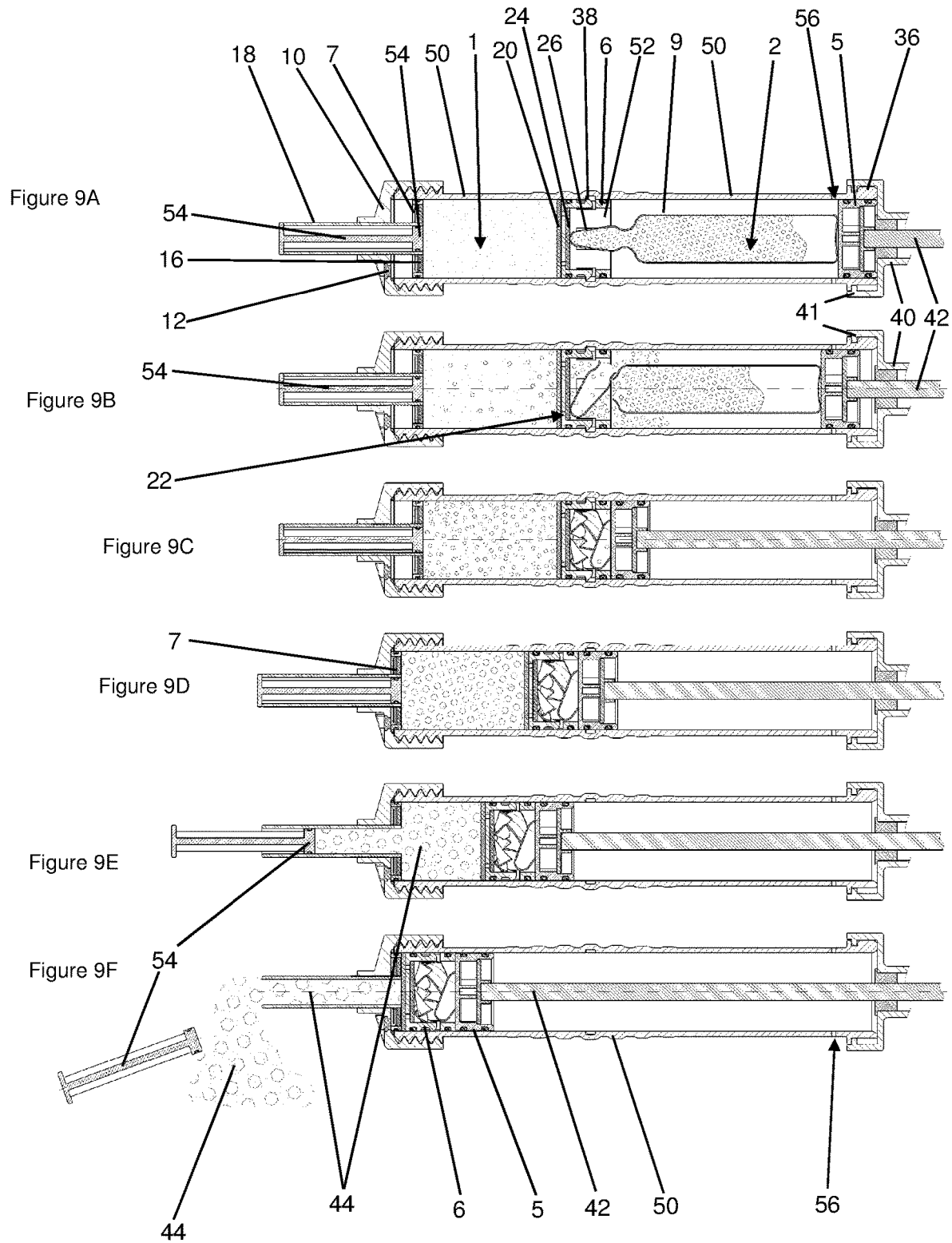
FIGS. 9A-F are six schematic cross-sectional views of a third exemplary device, which illustrate the sequence of the use of the device during the production and application of the bone cement dough.
Figure 10:
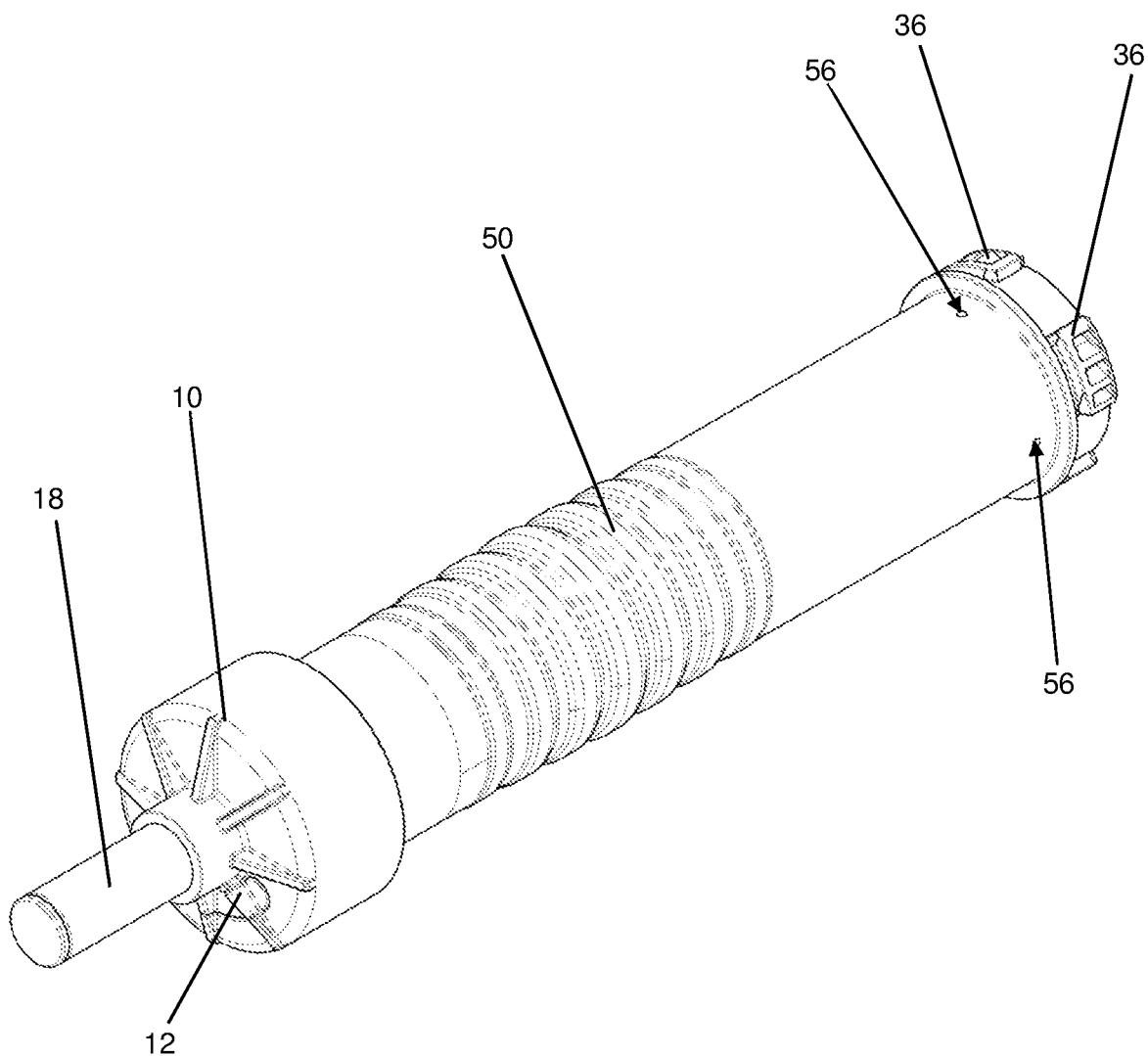
FIG. 10 is a perspective external view of the third exemplary device according to one embodiment according to FIG. 9.
Figure 11:
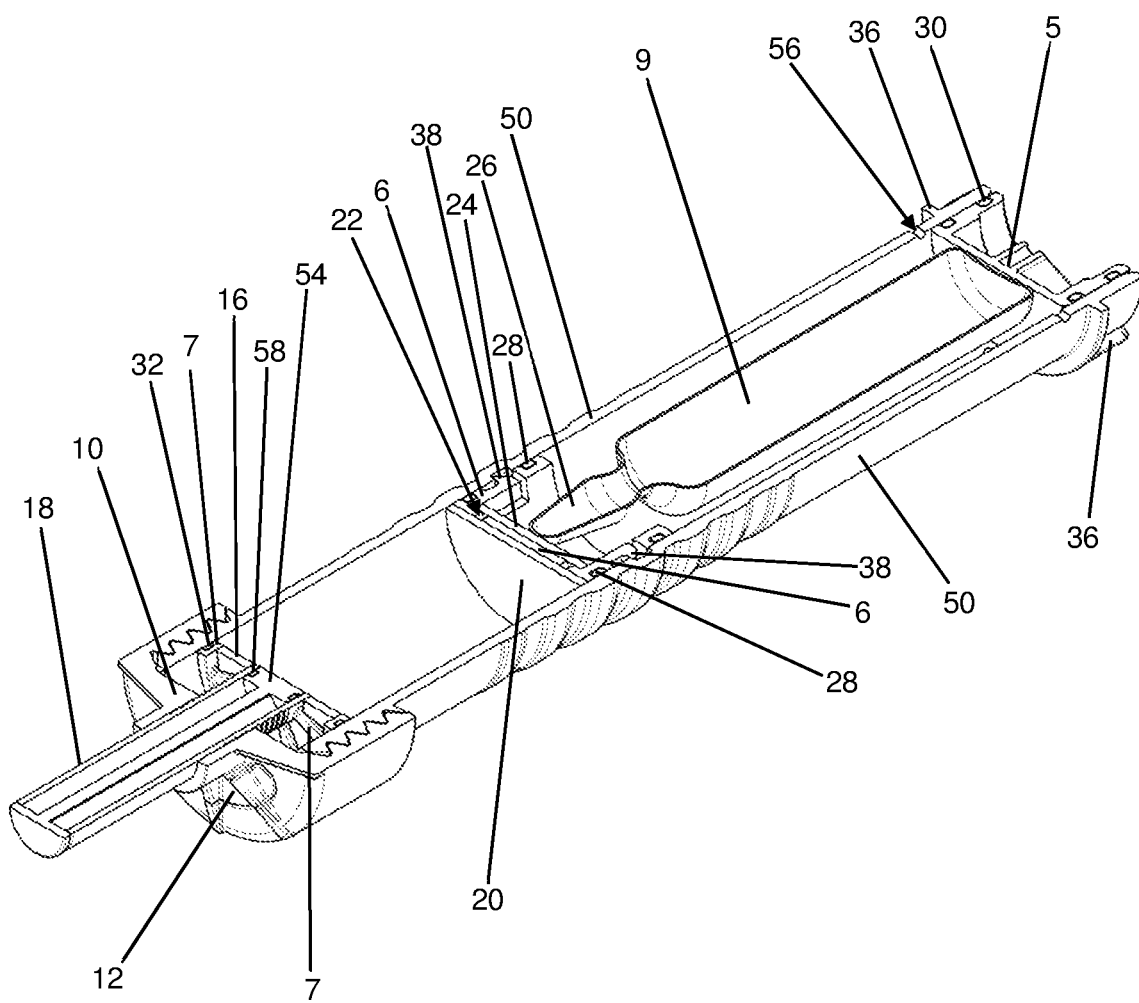
FIG. 11 is a perspective cross-sectional view of the third exemplary device according to one embodiment according to FIGS. 9 and 10 in the starting state.
Figure 12:
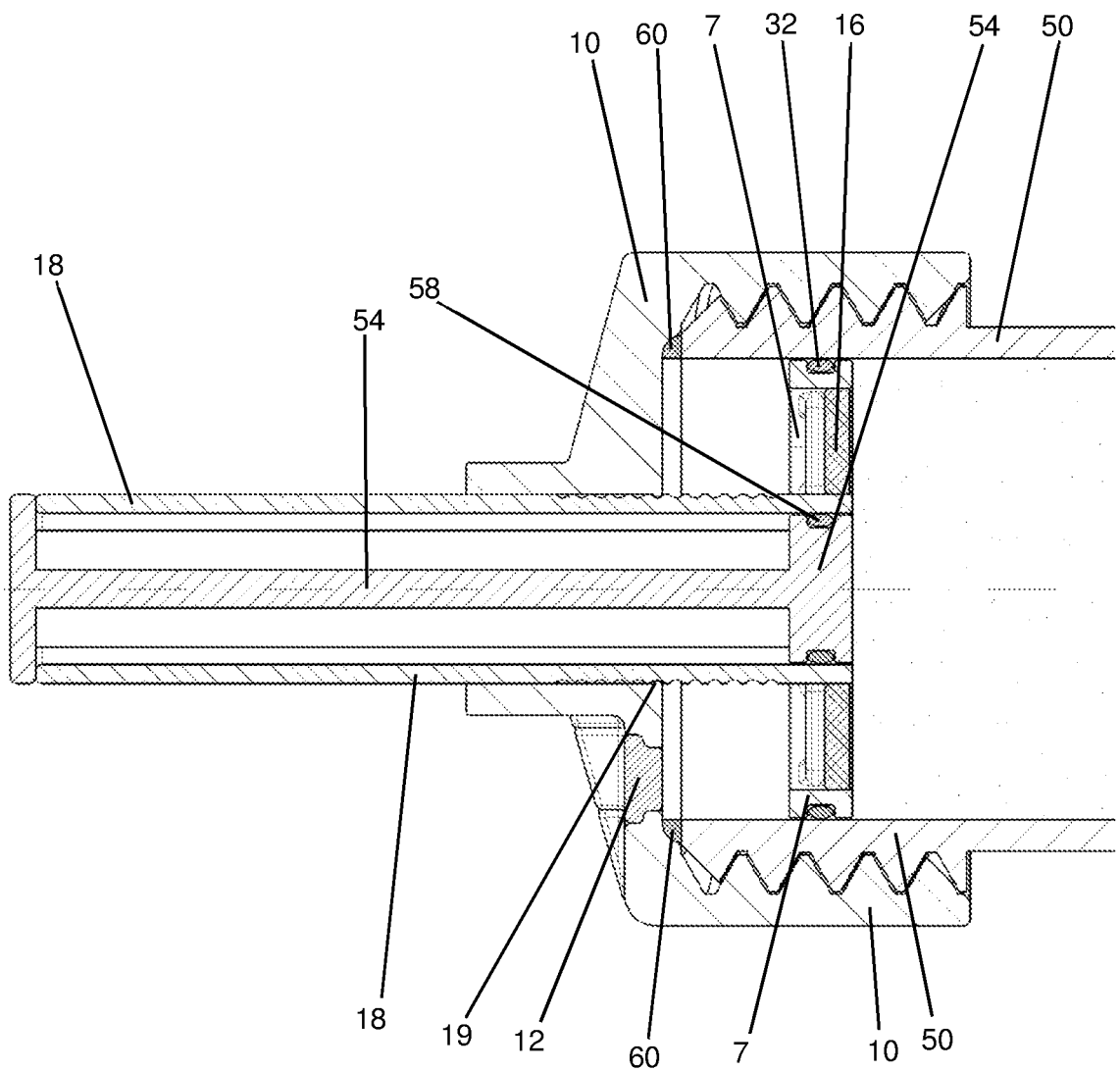
FIG. 12 is an enlarged detail as schematic partial cross-sectional view of the third exemplary device in the starting state.
Figure 13:
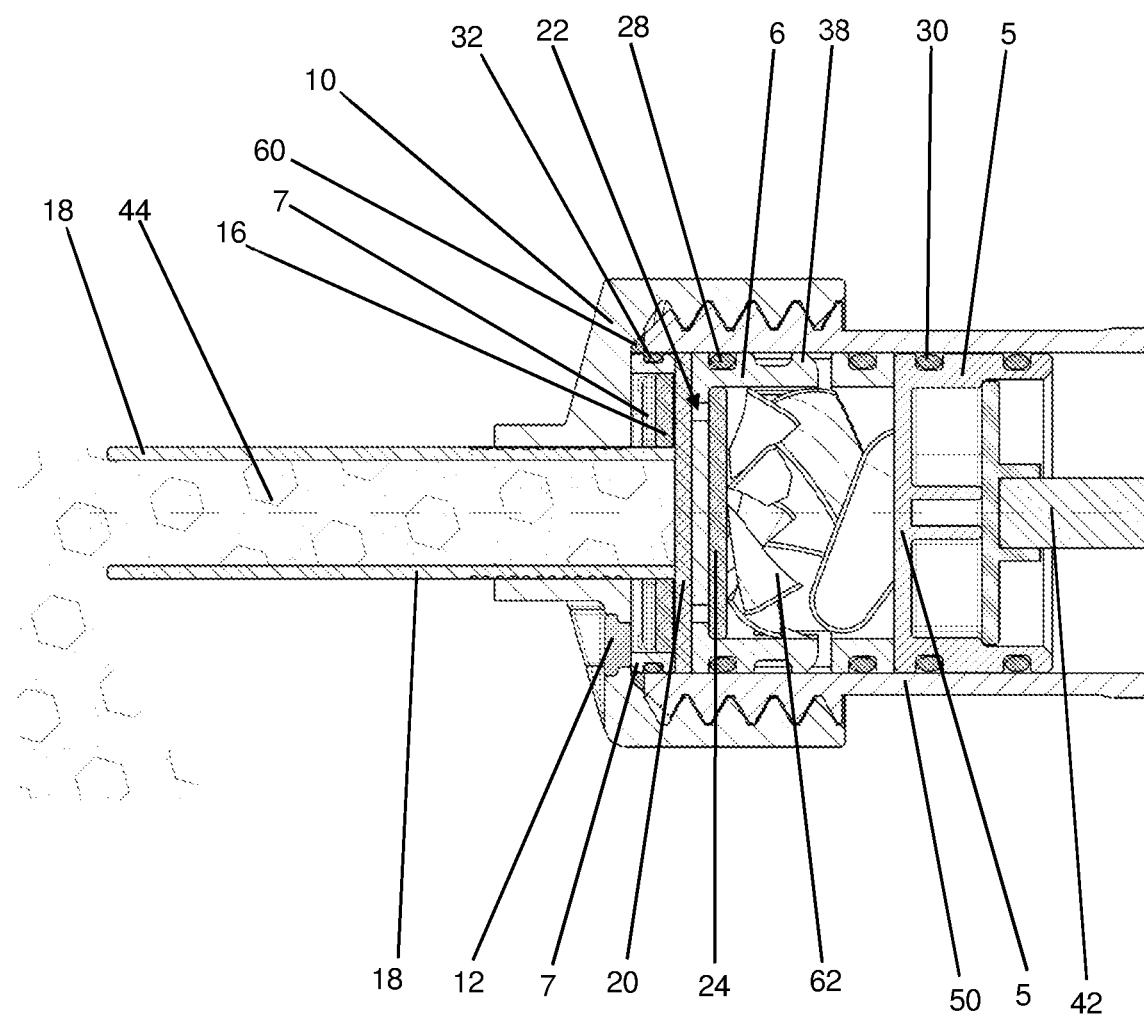
FIG. 13 is an enlarged detail as schematic partial cross-sectional view of the third exemplary device once the bone cement dough has been pressed out.

Here, FIG. 9 illustrates six schematic cross-sectional views A to F of the third exemplary device, which illustrate the sequence of the use of the device during the production and application of the bone cement dough, FIG. 10 illustrates a perspective external view of the device, FIG. 11 illustrates a perspective cross-sectional view of the device in the starting state, FIG. 12 illustrates an enlarged detail of the alternative closure system as schematic partial cross-sectional view of the device in the starting state, and FIG. 13 illustrates an enlarged detail of the alternative closure system as schematic partial cross-sectional view of the third exemplary device once the bone cement dough 44 has been pressed out.

The structure and operating principle of the third exemplary device correspond largely to those of the first exemplary device, so that reference can also be made largely to the description of the Figures illustrating the first exemplary embodiment. For example, the used powder 1 and the fundamental operating principle of the two pistons 5, 6 are identical.

In the starting state of the device, a powder 1 is contained in the device as one starting component of a PMMA bone cement and a monomer liquid 2 is contained in the device as further starting component of the PMMA bone cement. The powder 1 contains a bone cement powder as main constituent and also a hydrophilic additive, by means of which the monomer liquid 2 can be distributed within the powder 1. The powder 1 and the monomer liquid 2 are contained in a cartridge 50, wherein the powder 1 is arranged in a front part of the interior of the cartridge 50 and the monomer liquid 2 is arranged in a rear part of the interior of the cartridge 50. Together, the rear interior and the front interior delimit a cylindrical interior of the cartridge 50.

A conveying piston 5 is arranged at the rear side of the device (to the right in FIG. 9 and towards the top right-hand corner at the rear in FIGS. 10 and 11) and can be advanced linearly in the axial direction in the interior of the cartridge 50 in the direction of the front side of the device (to the left in FIG. 9 and towards the bottom left-hand corner at the front in FIGS. 10 and 11), or is mounted movably in said direction. The conveying piston 5 closes off the rear side of the interior of the cartridge 50. A discharge piston 6 is arranged in the rear end of the front interior, or in the connection from the front interior to the rear interior of the cartridge 50, and can be advanced linearly in the axial direction in the interior of the cartridge 50 in the direction of the front side of the device, or is mounted movably in said direction. The discharge piston 6 is thus arranged between the powder 1 and the monomer liquid 2 in the interior of the cartridge 50.

A closure system is arranged at the front side of the device, with which closure system the interior of the cartridge 50 is closed off towards the front, however the closure system can be opened in order to discharge a bone cement dough 44 mixed from the starting components 1, 2 (see FIGS. 9 E and 9 F). A wall 7 of the closure system has a central circular discharge opening and is arranged movably in the axial direction of the front interior of the cartridge 50. The discharge opening is delimited by an inner ring. The wall 7 is constructed in the manner of a wheel with an outer ring, which is connected to the inner ring, delimiting the discharge opening, by means of a plurality of struts, which is illustrated suggestively in FIG. 11. The inner ring, the outer ring, and the struts are made in one part from plastic. The closure system also includes a stopper 54, with which the discharge opening is closed in the starting state, as is illustrated in FIG. 9A and FIG. 11.

The monomer liquid 2 is contained in a closed ampoule 9 as container 9 for the monomer liquid 2. The ampoule 9 is made of glass or of a plastic which is chemically resistant to the monomer liquid 2. The monomer liquid 2 can be stored for a long time within the ampoule 9 in the device.

The closure system of the device is arranged in a cartridge head 10, which delimits the front region of the front interior of the cartridge 50. More precisely, the cartridge head 10 is part of the cartridge 50. A ventilation opening is provided in the cartridge head 10 at the front side and is closed by a cap 12 in the storage state or in the starting state of the device. The interior of the cartridge 50 can be gassed with a sterilising gas, such as ethylene oxide, through the ventilation opening, and the content of the cartridge 50 can thus be sterilised. Four ventilation openings 56 are provided in the wall at the rear end of the cartridge 50 directly next to the position of the conveying piston 5, which four ventilation openings connect the interior of the cartridge 50 to the surrounding environment and through which openings the interior of the cartridge 50 can be gassed with the sterilising gas from outside. In the event of a movement of the conveying piston 5 in the direction of the cartridge head 10, these rear-side ventilation openings 56 are closed by the conveying piston 5, so that none of the monomer liquid 2 escaping from the ampoule 9 can pass outwardly from the rear part of the interior. The sterilising gas can thus be conducted through the front ventilation opening in the cartridge head 10 and through the rear ventilation openings 56 through the cartridge 50.

The gaps open between the struts of the wall 7 of the closure system are covered by a filter 16 in the form of a punched disc, which is gas-permeable, but impermeable for the powder 1 and the bone cement dough 44. The wall 7 is thus permeable for gases such as ethylene oxide, but impermeable for the powder 1 and the bone cement dough 44. The wall 7 is formed by a framework in the form of the outer ring with the spokes extending radially inwardly towards the discharge opening and is thus permeable if the gaps thereof are not covered by the filter 16. The structure of the wall 7 can be seen most clearly in FIG. 11, but corresponds to the structure of the walls according to the first two exemplary embodiments.

A discharge tube 18, through which the bone cement dough 44 is applied with use of the device (see FIG. 9 F), is formed in one part with the wall 7 and is arranged at the discharge opening or at the inner ring of the wall 7 delimiting the discharge opening. The discharge tube 18 thus opens out into the discharge opening in the interior of the cartridge 50. The discharge tube 18 is arranged movably with the wall 7 in a feedthrough in the cartridge head 10. The powder 1 can thus be compressed in the front part of the interior of the cartridge 50 with the aid of the wall 7, in that the wall 7 is pushed into the interior of the cartridge 50 with the aid of the discharge tube 18. The discharge tube 18 is held against a retraction by means of a press fit with the feedthrough in the cartridge head 10. The discharge tube 18 is held against a retraction by means of lugs 19 in the feedthrough and a plurality of grooves in the cartridge head 10 arranged externally one above the other in the discharge tube 18. The discharge tube 18 is mounted movably in the longitudinal direction by means of a feedthrough in the cartridge head 10 (that is, in the axial direction of the cylindrical interior of the cartridge 50). By means of the lugs 19 and the grooves, the discharge tube and therefore the wall 7 can be pressed into the cartridge 50 to different depths in different positions, and a pressure can thus be exerted onto the powder 1. The powder 1 is pressed under pressure into the front part of the interior of the cartridge 50 between the wall 7 with the filter 16 and the discharge piston 6 and is under a resilient mechanical pressure. By locking the grooves with the lugs 19 in the feedthrough, it should be possible to prevent the resilient pressure exerted by the compressed powder 1 onto the wall 7 with the filter 16 from being strong enough to push the wall 7 with the filter 16 in the direction of the front side of the cartridge 50 or against the front side of the interior delimited by the cartridge head 10 and thus relieve the powder 1 of pressure again. The wall 7 is sealed with respect to the inner wall of the cartridge 50 by means of a peripheral seal 32. In addition, the connection between the screwed-on cartridge head 10 and the cartridge 50 is sealed by means of a peripheral ring seal 60. The seal 60 prevents bone cement dough 44 from being pressed outwardly between the cartridge head 10 and the cartridge 50.

The stopper 54 by means of which the discharge opening is closed is inserted in the discharge tube 18 and thus closes the cartridge 50 outwardly. The stopper 54 is arranged movably in the discharge tube 18 and can be pushed out from the discharge tube 18 from inside.

The wall 7 with the filter 16 and the stopper 54 held movably relative thereto form a closure system for the device according to one embodiment according to the third exemplary embodiment.

A pore filter 20 impermeable for the powder 1, but permeable for the monomer liquid 2 is arranged on the side of the discharge piston 6 pointing towards the powder 1. The powder 1 should thus be prevented from being able to be advanced through passageways 22, which are provided in the discharge piston 6, into the rear part of the interior of the cartridge 50. Here, the pore filter 20 covers the passageways 22, so that the powder 1 also cannot be advanced into the passageways 22. The monomer liquid 2 is hereby prevented from reacting prematurely with cement powder particles of the powder 1 already when the ampoule 9 has been opened, that is, before the monomer liquid 2 has been pressed into the front part of the interior. It is thus possible to prevent the passageways 22 from being blocked by swelling bone cement and thus preventing any further introduction of monomer liquid 2 into the powder 1.

On the side of the discharge piston 6 opposite the pore filter 20, there is arranged a mesh 24 or sieve 24, by means of which fragments 62 of the broken ampoule 9 are prevented from passing into the passageways 22. It should also be ensured hereby that the monomer liquid 2 from the rear part of the interior of the cartridge 50 can be pushed without difficulty into the powder 1. When the ampoule 9 is broken open, an ampoule head 26 is firstly broken off and the ampoule 9 thus opened (see FIG. 9 B). The monomer liquid 2 from the ampoule 9 can then flow out into the front part of the interior of the cartridge 50 and can then be pressed through the passageways 22 into the powder 1 (see FIG. 9 C). Here, the ampoule 9 is shattered into fragments 62 that are so small that they fit into a cavity formed on the side of the discharge piston 6 facing towards the cartridge base (to the right in FIG. 9 and in the top right-hand corner at the rear in FIGS. 10 and 11). A retainer 36 for fastening a press-out apparatus 40 (see FIG. 9) is provided externally on the cartridge 50 at the cartridge base.

A plurality of hooks 38 are provided as detent means laterally on the discharge piston 6 and engage in a matching groove in the wall of the interior of the cartridge 50. The resultant latching of the discharge piston 6 to the cartridge 50 is strong enough to resist the pressure of the forces occurring as the ampoule 9 is shattered and the pressure of the monomer liquid 2 as the conveying piston 5 is advanced forwards and to withstand the pressure that is exerted by the powder 1 onto the discharge piston 6 by means of the pressed-in wall 7. Only when the conveying piston 5 bears directly against the discharge piston 6 (see FIG. 9 C) is the latched connection released, or are the hooks 38 deformed and slide from the groove in the wall of the interior of the cartridge 50, and the discharge piston 6 is then pushed by the conveying piston 5 in the direction of the cartridge head 10 at the front side of the device.

A filling material (not illustrated), such as a foam material insert and/or plastic beads or grains, can in one embodiment be provided in the cavity in the discharge piston 6 formed in the rear side of the discharge piston 6. The volume of the monomer liquid 2 which remains in this cavity and cannot be pressed by the conveying piston 5 into the powder 1 shall thus be kept as small as possible. Furthermore, this filling material can be used as transport protection and shock protection for the ampoule 9, so that the ampoule 9, as the device is transported in the starting state (see FIGS. 9 A and 11), does not accidentally fracture. To this end, a compressible foam material can be additionally arranged around the ampoule 9 in the interior of the cartridge 50.

The sequence of an exemplary method according to one embodiment is illustrated in FIG. 9 by six cross-sectional views (FIG. 9 A to FIG. 9 F) illustrated one above the other. The device is firstly inserted into a press-out apparatus 40, for which purpose the cartridge 50 is fastened by means of the retainer 36 to a matching counterpiece 41 of the press-out apparatus 40 (see FIG. 9 A).

A ram 42 of the press-out apparatus 40 is then advanced relative to the counterpiece 41. The ram 42 bears against the conveying piston 5. The conveying piston 5 is thus pushed by the ram 42 in the direction of the discharge piston 6. By means of the movement of the conveying piston 5, the ampoule 9 is pushed relative to the discharge piston 6 locked by means of the detent means 38. The ampoule head 26 breaks off, and the ampoule 9 is opened (see FIG. 9 B).

The device in the press-out apparatus 40 is in one embodiment held here with the cartridge head 10 upwardly, so that, as the conveying piston 5 continues to be advanced further forwards, the air arranged at the top is pushed outwardly from the rear part of the interior upwardly through the powder 1 and through the gas-permeable filter 16. The monomer liquid 2 from the ampoule 9 is eventually pushed by the conveying piston 5 through the mesh 24 and/or the sieve 24, through the passageways 22 and through the pore filter 20 into the front part of the interior into the powder 1. In so doing, the ampoule 9 is further compressed and thus shatters into smaller fragments 62, which ultimately collect in the rear-side cavity of the discharge piston 6. The powder 1 contains a hydrophilic additive, which has a large surface energy with respect to the aqueous monomer liquid 2, which surface energy is greater than that of the bone cement powder. At the same time, the capillary forces on account of the compressed powder 1 are great, since the gaps between the powder particles are small. In addition, the monomer liquid 2 is pressed with pressure into the powder 1. As a result of all of these measures, the monomer liquid 2 is conducted quickly into and through the powder 1 and can spread and distribute fully within the powder 1 before the swelling cement powder particles prevent a further spreading of the monomer liquid 2 in the powder 1. Lastly, the conveying piston 5 contacts the discharge piston 6 (see FIG. 9 C).

The cement powder in the powder 1 reacts with the monomer liquid 2 and forms there the bone cement dough 44. In order to obtain the desired mixing ratio between powder 1 and monomer liquid 2 in the bone cement dough 44, excess monomer liquid 2 can be received at the front side of the cartridge 50 between the porous filter 16 of the wall 7 and the cartridge head 10. The monomer liquid 2 is for this purpose pushed through the porous filter 16, which is impermeable for the powder 1 and the bone cement dough 44. Due to absorption of the excess monomer liquid 2 once the monomer liquid 2 has passed through the powder 1 as far as the wall 7, the bone cement dough 44 is prevented from becoming too runny and thus attaining an undesirable consistency. In addition, in order to avoid a consistency of the bone cement dough 44 that is too thick, the monomer liquid 2 is used in excess, so that the losses by the residues of the monomer liquid 2 remaining between the discharge piston 6 and the conveying piston 5 and also in the passageways 22 of the discharge piston 6 are offset.

Due to a further advancing of the conveying piston 5, the discharge piston 6 is driven in the direction of the cartridge head 10 and the latching or the detent means 38 is released. Due to the movement of the discharge piston 6 in the direction of the cartridge head 10, a pressure is exerted by the bone cement dough 44 onto the wall 7, the filter 16 and the stopper 54 in the discharge opening of the closure system. The bone cement dough 44 cannot flow through the filter 16, and therefore the pressure of the bone cement dough 44 acts on the filter 16 and the wall 7.

Since the wall 7, the filter 16 and the discharge tube 18 are initially mounted movably relative to the cartridge 50 or the cartridge head 10 following the release of the locking between the lugs 19 and the grooves in the outer periphery of the discharge tube 18, these parts of the closure system are pushed forwards together with the stopper 54 until the wall 7 bears against the cartridge head 10 from inside and is thus fixed relative to the cartridge head 10 and therefore the cartridge 50 (see FIG. 9 D). If the wall 7 thus bears against the cartridge head 10 from the inside, it is said to be fixed relative to the cartridge 50 within the sense of the present patent application. The stopper 54 is fixedly inserted in the discharge tube 18 in such a way that the pressure of the bone cement dough 44 is not sufficient to move the stopper 54 relative to the discharge tube 18 if it is already sufficient to displace the closure system 7, 16, 54 as a whole in the direction of the cartridge head 10. In other words, the pressure of the bone cement dough 44 necessary to move the wall 7 relative to the cartridge 50, or to overcome the static friction of the wall 7 relative to the cartridge 50, is lower than the pressure of the bone cement dough 44 necessary to move the stopper 54 relative to the wall 7 and the discharge tube 18, or to overcome the static friction of the stopper 54 relative to the discharge tube 18.

As soon as the wall 7 bears against the cartridge head 10 from the inside and the conveying piston 5 together with the discharge piston 6 bearing thereagainst is advanced further in the direction of the cartridge head 10, the stopper 54 is pushed forward out from the discharge tube 18 (see FIG. 9 E). Whereas the wall 7, which bears fixedly against the front side of the cartridge 50 by means of the contact pressure of the bone cement dough 44, thus is not moved with the bone cement dough 44, the stopper 54 is moved relative to the wall 7 and is thus driven out from the discharge opening, and the discharge opening in the wall 7 is thus opened. Lastly, the stopper 54 falls forward out from the discharge tube 18, and the bone cement dough 44 exits from the discharge tube 18. The cartridge 50 is now opened outwardly. By further advancing the conveying piston 5 and therefore the discharge piston 6, the finished bone cement dough 44 is pressed outwardly through the discharge opening and the discharge tube 18 and can be applied (see FIG. 9 F).

On account of the additive provided in the powder 1, it is possible to press in the monomer liquid 2 at one end face of the front part of the cylindrical interior of the cartridge 50 and nevertheless achieve a complete distribution of the monomer liquid 2 in the powder 1. Due to the structure according to one embodiment of the device, it is possible to be able to use a conventional press-out apparatus 40 and, by means of a unidirectional linear movement of the ram 42, to open the container 9 for the monomer liquid 2, to press the monomer liquid 2 into the powder 1 and thus mix the bone cement dough 44, as well as to open the closure system and expel and apply the mixed bone cement dough 44. With the structure according to one embodiment of the closure system, it is possible to be able to use the force exerted by the ram 42 onto the conveying piston 5 in order to open the discharge opening 48.

Figure 14:
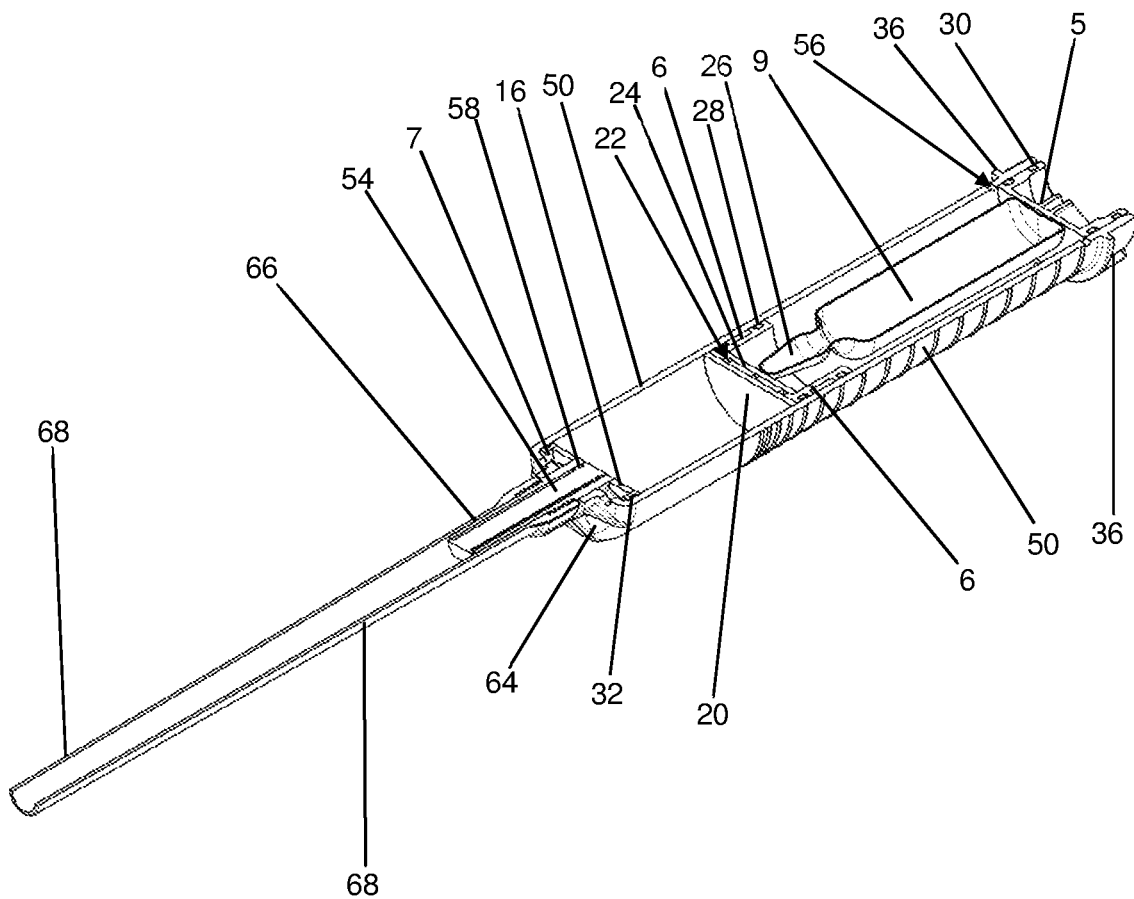
FIG. 14 is a schematic perspective cross-sectional view of a fourth exemplary device according to one embodiment in the starting state.
Figure 15:
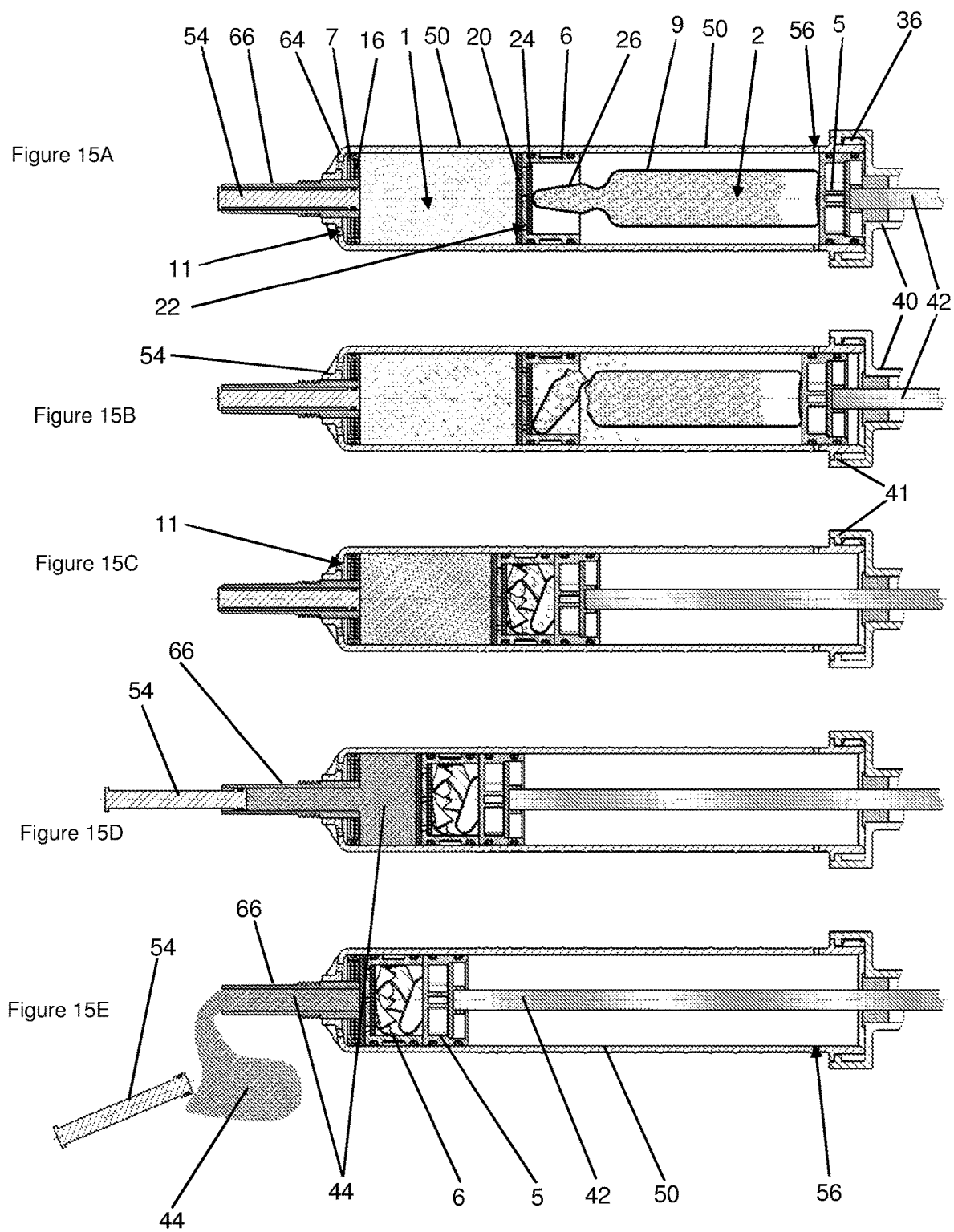
FIGS. 15A-E are five schematic cross-sectional views of the fourth exemplary device, which illustrate the sequence of the use of the device during the production and application of the bone cement dough.
Figure 16:
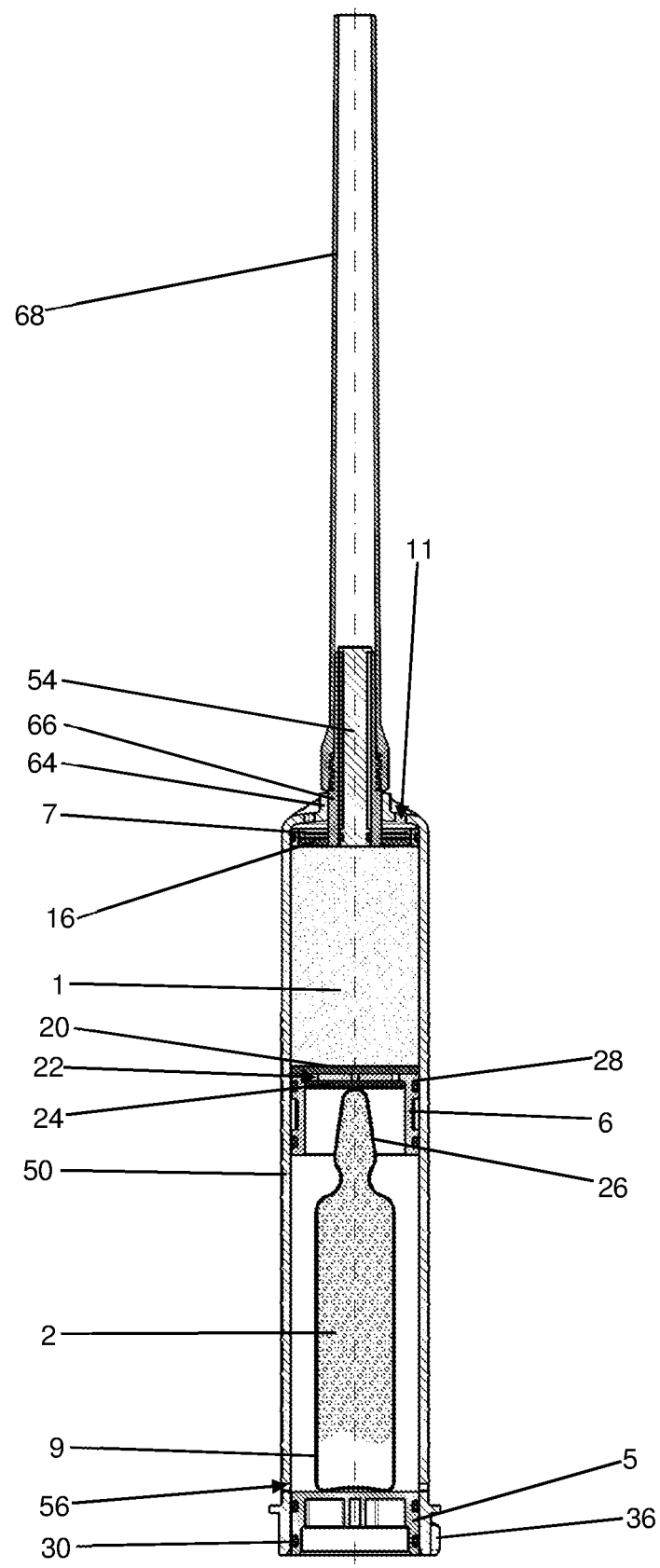
FIG. 16 is a schematic cross-sectional view of the fourth exemplary device according to one embodiment according to FIGS. 14 and 15 with one-part cartridge and extension tube in the starting state.

A fourth exemplary device according to one embodiment is illustrated in FIGS. 14 to 16 and differs from the first exemplary device according to FIGS. 1 to 5 in that the fourth exemplary device, similarly to the second and third exemplary device, has a cartridge 50 which does not consist of two cartridge parts, wherein here, in contrast to the second and third embodiment, a cartridge head 64 of the cartridge 50 is formed in one part with the cartridge 50. The fourth exemplary device, similarly to the second exemplary device according to FIGS. 6 to 8, also has a discharge piston 6, which in the interior of the cartridge 50 is not connected to the cartridge 50 via a detent means. A further difference from the first and second exemplary embodiment is that the closure system, similarly to the third embodiment, is formed with a movable stopper 54, wherein, in contrast to the third embodiment, a wall 7, in which a central discharge opening is provided, is arranged bearing against the front side of the cartridge 50 already in the starting state, and is thus fixed.

Here, FIG. 14 illustrates a perspective cross-sectional view of the device in the starting state, FIG. 15 illustrates five schematic cross-sectional views A to E of the fourth exemplary device with the alternative closure system, which illustrate the sequence of the use of the device during the production and application of the bone cement dough 44, and FIG. 16 illustrates a schematic cross-sectional view of the device in the starting state.

The structure and operating principle of the fourth exemplary device correspond largely to those of the second exemplary device, so that reference can also be made largely to the description of the Figures illustrating the other exemplary embodiments. For example, the used powder 1 and the fundamental operating principle of the two pistons 5, 6 are identical to the second embodiment.

In the starting state of the device, the powder 1 is contained in the device as one starting component of a PMMA bone cement and a monomer liquid 2 is contained in the device as further starting component of the PMMA bone cement. The powder 1 contains a bone cement powder as main constituent and also a hydrophilic additive, by means of which the monomer liquid 2 can be distributed within the powder 1. The powder 1 and the monomer liquid 2 are contained in a cartridge 50, wherein the powder 1 is arranged in a front part of the interior of the cartridge 50 and the monomer liquid 2 is arranged in a rear part of the interior of the cartridge 50. Together, the rear interior and the front interior delimit a cylindrical interior of the cartridge 50.

A conveying piston 5 is arranged at the rear side of the device (towards the top right-hand corner at the rear in FIG. 14, to the right in FIG. 15, and at the bottom in FIG. 16) and can be advanced linearly in the axial direction in the interior of the cartridge 50 in the direction of the front side of the device (towards the bottom left-hand corner at the front in FIG. 14, to the left in FIG. 15, and at the top in FIG. 16), or is mounted movably in said direction. The conveying piston 5 closes off the rear side of the interior of the cartridge 50. A discharge piston 6 is arranged in the rear end of the front interior, or in the connection from the front interior to the rear interior of the cartridge 50, and can be advanced linearly in the axial direction in the interior of the cartridge 50 in the direction of the front side of the device, or is mounted movably in said direction. The discharge piston 6 is thus arranged between the powder 1 and the monomer liquid 2 in the interior of the cartridge 50.

A closure system is arranged at the front side of the device, with which closure system the interior of the cartridge 50 is closed off towards the front, however the closure system can be opened in order to discharge a bone cement dough 44 mixed from the starting components 1, 2 (see FIGS. 15 D and 15 E). The wall 7 of the closure system has a central circular discharge opening and bears against the inner side of the cartridge head 64 in the axial direction of the front interior of the cartridge 50. The discharge opening is delimited by an inner ring. The wall 7 is constructed in the manner of a wheel with an outer ring, which is connected to the inner ring, delimiting the discharge opening, by means of a plurality of struts, which is illustrated suggestively in FIG. 14. The inner ring, the outer ring, and the struts are made in one part from plastic. The closure system also includes a stopper 54, with which the discharge opening is closed in the starting state, as is illustrated in FIG. 14, FIG. 15 A, and FIG. 16.

The monomer liquid 2 is contained in a closed ampoule 9 as container 9 for the monomer liquid 2. The ampoule 9 is made of glass or of a plastic which is chemically resistant to the monomer liquid 2. The monomer liquid 2 can be stored for a long time within the ampoule 9 in the device.

The closure system of the device is arranged in the cartridge head 64, which delimits the front region of the front interior of the cartridge 50. The cartridge head 64 is part of the cartridge 50. A ventilation opening 11 is provided in the cartridge head 10 at the front side. The ventilation opening 11 can be closed by a closure in the storage state or in the starting state of the device. The interior of the cartridge 50 can be gassed with a sterilising gas, such as ethylene oxide, through the ventilation opening 11, and the content of the cartridge 50 can thus be sterilised. A plurality of ventilation openings 56 are provided in the wall at the rear end of the cartridge 50 directly next to the position of the conveying piston 5, which ventilation openings connect the interior of the cartridge 50 to the surrounding environment and through which openings the interior of the cartridge 50 can be gassed with the sterilising gas from outside. In the event of a movement of the conveying piston 5 in the direction of the cartridge head 64, these rear-side ventilation openings 56 are closed by the conveying piston 5, so that none of the monomer liquid 2 escaping from the ampoule 9 can pass outwardly from the rear part of the interior. The sterilising gas can thus be conducted through the front ventilation opening 11 in the cartridge head 64 and through the rear ventilation openings 56 through the cartridge 50.

The gaps open between the struts of the wall 7 of the closure system are covered by a filter 16, which is gas-permeable, but impermeable for the powder 1 and the bone cement dough 44. The wall 7 is thus permeable for gases such as ethylene oxide, but impermeable for the powder 1 and the bone cement dough 44. The wall 7 is formed by a framework in the form of the outer ring with the spokes extending radially inwardly towards the discharge opening and is thus permeable if the gaps thereof are not covered by the filter 16. The structure of the wall 7 can be seen most clearly in FIG. 14, but corresponds to the structure of the walls according to the first two exemplary embodiments.

A discharge tube connection piece 66 with an external thread, through which the bone cement dough 44 is applied with use of the device (see FIG. 15 E), is formed in one part with the wall 7 and is arranged at the discharge opening or at the inner ring of the wall 7 delimiting the discharge opening. The discharge tube connection piece 66 thus opens out into the discharge opening in the interior of the cartridge 50. A discharge tube extension 68, by means of which bone cement dough 44 can be applied in regions that are difficult to access, can be screwed onto the discharge tube connection piece 66. The discharge tube connection piece 66 is arranged with the wall 7 in a feedthrough in the cartridge head 10 and theoretically can also be fixedly connected to the cartridge head 64. The powder 1 can be compressed in the front part of the interior of the cartridge 50 with the aid of the discharge piston 6, in that the discharge piston 6 is pushed into the interior of the cartridge 50 in the direction of the cartridge head 64. The discharge piston 6 is held against a retraction by means of a fit with the wall of the interior of the cartridge 50 and/or is held supported by the ampoule 9 and the conveying piston 5 in the cartridge 50. The powder 1 is pressed under pressure into the front part of the interior of the cartridge 50 between the wall 7 with the filter 16 and the discharge piston 6 and is under a resilient mechanical pressure. By means of the fit of the discharge piston 6 with the inner wall of the cartridge 50 and/or the support with the ampoule 9 and the conveying piston 5, it should be possible to prevent the resilient pressure exerted by the compressed powder 1 onto the discharge piston 6 from being strong enough to move the discharge piston 6 and relieve the powder 1 of pressure again. The wall 7 is sealed with respect to the inner wall of the cartridge 50 by means of a peripheral seal 32.

The stopper 54 by means of which the discharge opening is closed is inserted in the discharge tube connection piece 66 and thus closes the cartridge 50 outwardly. The stopper 54 is arranged movably in the discharge tube connection piece 66 and can be pushed out from the discharge tube connection piece 66 from inside.

The wall 7, which bears against the cartridge head 64 from the inside and is thus fixed with the cartridge 50, with the filter 16 and the stopper 54 held movably relative thereto form a closure system for the device according to one embodiment according to the fourth exemplary embodiment.

A pore filter 20 impermeable for the powder 1, but permeable for the monomer liquid 2 is arranged on the side of the discharge piston 6 pointing towards the powder 1. The powder 1 should thus be prevented from being able to be advanced through passageways 22, which are provided in the discharge piston 6, into the rear part of the interior of the cartridge 50. Here, the pore filter 20 covers the passageways 22, so that the powder 1 also cannot be advanced into the passageways 22. The monomer liquid 2 is hereby prevented from reacting prematurely with cement powder particles of the powder 1 already when the ampoule 9 has been opened, that is, before the monomer liquid 2 has been pressed into the front part of the interior. It is thus possible to prevent the passageways 22 from being blocked by swelling bone cement and thus preventing any further introduction of monomer liquid 2 into the powder 1.

On the side of the discharge piston 6 opposite the pore filter 20, there is arranged a mesh 24 or sieve 24, by means of which fragments of the broken ampoule 9 are prevented from passing into the passageways 22. It should also be ensured hereby that the monomer liquid 2 from the rear part of the interior of the cartridge 50 can be pushed without difficulty into the powder 1. When the ampoule 9 is broken open, an ampoule head 26 is firstly broken off and the ampoule 9 thus opened (see FIG. 15 B). The monomer liquid 2 from the ampoule 9 can then flow out into the front part of the interior of the cartridge 50 and can then be pressed through the passageways 22 into the powder 1 (see FIG. 15 C). Here, the ampoule 9 is shattered into fragments that are so small that they fit into a cavity formed on the side of the discharge piston 6 facing towards the cartridge base (towards the top right-hand corner at the rear in FIG. 14, to the right in FIG. 15, and towards the bottom in FIG. 16).

A retainer 36 for fastening a press-out apparatus 40 (see FIG. 15) is provided externally on the cartridge 50 at the cartridge base.

The stopper 54 is fitted so firmly in the discharge tube connection piece 66 that it is not moved by the forces occurring as the ampoule 9 is shattered, so as to withstand the pressure of the monomer liquid 2 as the conveying piston 5 is advanced forwards and to withstand the pressure that is exerted by the powder 1 onto the discharge piston 6 by means of the pressed-in wall 7. Air displaced as the monomer liquid 2 is introduced and as the conveying piston 5 is advanced forwards can escape through the ventilation openings 11. Only when the conveying piston 5 bears directly against the discharge piston 6 (see FIG. 15 C) is the static friction between the stopper 54 and the discharge tube connection piece 64 overcome and the stopper 54 pushed from the discharge tube connection piece 66 and the cartridge 50 for the bone cement dough 44 thus opened outwardly.

A filling material (not illustrated), such as a foam material insert and/or plastic beads or grains, can in one embodiment be provided in the cavity in the discharge piston 6 formed in the rear side of the discharge piston 6. The volume of the monomer liquid 2 which remains in this cavity and cannot be pressed by the conveying piston 5 into the powder 1 shall thus be kept as small as possible. Furthermore, this filling material can be used as transport protection and shock protection for the ampoule 9, so that the ampoule 9, as the device is transported in the starting state (see FIGS. 1 and 2), does not accidentally fracture. To this end, a compressible foam material can be additionally arranged around the ampoule 9 in the interior of the cartridge 50.

The sequence of an exemplary method according to one embodiment is illustrated in FIG. 15 by five cross-sectional views (FIG. 15 A to FIG. 15 E) illustrated one above the other. The device is firstly inserted into a press-out apparatus 40, for which purpose the cartridge 50 is fastened by means of the retainer 36 to a matching counterpiece 41 of the press-out apparatus 40 (see FIG. 15 A).

A ram 42 of the press-out apparatus 40 is advanced relative to the cartridge 50 following the insertion of the device. The ram 42 bears against the conveying piston 5. The conveying piston 5 is thus pushed by the ram 42 in the direction of the discharge piston 6. By means of the movement of the conveying piston 5, the ampoule 9 is pushed relative to the discharge piston 6 held by the pressed powder 1 and the cartridge head 64. The ampoule head 26 breaks off, and the ampoule 9 is opened (see FIG. 15 B).

The device in the press-out apparatus 40 is in one embodiment held here with the cartridge head 64 upwardly, so that, as the conveying piston 5 continues to be advanced further forwards, the air arranged at the top is pushed outwardly from the rear part of the interior upwardly through the powder 1, through the gas-permeable filter 16, and through the ventilation openings 11. The monomer liquid 2 from the ampoule 9 is eventually pushed by the conveying piston 5 through the mesh 24 and/or the sieve 24, through the passageways 22 and through the pore filter 20 into the front part of the interior into the powder 1. In so doing, the ampoule 9 is further compressed and thus shatters into smaller fragments, which ultimately collect in the rear-side cavity of the discharge piston 6. The powder 1 contains a hydrophilic additive, which has a large surface energy with respect to the aqueous monomer liquid 2, which surface energy is greater than that of the bone cement powder. At the same time, the capillary forces on account of the compressed powder 1 are great, since the gaps between the powder particles are small. In addition, the monomer liquid 2 is pressed with pressure into the powder 1. As a result of all of these measures, the monomer liquid 2 is conducted quickly into and through the powder 1 and can spread and distribute fully within the powder 1 before the swelling cement powder particles prevent a further spreading of the monomer liquid 2 in the powder 1. Lastly, the conveying piston 5 contacts the discharge piston 6 (see FIG. 15 C).

The cement powder in the powder 1 reacts with the monomer liquid 2 and forms there the bone cement dough 44. In order to obtain the desired mixing ratio between powder 1 and monomer liquid 2 in the bone cement dough 44, excess monomer liquid 2 can be received at the front side of the cartridge 50 between the porous filter 16 of the wall 7 and the cartridge head 10. The monomer liquid 2 is for this purpose pushed through the porous filter 16, which is impermeable for the powder 1 and the bone cement dough 44. Due to absorption of the excess monomer liquid 2 once the monomer liquid 2 has passed through the powder 1 as far as the wall 7, the bone cement dough 44 is prevented from becoming too runny and thus attaining an undesirable consistency. In addition, in order to avoid a consistency of the bone cement dough 44 that is too thick, the monomer liquid 2 is used in excess, so that the losses by the residues of the monomer liquid 2 remaining between the discharge piston 6 and the conveying piston 5 and also in the passageways 22 of the discharge piston 6 are offset.

Due to a further advancing of the conveying piston 5, the discharge piston 6 is driven in the direction of the cartridge head 64. Due to the movement of the discharge piston 6 in the direction of the cartridge head 64, a pressure is exerted by the bone cement dough 44 onto the stopper 54 in the discharge opening of the closure system.

Since the wall 7 bears against the cartridge head 64 from the inside and therefore cannot move further in the direction of the cartridge had 64 and the conveying piston 5 is advanced forwards in the direction of the cartridge head 64 together with the discharge piston 6 bearing thereagainst, the stopper 54 is pushed out in a forward direction from the discharge tube connection piece 66 (see FIGS. 15 D and 15 E). Whereas the wall 7, which bears fixedly against the front side of the cartridge 50 by means of the contact pressure of the bone cement dough 44, thus is not moved with the bone cement dough 44, the stopper 54 is moved relative to the wall 7 and is thus driven out from the discharge opening, and the discharge opening in the wall 7 is thus opened. Lastly, the stopper 54 falls forward out from the discharge tube connection piece 66, and the bone cement dough 44 exits from the discharge tube connection piece 66. The cartridge 50 is now opened outwardly. By further advancing the conveying piston 5 and therefore the discharge piston 6, the finished bone cement dough 44 is pressed outwardly through the discharge opening and the discharge tube connection piece 66 and can be applied (see FIG. 15 E).

On account of the additive provided in the powder 1, it is possible to press in the monomer liquid 2 at one end face of the front part of the cylindrical interior of the cartridge 50 and nevertheless achieve a complete distribution of the monomer liquid 2 in the powder 1. Due to the structure according to one embodiment of the device, it is possible to be able to use a conventional press-out apparatus 40 and, by means of a unidirectional linear movement of the ram 42, to open the container 9 for the monomer liquid 2, to press the monomer liquid 2 into the powder 1 and thus mix the bone cement dough 44, as well as to open the closure system and expel and apply the mixed bone cement dough 44. With the structure according to one embodiment of the closure system, it is possible to be able to use the force exerted by the ram 42 onto the conveying piston 5 in order to open the discharge opening.

Figure 17:
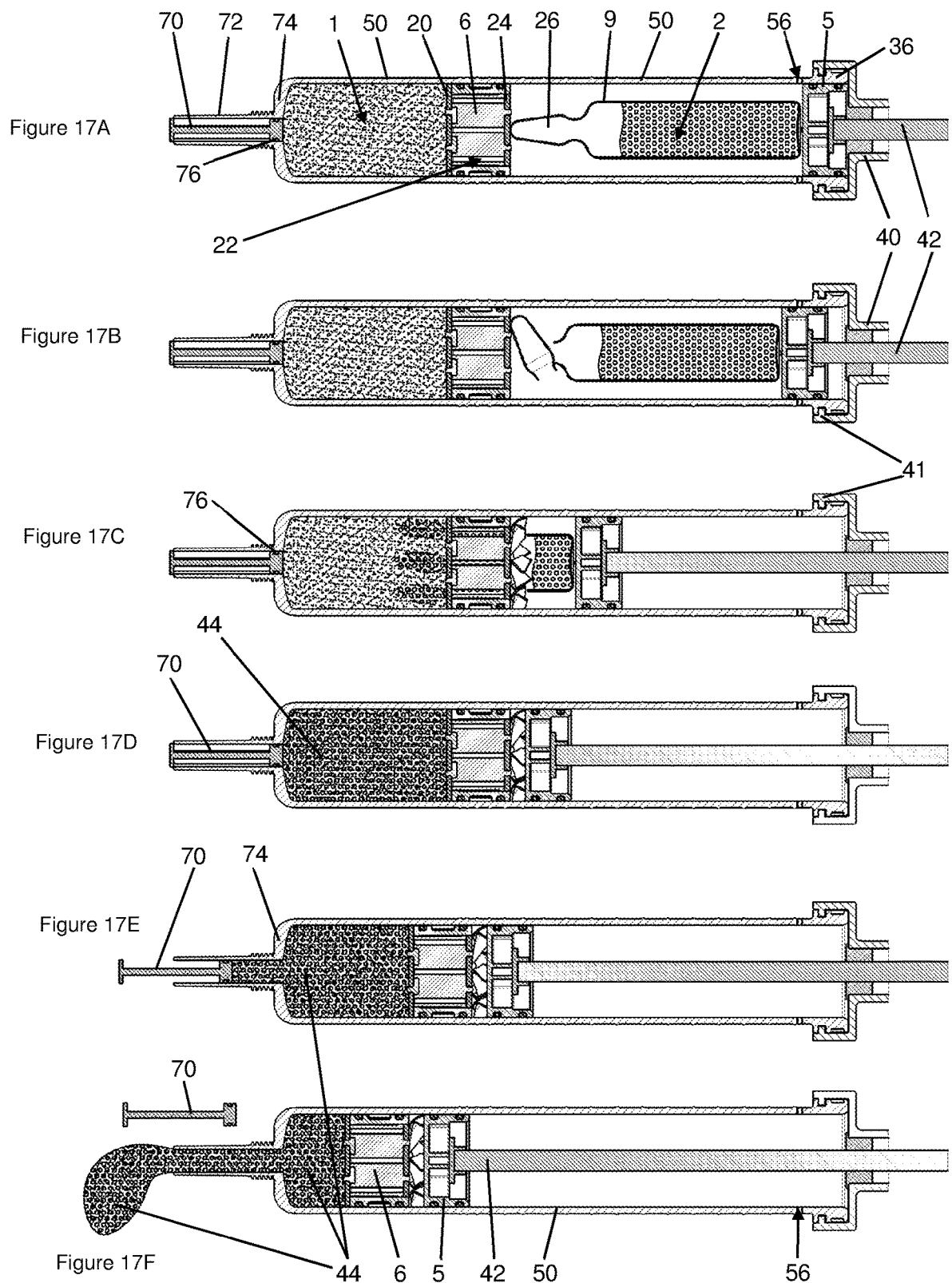
FIGS. 17A-F are six schematic cross-sectional views of a fifth exemplary device, which illustrate the sequence of the use of the device during the production and application of the bone cement dough.
Figure 18:
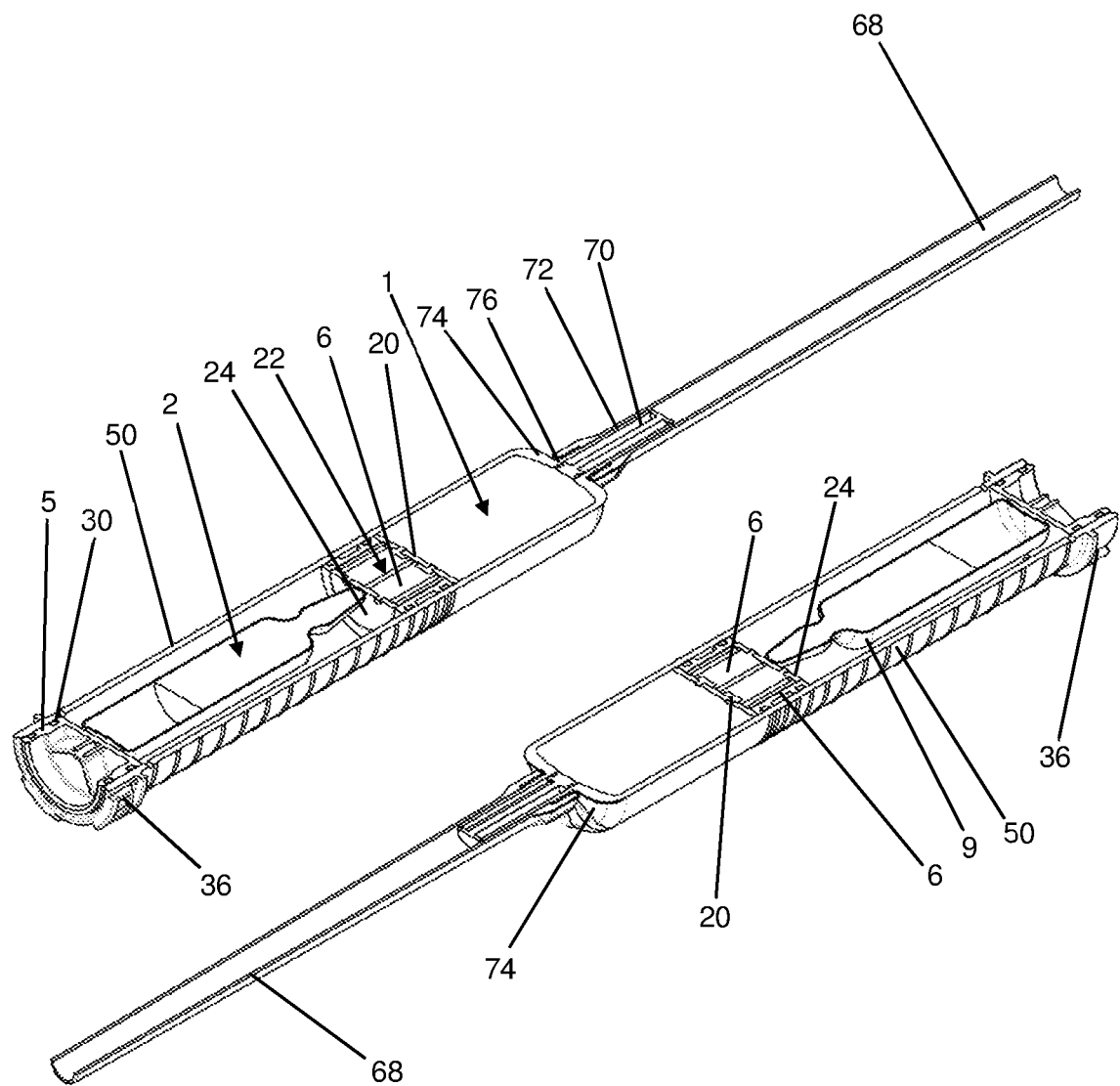
FIG. 18 are two schematic perspective cross-sectional views of the fifth exemplary device according to one embodiment in the starting state.

A fifth exemplary device according to one embodiment is illustrated in FIGS. 17 and 18, which is of a particularly economical structure and differs from the first exemplary device according to FIGS. 1 to 5 in that there is no longer a separate wall 7 provided, and instead the wall 74 is formed by a cartridge head 74 of a cartridge 50 formed in one part from plastic. The fifth exemplary device, similarly to the second, third and fourth exemplary device, thus has a cartridge 50 not consisting of two cartridge parts, wherein here, in contrast to the second and third embodiment and similarly to the fourth embodiment, the cartridge head 74 of the cartridge 50 is also formed in one part with the cartridge 50. The fifth exemplary device, similarly to the second exemplary device according to FIGS. 6 to 8 and the fourth exemplary embodiment according to FIGS. 14 to 16, also has a discharge piston 6, which in the interior of the cartridge 50 is not connected to the cartridge 50 via a detent means. A further difference from the first and second exemplary embodiment is that the closure system, similarly to the third and fourth embodiment, is formed with a movable stopper 70, wherein, in contrast to the third and fourth embodiment, the wall 74, in which a central discharge opening is provided, is formed in one part with the cartridge 50 and is thus always connected to the cartridge 50 and thus fixed.

Here, FIG. 17 illustrates six schematic cross-sectional views A to F of the fifth exemplary device with the simplified structure, which illustrate the sequence of the use of the device during the production and application of the bone cement dough 44, and FIG. 18 illustrates two perspective cross-sectional views of the device in the starting state.

The structure and operating principle of the fifth exemplary device correspond largely to those of the first and fourth exemplary device, so that reference can also be made largely to the description of the Figures illustrating the other exemplary embodiments. For example, the used powder 1 and the fundamental operating principle of the two pistons 5, 6 are identical, apart from the latching of the discharge piston 6 with the inner side of the cartridge 50.

In the starting state of the device, the powder 1 is contained in the device as a starting component of a PMMA bone cement and a monomer liquid 2 is contained in the device as further starting component of the PMMA bone cement. The powder 1 contains a bone cement powder as main constituent and also a hydrophilic additive, by means of which the monomer liquid 2 can be distributed within the powder 1. The powder 1 and the monomer liquid 2 are contained in a cartridge 50, wherein the powder 1 is arranged in a front part of the interior of the cartridge 50 and the monomer liquid 2 is arranged in a rear part of the interior of the cartridge 50. Together, the rear interior and the front interior delimit a cylindrical interior of the cartridge 50.

A conveying piston 5 is arranged at the rear side of the device (to the right in FIG. 17) and can be advanced linearly in the axial direction in the interior of the cartridge 50 in the direction of the front side of the device (to the left in FIG. 17), or is mounted movably in said direction. The conveying piston 5 closes off the rear side of the interior of the cartridge 50. A discharge piston 6 is arranged in the rear end of the front interior, or in the connection from the front interior to the rear interior of the cartridge 50, and can be advanced linearly in the axial direction in the interior of the cartridge 50 in the direction of the front side of the device, or is mounted movably in said direction. The discharge piston 6 is thus arranged between the powder 1 and the monomer liquid 2 in the interior of the cartridge 50.

A closure system is arranged at the front side of the device, with which closure system the interior of the cartridge 50 is closed off towards the front, however the closure system can be opened in order to discharge a bone cement dough 44 mixed from the starting components 1, 2 (see FIGS. 17 D, 17 E and 17 F). The wall 74, which is part of the closure system, has a central circular discharge opening and forms the cartridge head 74 of the cartridge 50. The cartridge 50 is made in one part from plastic together with the wall 74. The closure system also includes the stopper 70, with which the discharge opening is closed in the starting state, as is illustrated in FIG. 17 A and FIG. 18.

The monomer liquid 2 is contained in a closed ampoule 9 as container 9 for the monomer liquid 2. The ampoule 9 is made of glass or of a plastic which is chemically resistant to the monomer liquid 2. The monomer liquid 2 can be stored for a long time within the ampoule 9 in the device.

The closure system of the device is formed by the wall 74 and the stopper 70. So that a gas can escape from the interior of the cartridge 50 as the pistons 5, 6 are advanced towards the wall 74, and so that a sterilising gas can be introduced into the interior of the cartridge 50, the stopper is sealed with a peripheral porous plastic ring 76 with respect to the discharge opening or with respect to the inner wall of the discharge tube 72. The porous plastic ring 76 is permeable for gases and impermeable for the powder 1 and is made of polyethylene. The ventilation opening thus formed is covered in the storage state or in the starting state of the device by a front circular plate of the stopper 70. By displacing the stopper 70 out from the discharge tube 72, this opening can be opened, so as to feed in sterilising gas. The interior of the cartridge 50 can be gassed with a sterilising gas, such as ethylene oxide, through the plastic ring 76, and the content of the cartridge 50 can thus be sterilised. A plurality of ventilation openings 56 are provided in the wall at the rear end of the cartridge 50 directly next to the position of the conveying piston 5, which ventilation openings connect the interior of the cartridge 50 to the surrounding environment and through which openings the interior of the cartridge 50 can be gassed with the sterilising gas from outside. In the event of a movement of the conveying piston 5 in the direction of the wall 74, these rear-side ventilation openings 56 are closed by the conveying piston 5, so that none of the monomer liquid 2 escaping from the ampoule 9 can pass outwardly from the rear part of the interior. The sterilising gas can thus be conducted through the porous plastic ring 76 and through the rear ventilation openings 56 through the cartridge 50.

The discharge tube 72 with an external thread, through which the bone cement dough 44 is applied with use of the device (see FIG. 17 F), is formed in one part with the cartridge 50 and the wall 74 and is arranged at the discharge opening. A discharge tube extension 68 can be screwed onto the external thread on the discharge tube 72 (see FIG. 18), and therefore bone cement dough 44 can be applied in regions that are difficult to access.

The powder 1 can be compressed in the front part of the interior of the cartridge 50 with the aid of the discharge piston 6 by pushing the discharge piston 6 into the interior of the cartridge 50 in the direction of the wall 74. The discharge piston 6 is held against a retraction by means of a fit with the wall of the interior of the cartridge 50 and/or is held supported by the ampoule 9 and the conveying piston 5 in the cartridge 50. The powder 1 is pressed under pressure into the front part of the interior of the cartridge 50 between the wall 74 and the discharge piston 6 and is under a resilient mechanical pressure. By means of the fit of the discharge piston 6 with the inner wall of the cartridge 50 and/or the support with the ampoule 9 and the conveying piston 5, it should be possible to prevent the resilient pressure exerted by the compressed powder 1 onto the discharge piston 6 from being strong enough to move the discharge piston 6 and relieve the powder 1 of pressure again.

The stopper 70 by means of which the discharge opening is closed is inserted in the discharge tube 72 and thus closes the cartridge 50 outwardly. The stopper 70 is arranged movably in the discharge tube 72 and can be pushed out from the discharge tube 72 from inside.

Passageways 22 are provided in the discharge piston 6, through which passageways the monomer liquid 2 can be pressed with the aid of the conveying piston 5 into the powder 1, as is also provided in the other exemplary embodiments. On the side of the discharge piston 6 pointing towards the powder 1, pore filters impermeable for the powder 1, but permeable for the monomer liquid 2 are arranged over the passageways 22 and cover the passageways 22. The powder 1 shall thus be prevented from advancing through the passageways 22 into the rear part of the interior of the cartridge 50 or from advancing into the passageways 22. The monomer liquid 2, once the ampoule 9 has been opened, is thus prevented from already reacting prematurely with cement powder particles of the powder 1, that is, before the monomer liquid 2 has been pressed into the front part of the interior. It is thus possible to prevent the passageways 22 from being blocked by swelling bone cement and thus preventing any further introduction of monomer liquid 2 into the powder 1.

On the side of the discharge piston 6 opposite the pore filters 20, there are arranged meshes 24 fitting in recesses over the passageways 22, by means of which meshes fragments of the broken ampoule 9 are prevented from passing into the passageways 22. It should also be ensured hereby that the monomer liquid 2 from the rear part of the interior of the cartridge 50 can be pushed without difficulty into the powder 1. When the ampoule 9 is broken open, an ampoule head 26 is firstly broken off and the ampoule 9 thus opened (see FIG. 17 B). The monomer liquid 2 from the ampoule 9 can then flow out into the front part of the interior of the cartridge 50 and can then be pressed through the passageways 22 into the powder 1 (see FIG. 17 C). Here, the ampoule 9 is shattered into fragments that are so small that they fit into a cavity formed on the side of the discharge piston 6 facing towards the cartridge base (to the right in FIG. 17).

A retainer 36 for fastening a press-out apparatus 40 (see FIG. 17) is provided externally on the cartridge 50 at the cartridge base.

The stopper 54 is fitted so firmly in the discharge tube 72 that it is not moved by the forces occurring as the ampoule 9 is shattered, so as to withstand the pressure of the monomer liquid 2 as the conveying piston 5 is advanced forwards and to withstand the pressure that is exerted by the powder 1 onto the discharge piston 6. Air displaced as the monomer liquid 2 is introduced and as the conveying piston 5 is advanced forwards can escape through the porous plastic ring 76. Only when the conveying piston 5 bears directly against the discharge piston 6 (see FIG. 17 D) is the static friction between the stopper 54 and the discharge tube 72 overcome and the stopper 54 then pushed from the discharge tube 72 and the cartridge 50 for the bone cement dough 44 thus opened outwardly.

A filling material (not illustrated), such as a foam material insert and/or plastic beads or grains, can in one embodiment be provided in the cavity in the discharge piston 6 formed in the rear side of the discharge piston 6. The volume of the monomer liquid 2 which remains in this cavity and cannot be pressed by the conveying piston 5 into the powder 1 shall thus be kept as small as possible. Furthermore, this filling material can be used as transport protection and shock protection for the ampoule 9, so that the ampoule 9, as the device is transported in the starting state (see FIGS. 17 A and 18), does not accidentally fracture. To this end, a compressible foam material can be additionally arranged around the ampoule 9 in the interior of the cartridge 50.

The sequence of an exemplary method according to one embodiment is illustrated in FIG. 17 by six cross-sectional views (FIG. 17 A to FIG. 17 F) illustrated one above the other. The device is firstly inserted into a press-out apparatus 40, for which purpose the cartridge 50 is fastened by means of the retainer 36 to a matching counterpiece 41 of the press-out apparatus 40 (see FIG. 17 A).

A ram 42 of the press-out apparatus 40 is advanced relative to the cartridge 50 following the insertion of the device. The ram 42 bears against the conveying piston 5. The conveying piston 5 is thus pushed by the ram 42 in the direction of the discharge piston 6. By means of the movement of the conveying piston 5, the ampoule 9 is pushed relative to the discharge piston 6 held by the pressed powder 1 and the wall 74. The ampoule head 26 breaks off, and the ampoule 9 is opened (see FIG. 17 B).

The device in the press-out apparatus 40 is in one embodiment held here with the discharge tube 72 upwardly, so that, as the conveying piston 5 continues to be advanced further forwards, the air arranged at the top is pushed outwardly from the rear part of the interior upwardly through the powder 1, through the gas-permeable filter 16, and through the porous plastic ring 76. The monomer liquid 2 from the ampoule 9 is eventually pushed by the conveying piston 5 through the mesh 24, through the passageways 22 and through the pore filters 20 into the front part of the interior into the powder 1 (see FIG. 17 C). In so doing, the ampoule 9 is further compressed and thus shatters into smaller fragments, which ultimately collect in the rear-side cavity of the discharge piston 6. The powder 1 contains a hydrophilic additive, which has a large surface energy with respect to the aqueous monomer liquid 2, which surface energy is greater than that of the bone cement powder. At the same time, the capillary forces on account of the compressed powder 1 are great, since the gaps between the powder particles are small. In addition, the monomer liquid 2 is pressed with pressure into the powder 1. As a result of all of these measures, the monomer liquid 2 is conducted quickly into and through the powder 1 and can spread and distribute fully within the powder 1 before the swelling cement powder particles prevent a further spreading of the monomer liquid 2 in the powder 1. Lastly, the conveying piston 5 contacts the discharge piston 6 (see FIG. 17 D).

The cement powder in the powder 1 reacts with the monomer liquid 2 and forms there the bone cement dough 44. Due to a further advancing of the conveying piston 5, the discharge piston 6 is driven in the direction of the wall 74. Due to the movement of the discharge piston 6 in the direction of the wall 74, a pressure is exerted by the bone cement dough 44 onto the stopper 54 in the discharge opening of the closure system.

Since the wall 74 is firmly fixed with the cartridge 50 and the conveying piston 5 is advanced forwards in the direction of the wall 74 together with the discharge piston 6 bearing thereagainst, the stopper 54 is pushed out in a forward direction from the discharge tube 72 (see FIGS. 17 E and 17 F). Whereas the wall 74 thus is not moved with the bone cement dough 44, the stopper 54 is moved relative to the wall 74 and is thus driven out from the discharge opening, and the discharge opening in the wall 74 is thus opened. Lastly, the stopper 54 falls forward out from the discharge tube 72, and the bone cement dough 44 exits from the discharge tube 72 or from the discharge tube extension 68 screwed onto the discharge tube 72. The cartridge 50 is now opened outwardly. By further advancing the conveying piston 5 and therefore the discharge piston 6, the finished bone cement dough 44 is pressed outwardly through the discharge opening and the discharge tube 72 and can be applied (see FIG. 17 F).

On account of the additive provided in the powder 1, it is possible to press in the monomer liquid 2 at one end face of the front part of the cylindrical interior of the cartridge 50 and nevertheless achieve a complete distribution of the monomer liquid 2 in the powder 1. Due to the structure of the device according to one embodiment, it is possible to be able to use a conventional press-out apparatus 40 and, by means of a unidirectional linear movement of the ram 42, to open the container 9 for the monomer liquid 2, to press the monomer liquid 2 into the powder 1 and thus mix the bone cement dough 44, as well as to open the closure system and expel and apply the mixed bone cement dough 44. With the structure of the closure system according to one embodiment, it is possible to be able to use the force exerted by the ram 42 onto the conveying piston 5 in order to open the discharge opening.

Figure 19:
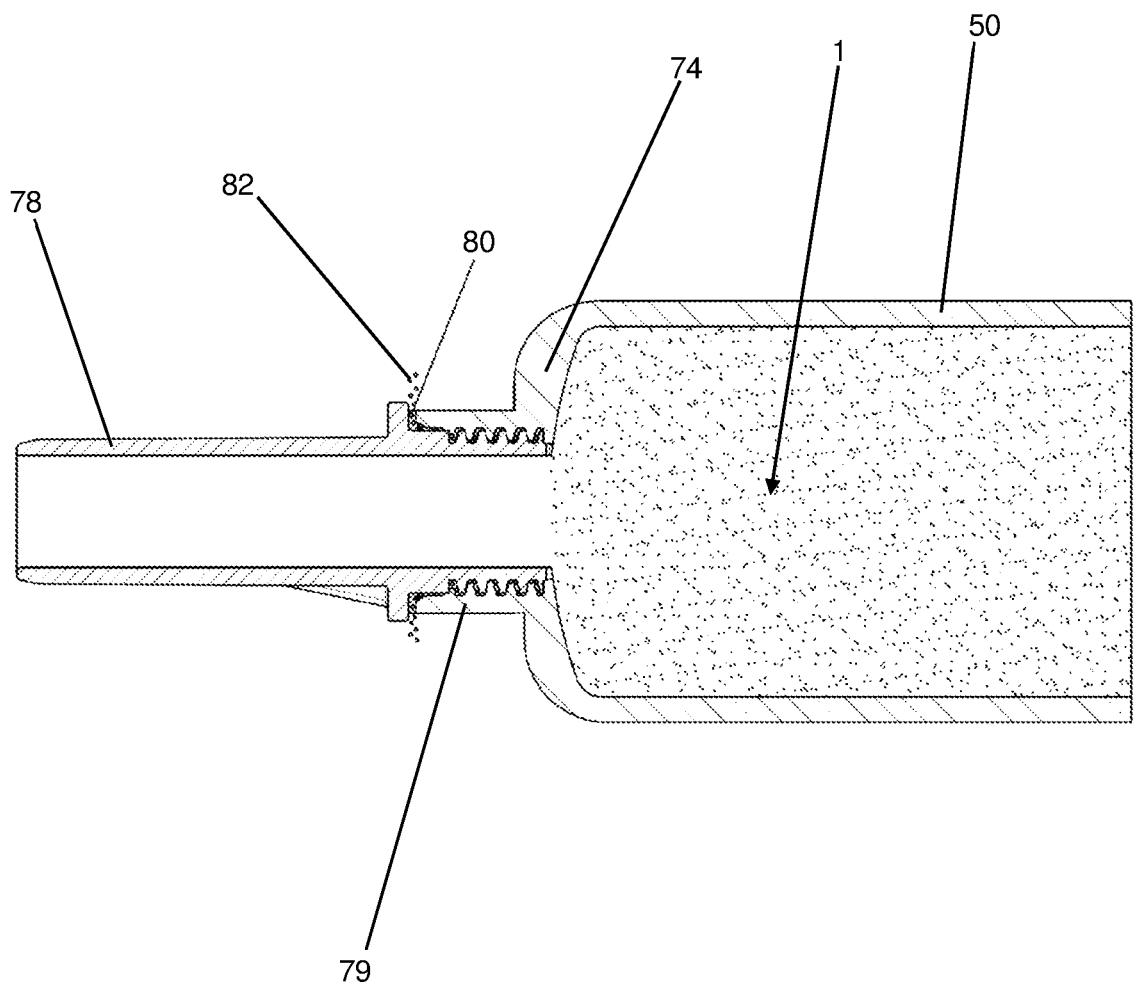
FIG. 19 is an enlarged detail of the front side of a sixth exemplary device in a schematic cross-sectional view.
Figure 20:
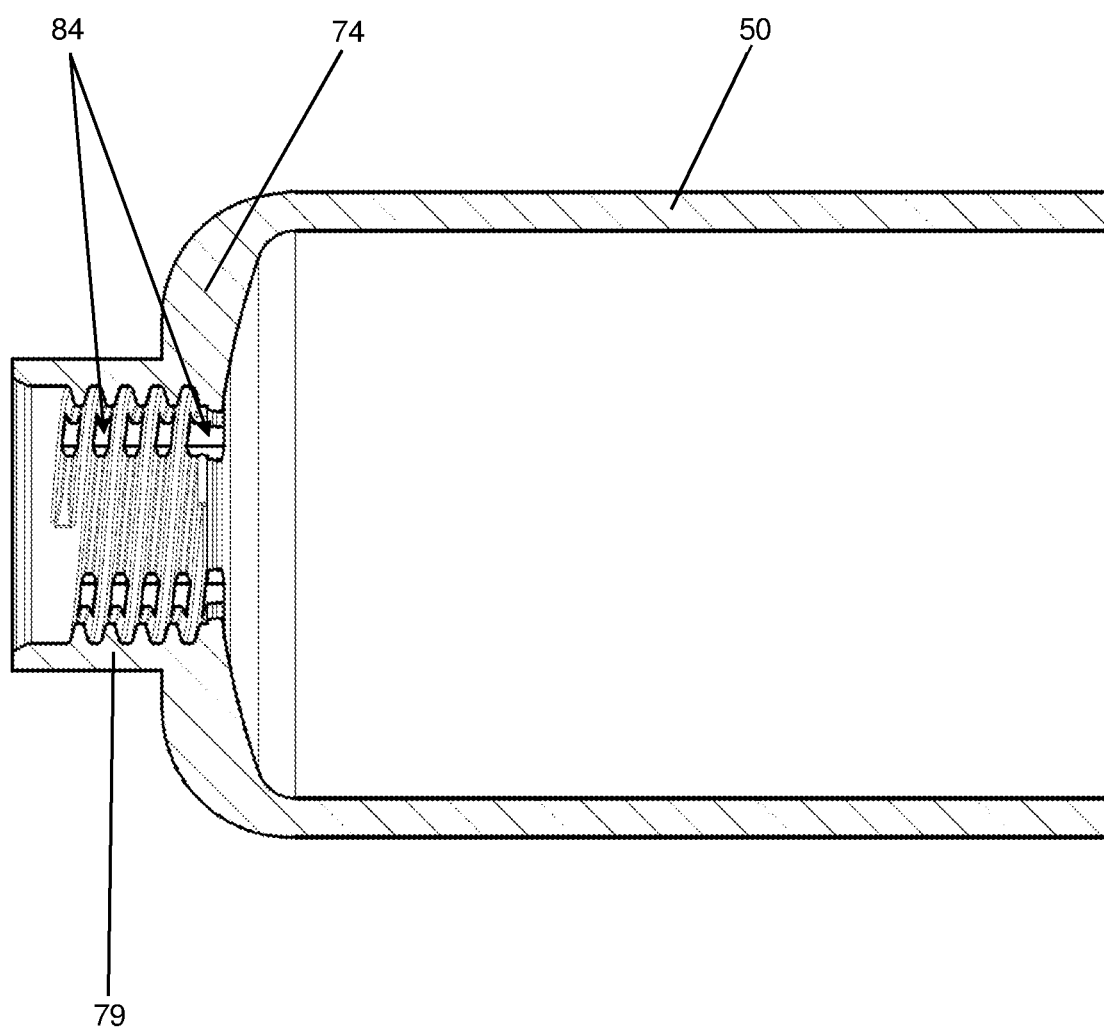
FIG. 20 is a perspective cross-sectional view of the front part of the cartridge of the sixth exemplary device.
Figure 21:
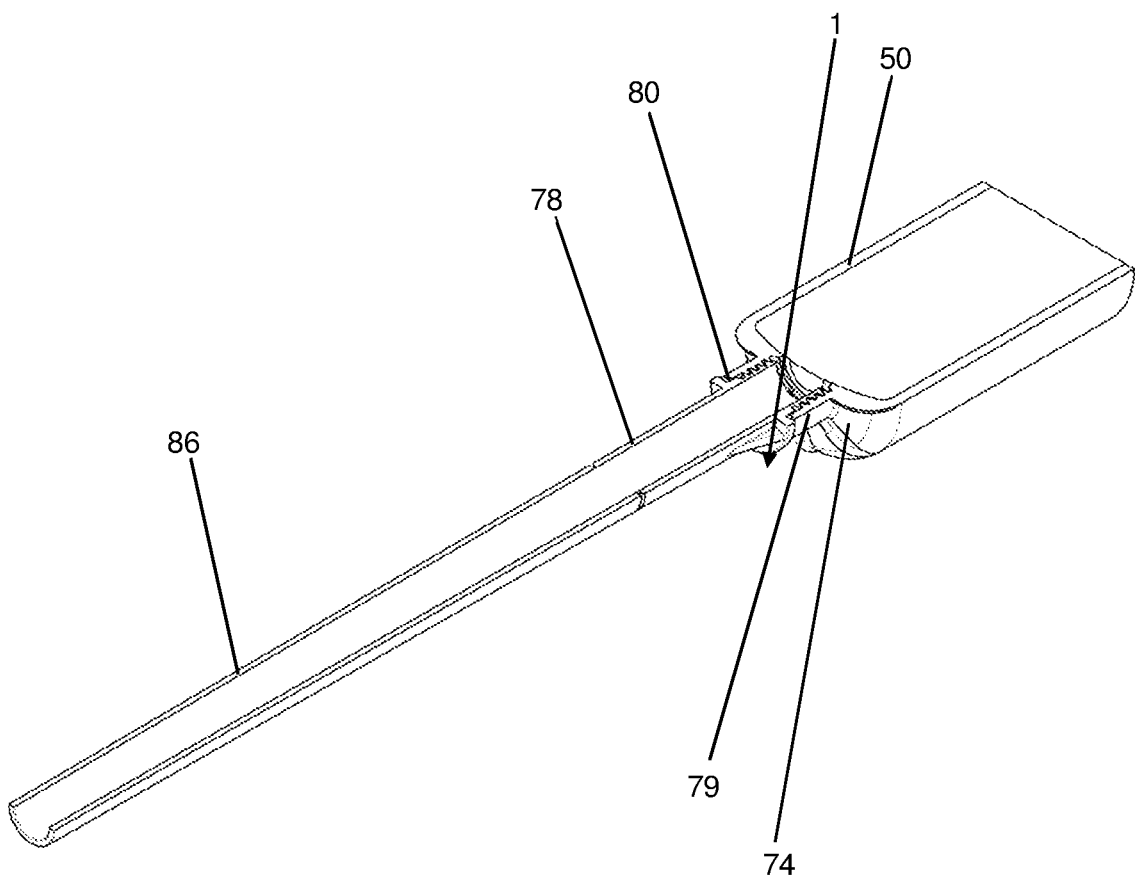
FIG. 21 is a further perspective cross-sectional view of the front part of the cartridge of the sixth exemplary device with a discharge tube extension.

A further variant of a device according to one embodiment is illustrated in FIGS. 19 to 21. Only the front part of the device is illustrated in each of these Figures. The rest of the structure (for example, the discharge piston and the conveying piston) is then identical for example to one of the first five exemplary embodiments.

In both cross-sectional views according to FIGS. 19 and 21, it can be seen that in this embodiment, similarly to the fifth embodiment of the device, a wall 74 is provided, which is formed by the cartridge head 74. A discharge tube 78 is screwed into a connection piece 79. To this end, the connection piece 79 has an internal thread and the discharge tube 78 has an external thread. The connection piece 79 is formed in one part with the wall 74 and the cartridge 50. A porous plastic ring 80 is provided as seal between the discharge tube 78 and the connection piece 79. The porous plastic ring 80 is tight with respect to the powder 1, but permeable relative to gas. Escaping gas 82 can thus pass outwardly from the interior of the cartridge 50, and sterilising gas, such as ethylene oxide, can enter. So that the gas throughflow is not too heavily impeded by the thread, openings 84 are provided in the connection piece 79, which openings do not fully penetrate the thread, but enable a throughflow of gas (see FIG. 20). The discharge tube 78 can also have a discharge tube extension 86, which is connected to the rest of the discharge tube 78 by means of a predetermined breaking point. Depending on requirements, the bone cement dough can then be applied through the discharge tube extension 86 (see FIG. 21) or through the shorter, broken-off discharge tube 78 (see FIG. 19).

The key components of devices according to one embodiment can be produced economically from plastic by press-out moulding.

In all various devices according to FIGS. 1 to 21, it can be provided that a resilient hose (not illustrated) is arranged on the discharge tube 18, 72 or on the discharge tube connection piece 66 or on the connection piece 79, which resilient hose can end in a trocar. The device can thus be used for vertebroplasty.

In order to prevent the bone cement dough from continuing to flow out, a pressure relief valve (not illustrated) with a chamber for receiving bone cement dough 44 can be provided in accordance with one embodiment on the discharge tube 18, 72 or on the discharge tube connection piece 66 or on the connection piece 79. By opening the pressure relief valve, a pressure acting on the bone cement dough 44 in the interior can be reduced, without the bone cement dough continuing to run at the application tip for a long period of time. With the chamber, the bone cement dough is prevented from passing into the surrounding environment.

The powder 1, in all exemplary embodiments, contains either 0.0-15.0% by weight radiopacer, 0.4-3.0% by weight dibenzoyl peroxide, 79.5-99.3% by weight polymethyl methacrylate and/or polymethyl methacrylate copolymer, and 0.1-2.5% by weight additive, or the powder 1 contains 1.0-10% by weight anti-infective or antiseptic, 0.0-15.0% by weight radiopacer, 0.4-3.0% by weight dibenzoyl peroxide, 69.5-98.3% by weight polymethyl methacrylate and/or polymethyl methacrylate copolymer, and 0.1-2.5% by weight additive.

The features of embodiments disclosed in the above description, and in the claims, Figures and exemplary embodiments can be important, both individually and in any combination, for the realization of the various embodiments.

What is claimed is:

1. A device for mixing a polymethyl methacrylate bone cement formed of two starting components and for storing the starting components of the bone cement, the device comprising a tubular cartridge and with a cylindrical interior each extending along a longitudinal axis;
    wherein a powder is contained as a first starting component in a front part of the interior of the cartridge and a container containing a monomer liquid as a second starting component is arranged in a rear part of the interior of the cartridge;
    wherein a discharge piston is arranged between the container and the powder;
    wherein a conveying piston is arranged on the side of the container opposite the discharge piston, so that the container containing the monomer liquid is arranged between the conveying piston and the discharge piston;
    wherein the discharge piston and the conveying piston are arranged in the interior of the cartridge movably along the longitudinal axis of the interior of the cartridge;
    wherein a conduit means is provided that connects the front part and the rear part of the interior of the cartridge to one another in a manner permeable for the monomer liquid and for gases and which is impermeable for the powder.

2. The device according to claim 1, characterized in that at least one feedthrough is provided in the discharge piston and/or between the discharge piston and the inner wall of the interior as the conduit means, by which the front part of the interior and the rear part of the interior are connected to one another, wherein a filter impermeable for the powder and permeable for the monomer liquid and gases is arranged in or on the at least one feedthrough.

3. The device according to claim 1, characterized in that by advancing the conveying piston in the direction of the discharge piston, the container is openable, the monomer liquid is pressable into the powder, and the discharge piston is then pushable by the conveying piston in the direction of the front side of the cartridge.

4. The device according to claim 3, characterized in that by pushing the conveying piston in the direction of the front side of the cartridge, the discharge piston is pressable in the direction of a cartridge head and a bone cement dough produced in the front part of the interior from the powder and the monomer liquid is thus pressable out through an opening.

5. The device according to claim 1, characterized in that the container for the monomer liquid is a glass ampoule or plastic ampoule, which is breakable open by a movement of the conveying piston, or the container for the monomer liquid is a film bag, which is rippable, pierceable or slittable by the movement of the conveying piston.

6. The device according to claim 1, characterized in that a detent means is arranged on the discharge piston, so that the discharge piston can latch with the cartridge between the front and the rear part of the interior, wherein this latching cannot be released by the forces occurring as the container is opened and a pressure exerted onto the monomer liquid by the conveying piston, but is releasable by a pressure acting on the discharge piston directly from the conveying piston.

7. The device according to claim 1, characterized in that the cartridge is composed of a front cartridge part and a rear cartridge part, which are fixedly connected to one another, and wherein a cartridge head is fastened to the front cartridge part.

8. The device according to claim 1, characterized in that at least one filling material is arranged in the rear part of the interior between the container and the discharge piston, and wherein the filling material is a foam material or is formed by plastic beads.

9. The device according to claim 1, characterized in that a mesh, a sieve, or a splinter shield is arranged between the powder and the container for the monomer liquid, and is arranged between the discharge piston and the container or is arranged in feedthroughs in or on the discharge piston.

10. The device according to claim 1, characterized in that the conveying piston closes the interior of the cartridge at a cartridge base in a pressure-tight and liquid-tight manner.

11. The device according to claim 1, characterized in that at least one opening aid for opening the container for the monomer liquid is arranged on the side of the discharge piston facing towards the container, and wherein the at least one opening aid is at least one blade, edge or at least one pin.

12. The device according to claim 1, characterized in that the volume of the monomer liquid in the container is at least as large as the volume of gaps filled with air between the powder particles in the front part of the interior, or is at least as large or exactly the same size as the volume of the gaps filled with air between the powder particles in the front part of the interior and the rear part of the interior when the conveying piston bears against the discharge piston, minus the volume of the material of the container and, as applicable, the volume of filling material in the rear part of the interior.

13. The device according to claim 1, characterized in that a receiver for excess monomer liquid is provided at the front end of the cartridge or in a cartridge head at the front side of the cartridge, wherein the powder cannot enter the receiver, and wherein the receiver is a hydrophilic spongy structure.

14. The device according to claim 1, characterized in that the powder is pressed into the front part of the interior under pressure in the front part of the interior.

15. The device according to claim 1, characterized in that a ventilation opening in the wall of the cartridge is arranged directly above the conveying piston and connects the rear part of the interior to the surrounding atmosphere.

16. The device according to claim 1, characterized in that a multi-part closure system comprising a discharge opening is arranged on a cartridge head arranged at the front side of the cartridge, wherein at least two parts of the closure system are movable relative to one another, driven by a movement of mixed bone cement dough, and the discharge opening opens as a result of this movement of the at least two parts of the closure system relative to one another, wherein the movement of the mixed bone cement dough is drivable by a pressure of the discharge piston on the bone cement dough, and wherein part of the closure system comprises a connection between the front part of the interior of the cartridge and the surrounding environment of the device, which connection is permeable for gases, but is impermeable for the powder and the monomer liquid.

17. The device according to claim 16, characterized in that the closure system has a wall with the discharge opening and a stopper, wherein the discharge opening is connected to the surrounding environment of the cartridge and the stopper closes the discharge opening to the surrounding environment when the cartridge is closed in a starting state, wherein either the wall with the discharge opening is movable by the pressure of the bone cement dough and the stopper is fixed relative to the cartridge, or the stopper is movable by the pressure of the bone cement dough and the wall is fixed or fixable relative to the cartridge.

18. The device according to claim 16, characterized in that the closure system comprises a wall which is gas-permeable, but impermeable for powder and liquids, wherein the wall is arranged in the cartridge in such a way that the pressure of the bone cement dough acts on the wall and thus moves a stopper or a cover with the wall relative to the cartridge and thus opens the cartridge or thus moves a discharge opening with the wall relative to the cartridge and thus removes a stopper, which is fixedly connected to the cartridge, from the discharge opening, wherein the wall comprises a plate with pores.

19. The device according to claim 1, characterized in that a hydrophilic additive is distributed in the powder, with which additive the monomer liquid is distributable throughout the powder, and without a polymerisation of the bone cement before distributing the monomer liquid throughout the powder.

20. The device according to claim 1, characterized in that the powder comprises at least one particulate polymethyl methacrylate or polymethyl methacrylate copolymer of the sieve fraction smaller than 100 µm, an initiator, and at least one particulate or fibrous additive that is insoluble in methyl methacrylate.

21. The device according to claim 1, characterized in that the front part of the interior of the cartridge is connected to the surrounding environment of the device by means of a connection that is permeable for gases, but impermeable for the powder and for the monomer liquid.

22. A method for mixing and applying a bone cement with a device according to claim 1, the method comprising:
pushing the conveying piston in the direction of a cartridge head, which is arranged at the front side of the cartridge;
opening the container by the movement of the conveying piston in the interior of the cartridge;
then, pressing the monomer liquid into the powder, and thus forming a bone cement dough, and
then, pushing the discharge piston in the direction of the cartridge head, thereby driving the bone cement dough out from the cartridge through the cartridge head by the movement of the discharge piston.

23. The method according to claim 22, characterized in that the discharge piston is latched with the inner wall of the cartridge as the container is opened and as the monomer liquid is pressed into the powder, wherein the latching of the discharge piston with the inner wall of the cartridge is released by the pressure of the conveying piston on the discharge piston, and the conveying piston then pushes the discharge piston in the direction of the cartridge head.

24. The method according to claim 22, characterized in that the device is inserted into a press-out apparatus and a ram of the press-out apparatus is advanced, by means of which ram the conveying piston is driven in the direction of the cartridge head.

25. The method according to claim 22, characterized in that the monomer liquid is distributed in the powder with the aid of a hydrophilic additive, and wherein the powder is compressed or contained under a mechanical pressure in the front part of the interior.

26. The method according to claim 22, characterized in that the container is compressed by the movement of the conveying piston and is destroyed as a result.

27. The method according to claim 22, characterized in that a discharge opening on the cartridge head is initially closed with the aid of a closure system, wherein the closure system is opened by the pressure exerted onto bone cement dough by the conveying piston and via the discharge piston, wherein the bone cement dough is then pressed out through the discharge opening with the same pressure.

28. The method according to claim 27, characterized in that part of the closure system is a stopper, which closes the discharge opening, wherein the stopper is pushed out from the discharge opening with the cement dough or a wall, relative to the cartridge, with the discharge opening is pushed by the bone cement dough in the direction of the front side of the cartridge, thus releasing a stopper or a cover, which is fixed to the cartridge, from the discharge opening.

29. A device for mixing a polymethyl methacrylate bone cement formed of two starting components and for storing the starting components of the bone cement, the device comprising a tubular cartridge with a cylindrical interior extending along a longitudinal axis;
wherein a powder is contained as a first starting component in a front part of the interior of the cartridge and a container containing a monomer liquid as a second starting component is arranged in a rear part of the interior of the cartridge;
wherein a discharge piston is arranged between the container and the powder;
wherein a conveying piston is arranged on the side of the container opposite the discharge piston, so that the container containing the monomer liquid is arranged between the conveying piston and the discharge piston;

wherein the discharge piston and the conveying piston are arranged in the interior of the cartridge movably along the longitudinal axis of the cylindrical interior of the cartridge;

wherein a conduit means is provided that connects the front part and the rear part of the interior of the cartridge to one another in a manner permeable for the monomer liquid and for gases and which is impermeable for the powder;

characterized in that the discharge piston is formed as a perforated plate or as a mesh screen and at least one open-pored plastic layer which is gas-permeable, but impermeable for powder particles closes the holes or the mesh openings in a manner that is gas-permeable and impermeable for powder particles.

30. A method for producing a prepacked PMMA cement cartridge system which is suitable for mixing and applying a PMMA bone cement dough and in which a powder is stored as a starting component of the bone cement, the method comprising:

providing a cartridge having a cylindrical interior and a discharge piston having an external periphery matching the cylindrical interior;

filling the powder into the interior of the cartridge, wherein the powder comprises a cement powder as main component for producing the bone cement dough, and the powder additionally comprises a hydrophilic additive, which is distributed in the cement powder;

compressing the powder in the interior of the cartridge between the discharge piston and a wall, which delimits the cylindrical interior on a front side, by reducing the distance between the discharge piston and the wall in the interior; and locking, supporting or fastening the wall and/or the discharge piston, so that, during the storage of the powder, a mechanical pressure is exerted onto the powder by the wall and the discharge piston, and the powder remains compacted;

characterized in that at least one container containing a monomer liquid as further starting component of the bone cement is arranged in the interior of the cartridge, and a conveying piston is arranged at the cartridge base of the cartridge, wherein the at least one container is arranged between the conveying piston and the discharge piston.

31. A method for producing a prepacked PMMA cement cartridge system which is suitable for mixing and applying a PMMA bone cement dough and in which a powder is stored as a starting component of the bone cement, the method comprising:

providing a cartridge having a cylindrical interior and a discharge piston having an external periphery matching the cylindrical interior;

filling the powder into the interior of the cartridge, wherein the powder comprises a cement powder as main component for producing the bone cement dough, and the powder additionally comprises a hydrophilic additive, which is distributed in the cement powder;

compressing the powder in the interior of the cartridge between the discharge piston and a wall, which delimits the cylindrical interior on a front side, by reducing the distance between the discharge piston and the wall in the interior; and locking, supporting or fastening the wall and/or the discharge piston, so that, during the storage of the powder, a mechanical pressure is exerted onto the powder by the wall and the discharge piston, and the powder remains compacted;

characterized in that at least one container containing a monomer liquid as further starting component of the bone cement is arranged in the interior of the cartridge, and a conveying piston is arranged at the cartridge base of the cartridge, wherein the at least one container is arranged between the conveying piston and the discharge piston, and a filling material of at least one foam material body and/or plastic grains is additionally arranged in the rear part of the interior of the cartridge, in which the at least one container is arranged.

32. The method according to claim 31, characterized in that the discharge piston is supported by the at least one container and the conveying piston arranged at the cartridge base in the interior of the cartridge.

* * * * *